United States Patent [19]

Ranscht

[11] Patent Number: 5,811,518
[45] Date of Patent: *Sep. 22, 1998

[54] T-CADHERIN ADHESION MOLECULE

[75] Inventor: Barbara Ranscht, Del Mar, Calif.

[73] Assignee: La Jolla Cancer Research Foundation, La Jolla, Calif.

[ * ] Notice: The term of this patent shall not extend beyond the expiration date of Pat. No. 5,585,351.

[21] Appl. No.: 474,067

[22] Filed: Jun. 7, 1995

Related U.S. Application Data

[63] Continuation of Ser. No. 213,361, Mar. 14, 1994, Pat. No. 5,585,351, which is a continuation of Ser. No. 607,293, Oct. 30, 1990, abandoned.

[51] Int. Cl.$^6$ ............................................. C07K 14/705
[52] U.S. Cl. ...................... 530/350; 530/395; 435/69.1
[58] Field of Search .................................. 530/350, 395; 514/12; 435/69.1

[56] References Cited

U.S. PATENT DOCUMENTS 5,585,351  12/1996  Ranscht ...................................... 514/12

OTHER PUBLICATIONS

Sigma Catalog, 1989, p. 116.
Neugehauer, et al., *Chem. Abst.* 109:167903c (1988).
Laemmli "Cleavage of Structural Proteins During the Assembly of the Head Bacteriophage T4." *Nature* 227:680–685 (1970).
Ranscht et al., "A Neuronal Surface Glycoprotein Associated with the Cytoskeleton." *J. Cell Biol.* 99:1803–1813 (1984).
Edelman et al., "Cellular Expression of Liver and Neural Cell Adhesion Molecules After Transfection with Their cDNAs Results in Specific Cell–Binding." *Proc. Natl.Acad.Sci. USA* 84:8502–8506 (1987).
Gallin et al., "Sequence Analysis of a cDNA Clone Encoding the Liver Cell Adhesion Molecule, L–CAM." *Proc. Natl. Acad. Sci. USA* 84:2808–2812 (1987).
Hatta et al., "Spatial and Temporal Expression Pattern of N–Cadherin Cell Adhesion Molecules Correlated with Morphogenetic Processes of Chicken Embryos." *Dev. Biol.* 120:215–217 (1987).
Nagafuchi et al.,"Transformation of Cell Adhesion Properties by Exogenously Introduced E–Cadherin cDNA." *Nature* 329:341–343 (1987).
Nose et al., "Isolation of Placental Cadherin cDNA: Identification of a Novel Gene Family of Cell–Adhesion Molecules." *EMBO J.* 6(12):3655–3661 (1987).
Ringwald et al., "The Structure of Cell Adhesion Molecule Uvomorulin. Insights into the Molecular Mechanism of Ca$^2$–dependent Cell Adhesion." *EMBO J.* 6(12):3647 (1987).
Hatta et al., "Cloning and Expression of cDNA Encoding a Neural Calcium–dependent Cell Adhesion Molecule: Its Identity in the Cadherin Gene Family." *J. Cell. Biol.* 106:873–881 (1988).

Mege et al., "Construction of Epithelioid Sheets by Transfection of Mouse Sarcoma Cells with cDNAs for Chicken Cell Adhesion Molecules." *Proc. Natl. Acad. Sci. USA* 85:7274–7278 (1988).
Nagafuchi and Takeichi, "Cell Binding Function of E–Cadherin is Regulated by the Cytoplasmic Domain." *EMBO J.* 7(12)3679–3684 (1988).
Neugebauer et al., "N–cadherin, NCAM, and Integrins Promote Retinal Neurite Outgrowth on Astrocytes in Vitro." *Chem. Abstract* 109:487 Abstract No. 109:167903c (1988).
Takeichi, "The Cadherins: Cell–Cell Adhesion Molecules Controlling Animal Morphogenesis." *Development* 102:639–655 (1988).
Kemler, and Ozawa, "Uvomorulin–Catenin Complex: Cytoplasmic Anchorage of a $Ca^{2+}$–dependent Cell Adhesion Molecule." *BioEssays* 11(4):88–91 (1989).
Moss and White, "A $Ca^{2+}$–sensitive Glycoprotein, GP90, Associated with the Cytoskeleton from Brain and Gizzard." *J. Cell Sci.* 93:85–94 (1989).
Nagafuchi and Takeichi, "Transmembrane Control of Cadherin–Mediated Cell Adhesion: a 94 kDa Protein Functionally Associated with a Specific Region of the Cytoplasmic Domain of E–Cadherin." *Cell Regulation* 1:37–44 (1989).
Ozawa et al., "The Cytoplasmic Domain of the Cell Adhesion Molecule Uvomorulin Associates with Three Independent Proteins Structurally Related in Different Species." *EMBO J.* 8(6):1711–1717 (1989).
Ranscht and Dours, "Selective Expression of a Novel Cadherin in the Pathways of Developing Motor and Commissural Axons." *Society for Neuroscience Abstracts* 15(part 1), Abstract No. 382.6 (1989).
Bixby and Zhang, "Purified N–Cadherin is a Potent Substrate for the Rapid Induction of Neurite Outgrowth." *J. Cell Biol.* 110:1253–1260 (1990).
Matsuzaki et al., "DNAs of Cell Adhesion Molecule of Different Specificity Induce Changes in Cell Shape and Border Formation in Cultured S180 Cells." *J. Cell. Biol* 110:1239–1252 (1990).
McNeill et al., "Novel Function of the Cell Adhesion Molecule Uvomorulin as an Inducer of Cell Surface Polarity." *Cell* 62:309–316 (1990).

(List continued on next page.)

*Primary Examiner*—Stephen Walsh
*Assistant Examiner*—Karen E. Brown
*Attorney, Agent, or Firm*—Campbell & Flores LLP

[57] ABSTRACT

The invention provides substantially purified T-cadherin polypeptides and isolated nucleic acids which encode the T-cadherin polypeptides. Antibodies reactive with various forms of T-cadherin, but not reactive with N-, E- or P-cadherin are also provided. The invention provides methods for detecting the various forms of T-cadherin in a subject as well as a method of detecting tumor growth which consists of inhibiting the activity of T-cadherin in a tumor. A method of affecting traumatized neurons is provided. The method entails treating traumatized neurons with a therapeutically effective dose of T-cadherin.

3 Claims, 19 Drawing Sheets

OTHER PUBLICATIONS

Nose et al., "Localization of Specificity Determining Sites in Cadherin Cell Adhesion Molecules." *Cell* 61:147–155 (1990).

Ozawa et al., "Uvomorulin–catenin Complex Formation is Regulated by a Specific Domain in the Cytoplasmic Region of the Cell Adhesion Molecule." *Proc. Natl. Acad. Sci. USA* 87:4246–4250 (1990).

Ozawa and Kemler, "Correct Proteolytic Cleavage is required for the Cell Adhesive Function of Uvomorulin," *J. Cell Biol.* 111:1645–1650 (1990).

Ozawa et al., "Single Amino Acid Substitutions in one $Ca^{2+}$ Binding Site of Uvomorulin Abolish the Adhesion Function." *Cell* 63:1033–1038 (1990).

Takeichi, "Cadherins: a Molecular Family Important in Selective Cell–Cell Adhesion." *Annu. Rev. Biochem.* 59:237–252 (1990).

Ranscht, "Cadherin Cell Adhesion Molecules in Vertebrate Neural Development." *Seminars in the Neurosciences.* 3:285–296 (1991).

Ranscht and Dours–Zimmerman, "T–Cadherin, A Novel Cadherin Cell Adhesion Molecule in the Nervous System Lacks the Conserved Cytoplasmic Region." *Neuron* 7:391–402 (1991).

|       | |
|---|---|
| 1<br>-22 | GAATTCCGAATGAAAAAGCCTCTGGTACGTTCTAGTCTGGCAAAATGCAGCACAAACTCAACTTACTCTGTCCTTTCTGCTGTCCAG<br>                                              M  Q  H  K  T  Q  L  T  L  S  F  L  L  S  Q |
| 90<br>-7 | GTTCTGTTGCTGCGTGTGCAGAAGATTTAGAATGCACCCCTGATTCCAGCAAAAGGTTTTTATATTGAACAGCCATTTGAATTCACA<br>V  L  L  A  C  A  E  D  L  E  C  T  P  G  F  Q  Q  K  V  F  Y  I  E  Q  P  F  E  F  T |
| 180<br>24 | GAGGACCAGCCAATTCTGAACCTGGTCTTTGATGACTGCAAGGGGAATAACAAATTGAACTTCGAAGTTTCTAACCCAGACTTTAAGGTG<br>E  D  Q  P  I  L  N  L  V  F  D  D  C  K  G  N  N  K  L  N  F  E  V  S  N  P  D  F  K  V |
| 270<br>54 | GAACACGATGGATCTTTAGTTGCACTGAAGAATGTATCAGAAGCTGGCAGAGCTTTGTTTGTCCATGCACGGTCTGAGCATGCTGAGGAT<br>E  H  D  G  S  L  V  A  L  K  N  V  S  E  A  G  R  A  L  F  V  H  A  R  S  E  H  A  E  D |
| 360<br>84 | ATGGCAGAAATTTGATTGTGGAGCTGATGAGAAGCACGATGCATTAAAGGAAATCTTTAAGATAGAAGGCAACCTTGGAATTCCAAGA<br>M  A  E  I  L  I  V  G  A  D  E  K  H  D  A  L  K  E  I  F  K  I  E  G  N  L  G  I  P  R |
| 450<br>114 | CAAAAAAGGGCTATTCTGGCGACTCCAATATTAATTCCAGAAAATCAAGACCCATTCCCAGATCAGTTGGCAAGGTCATCAGGAGT<br>Q  K  R  A  I  L  A  T  P  I  L  I  P  E  N  Q  R  P  P  F  P  R  S  V  G  K  V  I  R  S |
| 540<br>144 | GAAGGGACAGAGGGAGCAAAGTTCCGACTCTCTGGTAAGGGAGTAGATCAAGACCCGAAAGGAATTTTAGAATCAATGAGATCAGTGGG<br>E  G  T  E  G  A  K  F  R  L  S  G  K  G  V  D  Q  D  P  K  G  I  F  R  I  N  E  I  S  G |
| 630<br>174 | GATGTCTCTGTGACCCGACCTCTGGATAGAGAAGCAATATGAGCTGGAAGTTGAAGTAACGGATTTAAGTGGGAAAATCATT<br>D  V  S  V  T  R  P  L  D  R  E  A  I  A  N  Y  E  L  E  V  E  V  T  D  L  S  G  K  I  I |
| 720<br>204 | GATGGCCCAGTCGTCCGCTTAGATATTTCTGTTATTGATCAAAATGATAACAGGCCGATGTTCAAAGAAGGACCCTATGTTGGTCACGTCATG<br>D  G  P  V  R  L  D  I  S  V  I  D  Q  N  D  N  R  P  M  F  K  E  G  P  Y  V  G  H  V  M |
| 810<br>234 | GAAGGATCCCTACAGGAACACTTACCAAACCTTGATGCTGATGATCCTAGCACAGACAACGCTCTTCTGCGGTATAAC<br>E  G  S  P  T  G  T  T  V  M  R  M  T  A  F  D  A  D  D  P  S  T  D  N  A  L  L  R  Y  N |
| 900<br>264 | ATCCTCAAGCAGACACCTACCAAACTTCCCCAAATATGTTCTACATTGACCCAGAAAAGGGAGATATTGTCACAGTGGTGTCACCTGTA<br>I  L  K  Q  T  P  T  K  P  S  P  N  M  F  Y  I  D  P  E  K  G  D  I  V  T  V  V  S  P  V |
| 990<br>294 | CTGCTGGATCGTGAGACAATGGAAACGCCGAAGTACGAGCTGGTTATTGAAGCCAAGGATATGGGCGGCCATGATGTGGACTTACTGGA<br>L  L  D  R  E  T  M  E  T  P  K  Y  E  L  V  I  E  A  K  D  M  G  G  H  D  V  G  L  T  G |

FIG.2A

```
1080  ACTGCAACTGCCACTATTCTTATTGATGACAAAAACGACCACCCACCAGAATTACCAAGAGGAGTTTCAGGCCACAGTAAAGGAAGGA
 324   T  A  T  I  I  L  I  D  D  K  N  D  H  P  P  E  F  T  K  K  E  F  Q  A  T  V  K  E  G

1170  GTCACAGGAGTAATAGTAAACTTAACTGTTGGTGATCGTGACCGAGATGACCCAGCAACTGGAGAGCTGTCTACACTATTAACGGA
 354   V  T  G  V  I  V  N  L  T  V  G  D  R  D  D  P  A  T  G  A  W  R  A  V  Y  T  I  I  N  .  G

1260  AATCCAGGGCAGAGTTTTGAAATCCATACCAATCCCCAGACTAATGAGGGAATGCTCTCTGTGTCAAACCTTTAGACTATGAGATTCA
 384   N  P  G  Q  S  F  E  I  H  T  N  P  Q  T  N  E  G  M  L  S  V  V  K  P  L  D  Y  E  I  S

1350  GCATTCACACATTGCTGATAAAAGTAGAAAATGAAGACCCCGTTGATTCCAGACATAGCCTACGGTCCCAGTTCCACAGCAACAGTTCAG
 414   A  F  H  T  L  L  I  K  V  E  N  E  D  P  L  I  P  D  I  A  Y  G  P  S  S  T  A  T  V  Q

1440  ATCACCGTTGAGGATGTGAATGAAGGCCCCGTGTTTTTCCACCCAAATCCAATGACAGTGACAAAACAAGAGAACATCCTATTGGCAGCATT
 444   I  T  V  E  D  V  N  E  G  P  V  F  H  P  N  P  M  T  V  T  K  Q  E  N  I  P  I  G  S  I

1530  GTGTTAACAGTAAACATGGCCACTGATCCAGATACTTTGCAACATCAGATCAGGTATTCAGTTTACAAGGATCCAGCAAGCTGGCTAGAG
 474   V  L  T  V  N  A  T  D  P  D  T  L  Q  H  Q  T  I  R  Y  S  V  Y  K  D  P  A  S  W  L  E

1620  ATTAATCCCACCAATGGTACCGTTGCCACCACTGCTGTCCTGGATCGGGAATCTCCTCATGTTCAGGATAACAAATACACTGCTCTCTTC
 504   I  N  P  T  N  G  T  V  A  T  T  A  V  L  D  R  E  S  P  H  V  Q  D  N  K  Y  T  A  L  F

1710  CTGGCAATAGACAGTGGTGGTAACCCTCCTGCTACAGGTACAACTTTACACCATCACCTTGGAGGACGTCAATGACAATGTCCCCTCCTT
 534   L  A  I  D  S  G  N  P  P  A  T  G  T  T  L  H  I  T  L  E  D  V  N  D  N  V  P  S  L

1800  TACCCAACACTGGCAAAAGTCTGTGATGATGCTAAAGATCTAAGAGTAGTGGTACTAGGAGCATCAGACAAAGACCTCCATCCCAACACA
 564   Y  P  T  L  A  K  V  C  D  D  A  K  D  L  R  V  V  V  L  G  A  S  D  K  D  L  H  P  N  T

1890  GATCCATTTAAATTTGAACTGAGTAAGCAATCTGGTCCAGAAAAGTTATGGAGAATCAACAAGCTTAACATACTCATGCCCAGTTGTC
 594   D  P  F  K  F  E  L  S  K  Q  S  G  P  P  E  K  L  W  R  I  N  K  L  N  T  H  A  Q  V  V

1980  CTGCTTCAAAACCTGAAAAAGGCCAATTACAACATCCCAATCTCAGTGACAGATTCTGGAAAACCACCTCTGACTAACAACAGAACTG
 624   L  Q  N  L  K  K  A  N  Y  N  I  P  I  S  V  T  D  S  G  K  P  P  L  T  N  N  T  E  L
```

```
  1       GAATTCCAAAAAGCCTCTGGTAGTTCTAGTCTGGCAAAATGCAGCACAAAACTCAACTTACTCTGTCCTTTCTGTCGTCCAGTTCTG
 -22                                      M  Q  H  K  T  Q  L  T  L  S  F  L  L  S  Q  V  L

91       TTGCTTGCGTGTGCAGAAGATTTAGAATGCACCCCCTGGATTCCAGCAAAAGTTTTTTATATTGACAGCCATTGAATTCACAGAGGAC
 -5        L  L  A  C  A  E  D  L  E  C  T  P  G  F  Q  Q  K  V  F  Y  I  E  Q  P  F  E  F  T  E  D

181       CAGCCAATTCTGAACCTGGTCTTCGATGACTGCAAGGGGAATAACAAATTGAACTTCGAAGTTCTAACCAGAGACTTAAGGTGGAACAC
 26        Q  P  I  L  N  L  V  F  D  D  C  K  G  N  N  K  L  N  F  E  V  S  N  P  D  F  K  V  E  H

271       GATGGATCTTTAGTTGCACTGAAGAATGTATCAGAAGCTGGCAGAGCTTTGTTTGTCCATGCACGGTCTGAGCATGCTGAGGATATGGCA
 56        D  G  S  L  V  A  L  K  N  V  S  E  A  G  R  A  L  F  V  H  A  R  S  E  H  A  E  D  M  A

361       GAAATTTGATGTTGTGGAGCTGATGAGAAGCACGATGCATTAAAGGAAATCTTTAAGAAGGCAACTTGGAATTCCAAGACAAAA
 86        E  I  L  I  V  G  A  D  E  K  H  D  A  L  K  E  I  F  K  I  E  G  N  L  G  I  P  R  Q  K

451       AGGGCTATTCTGGCAACTCCAATATTAATTCCAGAAAATCAAAGACCCATTCCCAGATCAGTTGGCAAGTTCATCAGGAGTGAAGGG
116        R  A  I  L  A  T  P  I  L  I  P  E  N  Q  R  P  P  F  P  P  R  S  V  G  K  V  I  R  S  E  G

541       ACAGAGGGAGCAAAGTTCCGACTCTCTGGTAAGGGAGTAGATCAAGACCCGAAAGGAATTTTAGAATCAATGAGATCAGTGGGATGTC
146        T  E  G  A  K  F  R  L  S  G  K  G  V  D  Q  D  P  K  G  I  F  R  I  N  E  I  S  G  D  V

631       TCTGTGACCCGACCCCTGGATAGAGAAGCAATAGCCAATTATGAGCTGAAGTTGAAGTAACGGATTAAGTGGGAAAATCATTGATGGC
176        S  V  T  R  P  L  D  R  E  A  I  A  N  Y  E  L  E  V  T  D  L  S  G  K  I  I  D  G

721       CCAGTCCGCCTAGATATTTCTGTTATTGATCAAAATGATAACAGGCCGATGTTCAAAGAAGGACCCTATGTTGGTCACGTCATGGAAGGA
206        P  V  R  L  D  I  S  V  I  D  Q  N  D  N  R  P  M  F  K  E  G  P  Y  V  G  H  V  M  E  G

811       TCCCCTACAGGAACAACTGTGATGCGGATGACAGCATTTGATGATCCTAGCACAGACAACGCTCTTCGCGTATAACATCCTC
236        S  P  T  G  T  T  V  M  R  M  T  A  F  D  A  D  D  P  S  T  D  N  A  L  L  R  Y  N  I  L

901       AAGCAGACACCTACCAAACCTTCCCACAAATATGTTCTACATTGACCCCAGAAAAGGGAGATATTGTCACAGTGGTGTCGCCTGTACTGCTG
266        K  Q  T  P  T  K  P  S  P  N  M  F  Y  I  D  P  E  K  G  D  I  V  T  V  V  S  P  V  L  L

991       GATCGTGAGACAATGGAAACGCCAAGTACGAAGCTGTTATTGAAGCTGAAGAAGGCGCCATGATATGGGGCGGCCATGATGTGGGACTTACTGGAACTGCA
296        D  R  E  T  M  E  T  P  K  Y  E  L  V  I  E  A  K  D  M  G  G  H  D  V  G  L  T  G  T  A
```

FIG.2D

```
1081        ACTGCCACTATTCTTATTGATGACAAAAACGACCACCCACCAGAATTTACCAAGAAGGAGTTTCAGGCCACAGTAAAGGAAGAGTCACA
 326         T  A  T  I  L  I  D  D  K  N  D  H  P  P  E  F  T  K  K  E  F  Q  A  T  V  K  E  G  V  T

1171        GGAGTAATAGTAAACTTAACTGTTGGTGACCGAGATGACCCAGCAACTGGAGCATGGAGAGCTGTCTACACTATTATTAACGGAAATCCA
 356         G  V  I  V  N  L  T  V  G  D  R  D  D  P  A  T  G  A  W  R  A  V  Y  T  I  I  N  G  N  P

1261        GGGCAGAGTTTTGAAATCCATACCAATCCCCAGACTAATGAGGGAATGCTCTCTGTTGTCAAACCTTTAGACTATGAGATTTCAGCATTT
 386         G  Q  S  F  E  I  H  T  N  P  Q  T  N  E  G  M  L  S  V  V  K  P  L  D  Y  E  I  S  A  F

1351        CACACAATTGCTGATAAAAGTAGAAAAATGAAGAACATAGCCGTTGATTCCAGAGTCCACAGCAACAGTTCAGATCACC
 416         H  T  L  L  I  K  V  E  N  E  D  P  L  I  P  D  I  A  Y  G  P  S  S  T  A  T  V  Q  I  T

1441        GTTGAGGATGTGAATGAAGGCCCTGTTTTCCACCCAAATCCAATGACAGTGACAAAACAAGAGAACATCCCTATTGGCAGCATTGTGTTA
 446         V  E  D  V  N  E  G  P  V  F  H  P  N  P  M  T  V  T  K  Q  E  N  I  P  I  G  S  I  V  L

1531        ACAGTAAATGCCACTGATCCTGATACTTTGCAACATCAGATCAGGTATTCAGTTTACAAGGATCCTGCTAGCTGGCTAGAGATTAAT
 476         T  V  N  A  T  D  P  D  T  L  Q  H  Q  T  I  R  Y  S  V  Y  K  D  P  A  S  W  L  E  I  N

1621        CCCACCAATGGTACCGTTGCCACCACTGCTGTCCTGGATCGGGAATCTCCGCATGTTCAGGATAACAAATACACTGCTCTCTTCCTGCA
 506         P  T  N  G  T  V  A  T  T  A  V  L  D  R  E  S  P  H  V  Q  D  N  K  Y  T  A  L  F  L  A

1711        ATAGACAGTGGTAACCCTCCTGCTACAGGTACAGGAACTTTACACATCACTTTGGAGGACGTCAATGACAATGTCCCCCTTTACCA
 536         I  D  S  G  N  P  P  A  T  G  T  G  T  L  H  I  T  L  E  D  V  N  D  N  V  P  S  L  Y  P

1801        ACACTGGCAAAGTCTGTGATGATGCTAAAGATCTCAGATAGTGTTCTAGGAGCATCAGACAAAGACCTCCATCCAACACAGATCCA
 566         T  L  A  K  V  C  D  D  A  K  D  L  R  V  V  L  G  A  S  D  K  D  L  H  P  N  T  D  P
```

```
SIG  T  MQHKTQLTLSFLLSQVL.LLACA.....
     N  MCRIAGTPPRILPPLALMLLAALQQAPI
     L  ...........................
     E  MGARCRSFSALLILLQVSSWLCQELEP.
     P  MELLSGPHAFLLLLLQVCWLRSVVSEP.

PRE  T  ....EDLECTPGFQQKV.FYIEQPFEFTE.DQPILNLVFDDCKGNNKLNFEVSNP.DFKVEHDGSLVA.L
     N  KATCEDMLCKMGFPEDV.HSAVVSRSVHG.GQPLLNVRFQSCDENRKIYFGSSEPEDFRVGEDGVVYAER
     L  .....................DSVAA.GRELGRVSFAACS.GRPWAVYVPTDTRFKVNGDGVVSTKR
     E  ......ESCSPGFSSEV.YTFPVPERHLERGHVLGRVRFEGCT.GRPRTAFFSEDSRFKVATDCTITVKR
     P  ........YRAGFIGEAGVTLEVEGTDLEPSQVLGKVALAGQG............................

EC1  T  AILATPILIPENQR.PPFPRSVGKVIRSEGTEGA.....KFRLS..GKGVDQDPKGIFRINEIS.....G
     N  DWVIPPINLPENSR.GPFPQELVR.IRSDRDKSL.....SLRYSVTGPGADQPPTGIFIINPIS.....G
     L  DWVIPPISCLENHR.GPYPMRLVQ.IKSNKDKES.....KVYYSITGQGADSPPVGIFIIERET.....G
     E  DWVIPPISCPENEK.GEFPKNLVQ.IKSNRDKET.....KVFYSITGQGADKPPVGVFIIERET.....G
     P  EWVMPPIFVPENGK.GPFPQRLNQ.LKSNKDRGT.....KIFYSITGPGADSPPEGVFTIEKES.....G
              **  **    *     *          *  * ** *** **      *       *      *

EC2  T  KEGPYVGHVMEGSPTGTTVM...RMTAFDADD.PSTDNALLRYNILKQTPTKPSPNMFYIDPEK.....G
     N  LHQVWNGTVPEGSKPGTYVM...TVTAIDADD.PNAQNGMLRYRILSQAPSSPSPNMFTINNET.....G
     L  IKEVFVGYIEENAKPGTSVM...TVNATDADDAVNTDNGIVSYSIVSQQPPRPHPQMFTIDPAK.....G
     E  TQEVFEGSVAEGAVPGTSVM...KVSATDADDDVNTYNAAIAYTIVSQDPELPHKNMFTVNRDT.....G
     P  TQDTFRGSVIEGVMPGTSVM...QVTATDEDDAVNTYNGVVAYSIHSQEPKEPHDLMFTLHKST.....G
           *   *      ** **      * **    *  **    * **  *  *   * **             *

EC3  T  TKKEFQATVKEG.VTGVIV.NL.TVG..DRDD.PATGAWRAVYTIINGN...P.GQSFEIHTNPQTNE.G
     N  TAMTFYGEVPEN.RVDVIVANL.TVT..DKDQ.PHTPAWNARYQMTGGD...PTGQ.FTILTDPNSND.G
     L  NPTMYEGVVEEN.KPGTEVARL.TVT..DQDA.PGSPAWQAVYHLKSGN...LDGA.FSIITDPSTNN.G
     E  NPSTYQGQVPEN.EVNARIATL.KVT..DDDA.PNTPAWKVVYTVV.ND...PDQQ.FVVVTDPTTND.G
     P  EPQKYEAWVPEN.EVGHEVQRL.TVT..DLDV.PNWPAWRATYHLVGGD...DGDH.FTITTHPETNQ.G
           * *        *  *   * * ** *     *  **      *        * ***   *

EC4  T  HPNPMTVTKQENIPIGSIVL...TVNATDPDTLQHQT...IRYSVYKD....PASWLEI...NPTN...G
     N  VPNPKLVRQEEGLLAGSMLT...TFTARDPDRYMQQT..SLRYSKLSD....PANWLKI...DPVN...G
     L  VPPIKRVGVPEDLPVGQQYT...SYTAEDPDRDMRQ...KITYRMGSD....PAGWLYI...HPEN...G
     E  MPAERRVEVPEDFGVGQEIT...SYTAREPDTFMDQ...KITYRIWRD....TANWLEI...NPET...G
     P  VPPSKVIEAQEGISIGELVC...IYTAQDPDKE.DQ...KISYTISRD....PANWLAV...DPDS...G
                * **      *       *                   *  **         *

EC5  T  SLYPTLAKVCDDAKDLRVV....VLGASDKDLHPNTDPFKFELSKQSGPE..KL.W..RINKLN..NTHA
     N  QVNPKEATTCETLQPNAIN.....ITAVDPDIDPNAGPFAFELPD.SPPSI.KRNW..TIVRIS..GDHA
     L  TPEPRSFEICSR.QPEKQI.....LSIVDKDLPPHTYPFKAALEH.GSS....NNW..TVEIRG..QDEL
     E  IPEPRNMQFCQR.NPQPHI.....ITILDPDLPPNTSPFTAELTH.GAS....VNW..TIEYNDAAQESL
     P  IPEPRQIIICNQ.SPVPQV....LNITDKDLSPNSSPFQAQLTH.DS.DI...YW..MAEVSE.KCDTV
         *  *           *  *        *** *    *      *

TM   T  .......ALHISMTLILLSLFSLFCL*
     N  ..IVGAGLGTGAIIAILLCIIILLILVLMFVVWM
     L  ..IVG.GLGVPAILGILGGILALLLLLLLLLFA
     E  AGIVAAGLQVPAILGILGGILALLLLLLLLLFL
     P  ....G.GFILP.ILGAV...LALLTLLLALLLLV
                                  * *

CP   T
     N  KRRDKERQAKQLLIDPEDDVRDNILKYDEEGGGEEDQDYDLSQLQ.QPDTVEPDAIKPVGIRRLDERP.IHAEPQYPVRSAAP
     L  RRRKVEKEP..LLP.PEDDMRDNVYNYDEEGGGEEDQDYDLSQLHRGLDAR.PEVI......RNDVAPPLMAAPQYRPRPA..
     E  RRRTVVKEP..LLP.PDDDTRDNVYYYDEEGGGEEDQDFDLSQLHRGLDAR.PEVT......RNDVAPTLMSVPQYRPRPA..
     P  RKKKRKVKEP..LLL.PEDDTRDNVFYGEEGGGEEDQDYDITQLHRGLEAR.PEVVL.....RNDVVPTFIPTPMYRPRPA..

T
     N  HPGDIGDFINEGLKAADNDPTAPPYDSLLVFDYEGSGSTAGSLSSLNSSSSGGEQDYDYLNDWGPRFKKLADMYGGG..DD*
     L  NPDEIGNFIDENLKAADTDPTAPPYDSLLVFDYEGGGSEATSLSSLNSSASDQDQDYDYLNEWGNRFKKLAELYGGGEDDE*
     E  NPDEIGNFIDENLKAADSDPTAPPYDSLLVFDYEGSGSEAASLSSLNSSESDQDQDYDYLNEWGNRFKKLADMYGGGEDD*
     P  NPDEIGNFIIENLKAANTDPTAPPYDSLMVFDYEGSGSDAASLSSLTTSASDQDQDYNYLNEWGSRFKKLADMYGGGEDD*
```

FIG.3A

```
KNVSEAGRALF..VHAR..SEHAE...DMAEILI.VGADEKHDALKEIFKIEGNLGIP..........RQKR
SFQLSAEPTEFVVSARDKETQEEWQMKVKLT.PEPAFTGASEKDQKKIEDIIFPWQQYKDSSHLKRQKR
PLTLYGRKISFTIYAQDAMGKR.HSARVTV..GRHRHRRHHHNHHLQDTTPAVLTFPKHDPGFLRRQKR
HLKLHKLETSFLVRARDSSHRE..LSTKVTLKSMGHHHHRHHHRDPASESNPELLMFPSVYPG.LRRQKR
.............................MHHADNGDIIMLTRGTVQGGKDAMHSPPTRILRRRKR
                                                            *  **

DVSVTRP...LDRE.....AIANYELEVEVTDLSGKIIDG.........PVRLDISVIDQNDNRPMF
QLSVTKP...LDRE.....QIASFHLRAHAVDVNGNQVEN.........PIDIVINVIDMNDNRPEF
WLEVTEQ...LDRE.....KIDRYTLLSHAVSASGQPVED.........PMEIIITVMDQNDNKPVF
WLKVTQP...LDRE.....AIAKYILYSHAVSSNGEAVED.........PMEIVITVTDQNDNRPEF
WLLLHMP...LDRE.....KIVKYELYGHAVSENGASVEE.........PMNISIIVTDQNDNKPKF
          ****        *     *     *              *   * * ** * *

DIVTVVSPVLLDRE...TMETPKYELVIEAKDMGGHDV..GLTG.....TATATILIDDKNDHPPEF
DIITVAAG..LDRE....KVQQYTLIIQATDMEGNPTY.GLSN.....TATAVITVTDVNDNPPEF
IISVLGTG..LDRE....TTPNYTLIVQATDQEGK....GLSN.....TATAIIEVTDANDNIPIF
VISVLTSG..LDRE....SYPTYTLVVQAADLQGE....GLST.....TAKAVITVKDINDNAPVF
TISVISSG..LDRE....KVPEYRLTVQATDMDGE....GSTT.....TAEAVVQILDANDNAPEF
*         ****         *  *   *   *            ** *  * **   * *

.MLSVVKP..LDYE.....ISAFHTLLI.KVE.NEDPLIPDIAYGPSS.TATVQITVEDVNE..GPVF
.LVTVVKP..IDFE.....TNRMFVLTV.AAE..NQVPLAKGIQHPPQS.TATVSITVIDVNE..SPYF
ILKTA.KG..LDYE.....TKSRYDLVV.TVE..NKVPLS.VPITLS...TASVLVTVLDVNE..PPVF
ILKTA.KG..LDFE.....AKQQYILHV.RVE..NEEPFE.GSLVPS...TATVTVDVVDVNE..APIF
VLTTK.KG..LDFE.....AQDQHTLYV.EVT..NEAPFA.VKLPTA...TATVVVHVKDVNE..APVF
   *  *   *  *         *    *    *              ** *  * **** * *

TVATTAV...LDRESP.HVQDNKYTALFLAID.SGNPPATG.......TGTLHITLEDVNDNVP
QITTTAV...LDRESI.YVQNNMYNATFLASD.NGIPPMSG.......TGTLQIYLLDINDNAP
.IVTATQP..LDRESV.HAINSTYKAIILAVD.NGIPDTTG.......TGTLLLLLQDVNDNGP
AIFTRAE...MDREDAEHVKNSTYVALIIATD.DGSPIATG.......TGTLLLVLLDVNDNAP
QI.TAAGI..LDREDEQFVKNNVYEVMVLATD.SGNPPTTG.......TGTLLLTLTDINDHGP
   *      ***       *    * ** *   *            ****  * ** *

QVVL..LQNLKKAN.......YNIPISVTD.SGKPPLTNNTELKLQVCSCK.KSRMDCSASD.
QLSL..RIRFLEAGI......YDVPIVITD.SGNPHASSTSVLKVKVCQCD.ING.DCTDVDR
AMGL...KKELEPGE......YNIFVKLTD.SQGK.AQVTQV.KAQVCECEGTAKN.CERRSY
ILQP...RKDLEIGE......YKIHLKLAD.NQNKD.QVT.TLDVHVCDCEGTVNN.CMK...
ALSL...KKFLKQDT......YDLHLSLSD.HGNRE.QLT.MIRATVCDCHGQVFNDCPRPWK
              *      *     *         ** *      *
```

FIG.3B

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3959 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 45..2181

( x i ) SEQUENCE DESCRIPTION: SEQ ID NO:1:

```
GAATTCCGAA TGAAAAGCC TCTGGTACGT TCTAGTCTGG CAAA ATG CAG CAC AAA                56
                                                Met Gln His Lys
                                                 1

ACT CAA CTT ACT CTG TCC TTT CTG CTG TCC CAG GTT CTG TTG CTT GCG               104
Thr Gln Leu Thr Leu Ser Phe Leu Leu Ser Gln Val Leu Leu Leu Ala
 5               10                  15                  20

TGT GCA GAA GAT TTA GAA TGC ACC CCT GGA TTC CAG CAA AAG GTT TTT               152
Cys Ala Glu Asp Leu Glu Cys Thr Pro Gly Phe Gln Gln Lys Val Phe
             25                  30                  35

TAT ATT GAA CAG CCA TTT GAA TTC ACA GAG GAC CAG CCA ATT CTG AAC               200
Tyr Ile Glu Gln Pro Phe Glu Phe Thr Glu Asp Gln Pro Ile Leu Asn
         40                  45                  50

CTG GTG TTT GAT GAC TGC AAG GGG AAT AAC AAA TTG AAC TTC GAA GTT               248
Leu Val Phe Asp Asp Cys Lys Gly Asn Asn Lys Leu Asn Phe Glu Val
     55                  60                  65

TCT AAC CCA GAC TTT AAG GTG GAA CAC GAT GGA TCT TTA GTT GCA CTG               296
Ser Asn Pro Asp Phe Lys Val Glu His Asp Gly Ser Leu Val Ala Leu
 70                  75                  80

AAG AAT GTA TCA GAA GCT GGC AGA GCT TTG TTT GTC CAT GCA CGG TCT               344
Lys Asn Val Ser Glu Ala Gly Arg Ala Leu Phe Val His Ala Arg Ser
 85                  90                  95                 100

GAG CAT GCT GAG GAT ATG GCA GAA ATT TTG ATT GTT GGA GCT GAT GAG               392
Glu His Ala Glu Asp Met Ala Glu Ile Leu Ile Val Gly Ala Asp Glu
             105                 110                 115

AAG CAC GAT GCA TTA AAG GAA ATC TTT AAG ATA GAA GGC AAC CTT GGA               440
Lys His Asp Ala Leu Lys Glu Ile Phe Lys Ile Glu Gly Asn Leu Gly
             120                 125                 130

ATT CCA AGA CAA AAA AGG GCT ATT CTG GCG ACT CCA ATA TTA ATT CCA               488
Ile Pro Arg Gln Lys Arg Ala Ile Leu Ala Thr Pro Ile Leu Ile Pro
         135                 140                 145

GAA AAT CAA AGA CCA CCA TTT CCC AGA TCA GTT GGC AAG GTC ATC AGG               536
Glu Asn Gln Arg Pro Pro Phe Pro Arg Ser Val Gly Lys Val Ile Arg
 150                 155                 160

AGT GAA GGG ACA GAG GGA GCA AAG TTC CGA CTC TCT GGT AAG GGA GTA               584
Ser Glu Gly Thr Glu Gly Ala Lys Phe Arg Leu Ser Gly Lys Gly Val
 165                 170                 175                 180

GAT CAA GAC CCG AAA GGA ATT TTT AGA ATC AAT GAG ATC AGT GGG GAT               632
Asp Gln Asp Pro Lys Gly Ile Phe Arg Ile Asn Glu Ile Ser Gly Asp
             185                 190                 195

GTC TCT GTG ACC CGA CCC CTG GAT AGA GAA GCA ATA GCC AAT TAT GAG               680
Val Ser Val Thr Arg Pro Leu Asp Arg Glu Ala Ile Ala Asn Tyr Glu
             200                 205                 210

CTG GAA GTT GAA GTA ACG GAT TTA AGT GGG AAA ATC ATT GAT GGC CCA               728
Leu Glu Val Glu Val Thr Asp Leu Ser Gly Lys Ile Ile Asp Gly Pro
             215                 220                 225

GTC CGC TTA GAT ATT TCT GTT ATT GAT CAA AAT GAT AAC AGG CCG ATG               776
Val Arg Leu Asp Ile Ser Val Ile Asp Gln Asn Asp Asn Arg Pro Met
         230                 235                 240
```

| | | | | | | | | | | | | | | | | |
|---|---|---|---|---|---|---|---|---|---|---|---|---|---|---|---|---|
| TTC | AAA | GAA | GGA | CCC | TAT | GTT | GGT | CAC | GTC | ATG | GAA | GGA | TCC | CCT | ACA | 824 |
| Phe | Lys | Glu | Gly | Pro | Tyr | Val | Gly | His | Val | Met | Glu | Gly | Ser | Pro | Thr | |
| 245 | | | | 250 | | | | | 255 | | | | | 260 | | |
| GGA | ACA | ACT | GTG | ATG | CGG | ATG | ACA | GCA | TTT | GAT | GCT | GAT | GAT | CCT | AGC | 872 |
| Gly | Thr | Thr | Val | Met | Arg | Met | Thr | Ala | Phe | Asp | Ala | Asp | Asp | Pro | Ser | |
| | | | | 265 | | | | 270 | | | | | 275 | | | |
| ACA | GAC | AAC | GCT | CTT | CTG | CGG | TAT | AAC | ATC | CTC | AAG | CAG | ACA | CCT | ACC | 920 |
| Thr | Asp | Asn | Ala | Leu | Leu | Arg | Tyr | Asn | Ile | Leu | Lys | Gln | Thr | Pro | Thr | |
| | | | 280 | | | | 285 | | | | | 290 | | | | |
| AAA | CCT | TCC | CCA | AAT | ATG | TTC | TAC | ATT | GAC | CCA | GAA | AAG | GGA | GAT | ATT | 968 |
| Lys | Pro | Ser | Pro | Asn | Met | Phe | Tyr | Ile | Asp | Pro | Glu | Lys | Gly | Asp | Ile | |
| | | 295 | | | | 300 | | | | | 305 | | | | | |
| GTC | ACA | GTG | GTG | TCA | CCT | GTA | CTG | CTG | GAT | CGT | GAG | ACA | ATG | GAA | ACG | 1016 |
| Val | Thr | Val | Val | Ser | Pro | Val | Leu | Leu | Asp | Arg | Glu | Thr | Met | Glu | Thr | |
| | 310 | | | | 315 | | | | | 320 | | | | | | |
| CCG | AAG | TAC | GAG | CTG | GTT | ATT | GAA | GCC | AAG | GAT | ATG | GGC | GGC | CAT | GAT | 1064 |
| Pro | Lys | Tyr | Glu | Leu | Val | Ile | Glu | Ala | Lys | Asp | Met | Gly | Gly | His | Asp | |
| 325 | | | | | 330 | | | | 335 | | | | | 340 | | |
| GTG | GGA | CTT | ACT | GGA | ACT | GCA | ACT | GCC | ACT | ATT | CTT | ATT | GAT | GAC | AAA | 1112 |
| Val | Gly | Leu | Thr | Gly | Thr | Ala | Thr | Ala | Thr | Ile | Leu | Ile | Asp | Asp | Lys | |
| | | | | 345 | | | | 350 | | | | | 355 | | | |
| AAC | GAC | CAC | CCA | CCA | GAA | TTT | ACC | AAG | AAG | GAG | TTT | CAG | GCC | ACA | GTA | 1160 |
| Asn | Asp | His | Pro | Pro | Glu | Phe | Thr | Lys | Lys | Glu | Phe | Gln | Ala | Thr | Val | |
| | | | 360 | | | | 365 | | | | | 370 | | | | |
| AAG | GAA | GGA | GTC | ACA | GGA | GTA | ATA | GTA | AAC | TTA | ACT | GTT | GGT | GAC | CGA | 1208 |
| Lys | Glu | Gly | Val | Thr | Gly | Val | Ile | Val | Asn | Leu | Thr | Val | Gly | Asp | Arg | |
| | | 375 | | | | 380 | | | | | 385 | | | | | |
| GAT | GAC | CCA | GCA | ACT | GGA | GCA | TGG | AGA | GCT | GTC | TAC | ACT | ATT | ATT | AAC | 1256 |
| Asp | Asp | Pro | Ala | Thr | Gly | Ala | Trp | Arg | Ala | Val | Tyr | Thr | Ile | Ile | Asn | |
| | 390 | | | | 395 | | | | | 400 | | | | | | |
| GGA | AAT | CCA | GGG | CAG | AGT | TTT | GAA | ATC | CAT | ACC | AAT | CCC | CAG | ACT | AAT | 1304 |
| Gly | Asn | Pro | Gly | Gln | Ser | Phe | Glu | Ile | His | Thr | Asn | Pro | Gln | Thr | Asn | |
| 405 | | | | 410 | | | | 415 | | | | | 420 | | | |
| GAG | GGA | ATG | CTC | TCT | GTT | GTC | AAA | CCT | TTA | GAC | TAT | GAG | ATT | TCA | GCA | 1352 |
| Glu | Gly | Met | Leu | Ser | Val | Val | Lys | Pro | Leu | Asp | Tyr | Glu | Ile | Ser | Ala | |
| | | | | 425 | | | | 430 | | | | | 435 | | | |
| TTT | CAC | ACA | TTG | CTG | ATA | AAA | GTA | GAA | AAT | GAA | GAC | CCG | TTG | ATT | CCA | 1400 |
| Phe | His | Thr | Leu | Leu | Ile | Lys | Val | Glu | Asn | Glu | Asp | Pro | Leu | Ile | Pro | |
| | | | 440 | | | | 445 | | | | | 450 | | | | |
| GAC | ATA | GCC | TAC | GGT | CCC | AGT | TCC | ACA | GCA | ACA | GTT | CAG | ATC | ACC | GTT | 1448 |
| Asp | Ile | Ala | Tyr | Gly | Pro | Ser | Ser | Thr | Ala | Thr | Val | Gln | Ile | Thr | Val | |
| | | 455 | | | | 460 | | | | | 465 | | | | | |
| GAG | GAT | GTG | AAT | GAA | GGC | CCT | GTT | TTC | CAC | CCA | AAC | CCA | ATG | ACA | GTG | 1496 |
| Glu | Asp | Val | Asn | Glu | Gly | Pro | Val | Phe | His | Pro | Asn | Pro | Met | Thr | Val | |
| | 470 | | | | 475 | | | | | 480 | | | | | | |
| ACA | AAA | CAA | GAG | AAC | ATC | CCT | ATT | GGC | AGC | ATT | GTG | TTA | ACA | GTA | AAT | 1544 |
| Thr | Lys | Gln | Glu | Asn | Ile | Pro | Ile | Gly | Ser | Ile | Val | Leu | Thr | Val | Asn | |
| 485 | | | | 490 | | | | 495 | | | | | 500 | | | |
| GCC | ACT | GAT | CCA | GAT | ACT | TTG | CAA | CAT | CAG | ACT | ATC | AGG | TAT | TCA | GTT | 1592 |
| Ala | Thr | Asp | Pro | Asp | Thr | Leu | Gln | His | Gln | Thr | Ile | Arg | Tyr | Ser | Val | |
| | | | 505 | | | | 510 | | | | | 515 | | | | |
| TAC | AAG | GAT | CCA | GCA | AGC | TGG | CTA | GAG | ATT | AAT | CCC | ACC | AAT | GGT | ACC | 1640 |
| Tyr | Lys | Asp | Pro | Ala | Ser | Trp | Leu | Glu | Ile | Asn | Pro | Thr | Asn | Gly | Thr | |
| | | 520 | | | | 525 | | | | | 530 | | | | | |
| GTT | GCC | ACC | ACT | GCT | GTC | CTG | GAT | CGG | GAA | TCT | CCT | CAT | GTT | CAG | GAT | 1688 |
| Val | Ala | Thr | Thr | Ala | Val | Leu | Asp | Arg | Glu | Ser | Pro | His | Val | Gln | Asp | |
| | 535 | | | | 540 | | | | | 545 | | | | | | |
| AAC | AAA | TAC | ACT | GCT | CTC | TTC | CTG | GCA | ATA | GAC | AGT | GGT | AAC | CCT | CCT | 1736 |
| Asn | Lys | Tyr | Thr | Ala | Leu | Phe | Leu | Ala | Ile | Asp | Ser | Gly | Asn | Pro | Pro | |
| 550 | | | | 555 | | | | 560 | | | | | | | | |

-continued

| | | | | | | | | | | | | | | | | |
|---|---|---|---|---|---|---|---|---|---|---|---|---|---|---|---|---|
| GCT | ACA | GGT | ACA | GGA | ACT | TTA | CAC | ATC | ACC | TTG | GAG | GAC | GTC | AAT | GAC | 1784 |
| Ala | Thr | Gly | Thr | Gly | Thr | Leu | His | Ile | Thr | Leu | Glu | Asp | Val | Asn | Asp | |
| 565 | | | | 570 | | | | | 575 | | | | | 580 | | |
| AAT | GTC | CCC | TCC | CTT | TAC | CCA | ACA | CTG | GCA | AAA | GTC | TGT | GAT | GAT | GCT | 1832 |
| Asn | Val | Pro | Ser | Leu | Tyr | Pro | Thr | Leu | Ala | Lys | Val | Cys | Asp | Asp | Ala | |
| | | | | 585 | | | | | 590 | | | | | 595 | | |
| AAA | GAT | CTC | AGA | GTA | GTG | GTA | CTA | GGA | GCA | TCA | GAC | AAA | GAC | CTC | CAT | 1880 |
| Lys | Asp | Leu | Arg | Val | Val | Val | Leu | Gly | Ala | Ser | Asp | Lys | Asp | Leu | His | |
| | | | 600 | | | | | 605 | | | | | 610 | | | |
| CCC | AAC | ACA | GAT | CCA | TTT | AAA | TTT | GAA | CTG | AGT | AAG | CAA | TCT | GGT | CCA | 1928 |
| Pro | Asn | Thr | Asp | Pro | Phe | Lys | Phe | Glu | Leu | Ser | Lys | Gln | Ser | Gly | Pro | |
| | | 615 | | | | | 620 | | | | | 625 | | | | |
| GAA | AAG | TTA | TGG | AGA | ATC | AAC | AAG | CTT | AAC | AAT | ACT | CAT | GCC | CAG | GTT | 1976 |
| Glu | Lys | Leu | Trp | Arg | Ile | Asn | Lys | Leu | Asn | Asn | Thr | His | Ala | Gln | Val | |
| | 630 | | | | | 635 | | | | | 640 | | | | | |
| GTC | CTG | CTT | CAA | AAC | CTG | AAA | AAG | GCC | AAT | TAC | AAC | ATC | CCA | ATC | TCA | 2024 |
| Val | Leu | Leu | Gln | Asn | Leu | Lys | Lys | Ala | Asn | Tyr | Asn | Ile | Pro | Ile | Ser | |
| 645 | | | | | 650 | | | | | 655 | | | | | 660 | |
| GTG | ACA | GAT | TCT | GGA | AAA | CCA | CCT | CTG | ACT | AAC | AAC | ACA | GAA | CTG | AAA | 2072 |
| Val | Thr | Asp | Ser | Gly | Lys | Pro | Pro | Leu | Thr | Asn | Asn | Thr | Glu | Leu | Lys | |
| | | | | 665 | | | | | 670 | | | | | 675 | | |
| TTA | CAA | GTG | TGT | TCC | TGC | AAG | AAA | TCC | AGA | ATG | GAC | TGC | AGT | GCA | AGT | 2120 |
| Leu | Gln | Val | Cys | Ser | Cys | Lys | Lys | Ser | Arg | Met | Asp | Cys | Ser | Ala | Ser | |
| | | | 680 | | | | | 685 | | | | | 690 | | | |
| GAT | GCC | CTT | CAT | ATC | AGC | ATG | ACT | CTT | ATC | CTT | CTT | TCA | CTC | TTC | AGT | 2168 |
| Asp | Ala | Leu | His | Ile | Ser | Met | Thr | Leu | Ile | Leu | Leu | Ser | Leu | Phe | Ser | |
| | | 695 | | | | | 700 | | | | | 705 | | | | |
| TTA | TTT | TGT | CTG | T | AGGAACTCCT | | DACATTTGAA | | GCTGTCCTAC | | CGAGTTGCCA | | | | | 2221 |
| Leu | Phe | Cys | Leu | | | | | | | | | | | | | |
| | 710 | | | | | | | | | | | | | | | |

| | | | | | |
|---|---|---|---|---|---|
| TGGCAACGAG | AAAAAAGAAA | ACGTCAGATC | TGAAGACTGC | AGTTTACAGT | TACTGTTCTT | 2281 |
| CACTACTAGG | CCTCAGTTGC | TCCAGATTCA | GTTTAATTTG | CAACCTCACT | TAATCTGTCC | 2341 |
| GACTATACAT | TGGTGTTTGA | CAGCCTCTGC | CCTAACTTCC | ATTTATTAAT | GGATTCCTCT | 2401 |
| TGCAAGATGC | AAGGTTTATG | CGAATTTTCA | CTGAATGTTA | AAAGACCATG | ACATCTAAAC | 2461 |
| TTGACCTTTG | GGGAGCAGAA | AACAGATTGA | CTCCATTTTT | TTCTAACTGT | TGACTTGTTG | 2521 |
| CTATTCAACT | GTTCAGAAAA | TATTTTGTCT | GTGGGTTAGT | ATTTGTATAT | GTATGAGTGT | 2581 |
| ATGTATATAT | ATATATATTT | ATATGGAGAG | AAGAGTTATA | GGACTGGTTT | AGCTTTTATA | 2641 |
| AAATATTCAT | CTGGAATGTG | CAAATGACAA | AGCAGAGTAA | TACAGCCACA | GATGAATCAT | 2701 |
| AACTATTCAA | CATGGCTAAA | CCTACTGTAC | TTGCTGTTTA | TAGTGTGGCC | AGAAGGAGAG | 2761 |
| CCTATTGCAG | TCATACCACT | GAAAAAGCC | ACTTTGTTGA | CACCAAATAA | GGCAGGCCCA | 2821 |
| GGGCTCTGCA | GCATCACTTC | TTGTACCTCA | GGTTCAGCAA | ACAGGAAATG | CAAGTCCCCC | 2881 |
| GGCTTGCTTC | TGATCCGGAC | TTCTCACCTT | ATGCCCAAA | ACTGACTTTA | AGACTCAGCG | 2941 |
| GGAGCACATC | TCTTCATCTC | AGTGCCGGGA | GGGTACGCAA | GCTCTCACCT | GTAAGGCAAG | 3001 |
| GGAAGCACT | CAGCACAGCC | AGCACCATAT | GGTCACCACC | TACAGCAATG | GGACCTGCTG | 3061 |
| GGCTGATTTT | AAAGGGGCTA | AACTCAGCTT | CCTCTATGCT | CTTGCAGATA | ATTATTTGCT | 3121 |
| GGGGCAGTTT | ACAAAATTTA | AGTCCTTTGT | CAGTTCTGCA | GACGAAGTAG | GTAATGTCTG | 3181 |
| CTTATGAGAA | GCTGATTAGA | ACAGCAAAAT | CAAGGTGTTT | CCCAGAAGCA | CTGGCCTCTC | 3241 |
| TCTCAGCCTC | TGTGCAGCTG | TCATTACATG | TATCAGTGCA | AGGAGGAAAA | CAGATGCCCT | 3301 |
| ATTATCTAAG | TGTATTCACA | CATATCTATA | GTTTTGAATA | TATATATACA | TACATACACG | 3361 |
| TGTACACACA | GTTTCCAGTT | AAGAGTAACA | AGAGCATTTC | TTTGTGTGTG | TAAACTTACC | 3421 |

| | | | | | |
|---|---|---|---|---|---|
|ACACTTGTTT|GCAGACATGG|GGAAAAAAAG|GGTGTTCGTT|ACATATGACT|ATGAATCCTT 3481|
|TTTTATTCTG|TGAGCATGTA|AGGTTTAAAA|AAGAAAAAAC|TTAACTGTAT|CAAGATGATC 3541|
|ATCTTGTTAA|TAAATTGTAA|ATGATCCATC|AAAGCTCACA|CCAAATTTTT|ATAAAATTAA 3601|
|CACAGAAAAG|TATACTAGTG|ACAGACTGTG|GCTTTTATTA|GAGCTTGCCA|GTAACTAGGG 3661|
|TAAGGTAAGT|GTCTTAGAAT|ATTTTAATAA|ACTTGCTTAT|TTAAAGTTTA|AACAAGAAAG 3721|
|CTTCCTTATG|CAATAGTACT|TTGCAGCTGC|ATTCTTTAGT|TAGCATTTTT|ACAGTACCTA 3781|
|TGAGTCATAC|TGTATGTTGT|CTTTACTACA|GTGAGATTAT|GAGCATATCT|TCCACACCAC 3841|
|ATATATGTTT|CAATAGTAAA|GTTTTTTGGA|AGCATTAAAG|AGTCCAAACA|TACACTGAGT 3901|
|TTTCCATAAC|GCTACACTAG|ATATTAAATG|TGTGTTGGTG|GTTAAAAAAA|AAAAAAA 3959|

( 2 ) INFORMATION FOR SEQ ID NO:2:

( i ) SEQUENCE CHARACTERISTICS:
( A ) LENGTH: 712 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Gln His Lys Thr Gln Leu Thr Leu Ser Phe Leu Leu Ser Gln Val
 1               5                  10                 15
Leu Leu Leu Ala Cys Ala Glu Asp Leu Glu Cys Thr Pro Gly Phe Gln
                20                 25                  30
Gln Lys Val Phe Tyr Ile Glu Gln Pro Phe Glu Phe Thr Glu Asp Gln
            35                  40                  45
Pro Ile Leu Asn Leu Val Phe Asp Asp Cys Lys Gly Asn Asn Lys Leu
        50                  55                  60
Asn Phe Glu Val Ser Asn Pro Asp Phe Lys Val Glu His Asp Gly Ser
 65                 70                  75                  80
Leu Val Ala Leu Lys Asn Val Ser Glu Ala Gly Arg Ala Leu Phe Val
                85                  90                  95
His Ala Arg Ser Glu His Ala Glu Asp Met Ala Glu Ile Leu Ile Val
               100                 105                 110
Gly Ala Asp Glu Lys His Asp Ala Leu Lys Glu Ile Phe Lys Ile Glu
           115                 120                 125
Gly Asn Leu Gly Ile Pro Arg Gln Lys Arg Ala Ile Leu Ala Thr Pro
       130                 135                 140
Ile Leu Ile Pro Glu Asn Gln Arg Pro Pro Phe Pro Arg Ser Val Gly
145                 150                 155                 160
Lys Val Ile Arg Ser Glu Gly Thr Glu Gly Ala Lys Phe Arg Leu Ser
               165                 170                 175
Gly Lys Gly Val Asp Gln Asp Pro Lys Gly Ile Phe Arg Ile Asn Glu
           180                 185                 190
Ile Ser Gly Asp Val Ser Val Thr Arg Pro Leu Asp Arg Glu Ala Ile
       195                 200                 205
Ala Asn Tyr Glu Leu Glu Val Glu Val Thr Asp Leu Ser Gly Lys Ile
   210                 215                 220
Ile Asp Gly Pro Val Arg Leu Asp Ile Ser Val Ile Asp Gln Asn Asp
225                 230                 235                 240
Asn Arg Pro Met Phe Lys Glu Gly Pro Tyr Val Gly His Val Met Glu
               245                 250                 255
Gly Ser Pro Thr Gly Thr Thr Val Met Arg Met Thr Ala Phe Asp Ala
           260                 265                 270
```

```
Asp  Asp  Pro  Ser  Thr  Asp  Asn  Ala  Leu  Leu  Arg  Tyr  Asn  Ile  Leu  Lys
          275                 280                     285

Gln  Thr  Pro  Thr  Lys  Pro  Ser  Pro  Asn  Met  Phe  Tyr  Ile  Asp  Pro  Glu
     290                 295                      300

Lys  Gly  Asp  Ile  Val  Thr  Val  Val  Ser  Pro  Val  Leu  Leu  Asp  Arg  Glu
305                      310                 315                           320

Thr  Met  Glu  Thr  Pro  Lys  Tyr  Glu  Leu  Val  Ile  Glu  Ala  Lys  Asp  Met
               325                      330                          335

Gly  Gly  His  Asp  Val  Gly  Leu  Thr  Gly  Thr  Ala  Thr  Ala  Thr  Ile  Leu
               340                 345                          350

Ile  Asp  Asp  Lys  Asn  Asp  His  Pro  Pro  Glu  Phe  Thr  Lys  Lys  Glu  Phe
          355                 360                      365

Gln  Ala  Thr  Val  Lys  Glu  Gly  Val  Thr  Gly  Val  Ile  Val  Asn  Leu  Thr
     370                 375                      380

Val  Gly  Asp  Arg  Asp  Pro  Ala  Thr  Gly  Ala  Trp  Arg  Ala  Val  Tyr
385                      390                 395                           400

Thr  Ile  Ile  Asn  Gly  Asn  Pro  Gly  Gln  Ser  Phe  Glu  Ile  His  Thr  Asn
                    405                 410                      415

Pro  Gln  Thr  Asn  Glu  Gly  Met  Leu  Ser  Val  Val  Lys  Pro  Leu  Asp  Tyr
               420                      425                 430

Glu  Ile  Ser  Ala  Phe  His  Thr  Leu  Ile  Lys  Val  Glu  Asn  Glu  Asp
          435                      440                      445

Pro  Leu  Ile  Pro  Asp  Ile  Ala  Tyr  Gly  Pro  Ser  Ser  Thr  Ala  Thr  Val
     450                      455                 460

Gln  Ile  Thr  Val  Glu  Asp  Val  Asn  Glu  Gly  Pro  Val  Phe  His  Pro  Asn
465                      470                 475                           480

Pro  Met  Thr  Val  Thr  Lys  Gln  Glu  Asn  Ile  Pro  Ile  Gly  Ser  Ile  Val
                    485                      490                      495

Leu  Thr  Val  Asn  Ala  Thr  Asp  Pro  Asp  Thr  Leu  Gln  His  Gln  Thr  Ile
               500                      505                      510

Arg  Tyr  Ser  Val  Tyr  Lys  Asp  Pro  Ala  Ser  Trp  Leu  Glu  Ile  Asn  Pro
          515                      520                      525

Thr  Asn  Gly  Thr  Val  Ala  Thr  Ala  Val  Leu  Asp  Arg  Glu  Ser  Pro
     530                      535                      540

His  Val  Gln  Asp  Asn  Lys  Tyr  Thr  Ala  Leu  Phe  Leu  Ala  Ile  Asp  Ser
545                           550                     555                      560

Gly  Asn  Pro  Pro  Ala  Thr  Gly  Thr  Gly  Thr  Leu  His  Ile  Thr  Leu  Glu
                    565                 570                          575

Asp  Val  Asn  Asp  Asn  Val  Pro  Ser  Leu  Tyr  Pro  Thr  Leu  Ala  Lys  Val
               580                     585                          590

Cys  Asp  Asp  Ala  Lys  Asp  Leu  Arg  Val  Val  Val  Leu  Gly  Ala  Ser  Asp
          595                      600                      605

Lys  Asp  Leu  His  Pro  Asn  Thr  Asp  Pro  Phe  Lys  Phe  Glu  Leu  Ser  Lys
     610                      615                 620

Gln  Ser  Gly  Pro  Glu  Lys  Leu  Trp  Arg  Ile  Asn  Lys  Leu  Asn  Asn  Thr
625                      630                      635                           640

His  Ala  Gln  Val  Val  Leu  Leu  Gln  Asn  Leu  Lys  Lys  Ala  Asn  Tyr  Asn
                    645                      650                          655

Ile  Pro  Ile  Ser  Val  Thr  Asp  Ser  Gly  Lys  Pro  Pro  Leu  Thr  Asn  Asn
               660                      665                      670

Thr  Glu  Leu  Lys  Leu  Gln  Val  Cys  Ser  Cys  Lys  Lys  Ser  Arg  Met  Asp
               675                      680                      685

Cys  Ser  Ala  Ser  Asp  Ala  Leu  His  Ile  Ser  Met  Thr  Leu  Ile  Leu  Leu
```

```
                       690                          695                          700
Ser  Leu  Phe  Ser  Leu  Phe  Cys  Leu
705                      710
```

( 2 ) INFORMATION FOR SEQ ID NO:3:

( i ) SEQUENCE CHARACTERISTICS:
        ( A ) LENGTH: 2779 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 40..2191

( x i ) SEQUENCE DESCRIPTION: SEQ ID NO:3:

```
GAATTCCAAA  AAGCCTCTGG  TACGTTCTAG  TCTGGCAAA ATG CAG CAC AAA ACT              54
                                             Met Gln His Lys Thr
                                              1               5

CAA CTT ACT CTG TCC TTT CTG CTG TCC CAG GTT CTG TTG CTT GCG TGT              102
Gln Leu Thr Leu Ser Phe Leu Leu Ser Gln Val Leu Leu Leu Ala Cys
             10                  15                  20

GCA GAA GAT TTA GAA TGC ACC CCT GGA TTC CAG CAA AAG GTT TTT TAT              150
Ala Glu Asp Leu Glu Cys Thr Pro Gly Phe Gln Gln Lys Val Phe Tyr
                 25                  30                  35

ATT GAA CAG CCA TTT GAA TTC ACA GAG GAC CAG CCA ATT CTG AAC CTG              198
Ile Glu Gln Pro Phe Glu Phe Thr Glu Asp Gln Pro Ile Leu Asn Leu
             40                  45                  50

GTG TTT GAT GAC TGC AAG GGG AAT AAC AAA TTG AAC TTC GAA GTT TCT              246
Val Phe Asp Asp Cys Lys Gly Asn Asn Lys Leu Asn Phe Glu Val Ser
         55                  60                  65

AAC CCA GAC TTT AAG GTG GAA CAC GAT GGA TCT TTA GTT GCA CTG AAG              294
Asn Pro Asp Phe Lys Val Glu His Asp Gly Ser Leu Val Ala Leu Lys
 70              75                  80                      85

AAT GTA TCA GAA GCT GGC AGA GCT TTG TTT GTC CAT GCA CGG TCT GAG              342
Asn Val Ser Glu Ala Gly Arg Ala Leu Phe Val His Ala Arg Ser Glu
                 90                  95                 100

CAT GCT GAG GAT ATG GCA GAA ATT TTG ATT GTT GGA GCT GAT GAG AAG              390
His Ala Glu Asp Met Ala Glu Ile Leu Ile Val Gly Ala Asp Glu Lys
                105                 110                 115

CAC GAT GCA TTA AAG GAA ATC TTT AAG ATA GAA GGC AAC CTT GGA ATT              438
His Asp Ala Leu Lys Glu Ile Phe Lys Ile Glu Gly Asn Leu Gly Ile
             120                 125                 130

CCA AGA CAA AAA AGG GCT ATT CTG GCG ACT CCA ATA TTA ATT CCA GAA              486
Pro Arg Gln Lys Arg Ala Ile Leu Ala Thr Pro Ile Leu Ile Pro Glu
     135                 140                 145

AAT CAA AGA CCA CCA TTT CCC AGA TCA GTT GGC AAG GTC ATC AGG AGT              534
Asn Gln Arg Pro Pro Phe Pro Arg Ser Val Gly Lys Val Ile Arg Ser
150                 155                 160                 165

GAA GGG ACA GAG GGA GCA AAG TTC CGA CTC TCT GGT AAG GGA GTA GAT              582
Glu Gly Thr Glu Gly Ala Lys Phe Arg Leu Ser Gly Lys Gly Val Asp
                 170                 175                 180

CAA GAC CCG AAA GGA ATT TTT AGA ATC AAT GAG ATC AGT GGG GAT GTC              630
Gln Asp Pro Lys Gly Ile Phe Arg Ile Asn Glu Ile Ser Gly Asp Val
             185                 190                 195

TCT GTG ACC CGA CCC CTG GAT AGA GAA GCA ATA GCC AAT TAT GAG CTG              678
Ser Val Thr Arg Pro Leu Asp Arg Glu Ala Ile Ala Asn Tyr Glu Leu
         200                 205                 210

GAA GTT GAA GTA ACG GAT TTA AGT GGG AAA ATC ATT GAT GGC CCA GTC              726
Glu Val Glu Val Thr Asp Leu Ser Gly Lys Ile Ile Asp Gly Pro Val
     215                 220                 225
```

| | | | | | | | | | | | | | | | | |
|---|---|---|---|---|---|---|---|---|---|---|---|---|---|---|---|---|
| CGC | CTA | GAT | ATT | TCT | GTT | ATT | GAT | CAA | AAT | GAT | AAC | AGG | CCG | ATG | TTC | 774 |
| Arg | Leu | Asp | Ile | Ser | Val | Ile | Asp | Gln | Asn | Asp | Asn | Arg | Pro | Met | Phe | |
| 230 | | | | 235 | | | | | 240 | | | | | | 245 | |
| AAA | GAA | GGA | CCC | TAT | GTT | GGT | CAC | GTC | ATG | GAA | GGA | TCC | CCT | ACA | GGA | 822 |
| Lys | Glu | Gly | Pro | Tyr | Val | Gly | His | Val | Met | Glu | Gly | Ser | Pro | Thr | Gly | |
| | | | | 250 | | | | | 255 | | | | | 260 | | |
| ACA | ACT | GTG | ATG | CGG | ATG | ACA | GCA | TTT | GAT | GCT | GAT | GAT | CCT | AGC | ACA | 870 |
| Thr | Thr | Val | Met | Arg | Met | Thr | Ala | Phe | Asp | Ala | Asp | Asp | Pro | Ser | Thr | |
| | | | 265 | | | | | 270 | | | | | 275 | | | |
| GAC | AAC | GCT | CTT | CTG | CGG | TAT | AAC | ATC | CTC | AAG | CAG | ACA | CCT | ACC | AAA | 918 |
| Asp | Asn | Ala | Leu | Leu | Arg | Tyr | Asn | Ile | Leu | Lys | Gln | Thr | Pro | Thr | Lys | |
| | | 280 | | | | | 285 | | | | | 290 | | | | |
| CCT | TCC | CCA | AAT | ATG | TTC | TAC | ATT | GAC | CCA | GAA | AAG | GGA | GAT | ATT | GTC | 966 |
| Pro | Ser | Pro | Asn | Met | Phe | Tyr | Ile | Asp | Pro | Glu | Lys | Gly | Asp | Ile | Val | |
| | 295 | | | | | 300 | | | | | 305 | | | | | |
| ACA | GTG | GTG | TCG | CCT | GTA | CTG | CTG | GAT | CGT | GAG | ACA | ATG | GAA | ACG | CCG | 1014 |
| Thr | Val | Val | Ser | Pro | Val | Leu | Leu | Asp | Arg | Glu | Thr | Met | Glu | Thr | Pro | |
| 310 | | | | | 315 | | | | | 320 | | | | | 325 | |
| AAG | TAC | GAG | CTG | GTT | ATT | GAA | GCC | AAG | GAT | ATG | GGC | GGC | CAT | GAT | GTG | 1062 |
| Lys | Tyr | Glu | Leu | Val | Ile | Glu | Ala | Lys | Asp | Met | Gly | Gly | His | Asp | Val | |
| | | | | 330 | | | | | 335 | | | | | 340 | | |
| GGA | CTT | ACT | GGA | ACT | GCA | ACT | GCC | ACT | ATT | CTT | ATT | GAT | GAC | AAA | AAC | 1110 |
| Gly | Leu | Thr | Gly | Thr | Ala | Thr | Ala | Thr | Ile | Leu | Ile | Asp | Asp | Lys | Asn | |
| | | | 345 | | | | | 350 | | | | | 355 | | | |
| GAC | CAC | CCA | CCA | GAA | TTT | ACC | AAG | AAG | GAG | TTT | CAG | GCC | ACA | GTA | AAG | 1158 |
| Asp | His | Pro | Pro | Glu | Phe | Thr | Lys | Lys | Glu | Phe | Gln | Ala | Thr | Val | Lys | |
| | | 360 | | | | | 365 | | | | | 370 | | | | |
| GAA | GGA | GTC | ACA | GGA | GTA | ATA | GTA | AAC | TTA | ACT | GTT | GGT | GAC | CGA | GAT | 1206 |
| Glu | Gly | Val | Thr | Gly | Val | Ile | Val | Asn | Leu | Thr | Val | Gly | Asp | Arg | Asp | |
| | 375 | | | | | 380 | | | | | 385 | | | | | |
| GAC | CCA | GCA | ACT | GGA | GCA | TGG | AGA | GCT | GTC | TAC | ACT | ATT | ATT | AAC | GGA | 1254 |
| Asp | Pro | Ala | Thr | Gly | Ala | Trp | Arg | Ala | Val | Tyr | Thr | Ile | Ile | Asn | Gly | |
| 390 | | | | | 395 | | | | | 400 | | | | | 405 | |
| AAT | CCA | GGG | CAG | AGT | TTT | GAA | ATC | CAT | ACC | AAT | CCC | CAG | ACT | AAT | GAG | 1302 |
| Asn | Pro | Gly | Gln | Ser | Phe | Glu | Ile | His | Thr | Asn | Pro | Gln | Thr | Asn | Glu | |
| | | | | 410 | | | | | 415 | | | | | 420 | | |
| GGA | ATG | CTC | TCT | GTT | GTC | AAA | CCT | TTA | GAC | TAT | GAG | ATT | TCA | GCA | TTT | 1350 |
| Gly | Met | Leu | Ser | Val | Val | Lys | Pro | Leu | Asp | Tyr | Glu | Ile | Ser | Ala | Phe | |
| | | | 425 | | | | | 430 | | | | | 435 | | | |
| CAC | ACA | TTG | CTG | ATA | AAA | GTA | GAA | AAT | GAA | GAC | CCG | TTG | ATT | CCA | GAC | 1398 |
| His | Thr | Leu | Leu | Ile | Lys | Val | Glu | Asn | Glu | Asp | Pro | Leu | Ile | Pro | Asp | |
| | | 440 | | | | | 445 | | | | | 450 | | | | |
| ATA | GCC | TAC | GGT | CCC | AGT | TCC | ACA | GCA | ACA | GTT | CAG | ATC | ACC | GTT | GAG | 1446 |
| Ile | Ala | Tyr | Gly | Pro | Ser | Ser | Thr | Ala | Thr | Val | Gln | Ile | Thr | Val | Glu | |
| | 455 | | | | | 460 | | | | | 465 | | | | | |
| GAT | GTG | AAT | GAA | GGC | CCT | GTT | TTC | CAC | CCA | AAC | CCA | ATG | ACA | GTG | ACA | 1494 |
| Asp | Val | Asn | Glu | Gly | Pro | Val | Phe | His | Pro | Asn | Pro | Met | Thr | Val | Thr | |
| 470 | | | | | 475 | | | | | 480 | | | | | 485 | |
| AAA | CAA | GAG | AAC | ATC | CCT | ATT | GGC | AGC | ATT | GTG | TTA | ACA | GTA | AAT | GCC | 1542 |
| Lys | Gln | Glu | Asn | Ile | Pro | Ile | Gly | Ser | Ile | Val | Leu | Thr | Val | Asn | Ala | |
| | | | | 490 | | | | | 495 | | | | | 500 | | |
| ACT | GAT | CCA | GAT | ACT | TTG | CAA | CAT | CAG | ACT | ATC | AGG | TAT | TCA | GTT | TAC | 1590 |
| Thr | Asp | Pro | Asp | Thr | Leu | Gln | His | Gln | Thr | Ile | Arg | Tyr | Ser | Val | Tyr | |
| | | | 505 | | | | | 510 | | | | | 515 | | | |
| AAG | GAT | CCA | GCA | AGC | TGG | CTA | GAG | ATT | AAT | CCC | ACC | AAT | GGT | ACC | GTT | 1638 |
| Lys | Asp | Pro | Ala | Ser | Trp | Leu | Glu | Ile | Asn | Pro | Thr | Asn | Gly | Thr | Val | |
| | | 520 | | | | | 525 | | | | | 530 | | | | |
| GCC | ACC | ACT | GCT | GTC | CTG | GAT | CGG | GAA | TCT | CCG | CAT | GTT | CAG | GAT | AAC | 1686 |
| Ala | Thr | Thr | Ala | Val | Leu | Asp | Arg | Glu | Ser | Pro | His | Val | Gln | Asp | Asn | |
| | 535 | | | | | 540 | | | | | 545 | | | | | |

```
AAA  TAC  ACT  GCT  CTC  TTC  CTG  GCA  ATA  GAC  AGT  GGT  AAC  CCT  CCT  GCT    1734
Lys  Tyr  Thr  Ala  Leu  Phe  Leu  Ala  Ile  Asp  Ser  Gly  Asn  Pro  Pro  Ala
550                      555                      560                      565

ACA  GGT  ACA  GGA  ACT  TTA  CAC  ATC  ACC  TTG  GAG  GAC  GTC  AAT  GAC  AAT    1782
Thr  Gly  Thr  Gly  Thr  Leu  His  Ile  Thr  Leu  Glu  Asp  Val  Asn  Asp  Asn
                         570                      575                      580

GTC  CCC  TCC  CTT  TAC  CCA  ACA  CTG  GCA  AAA  GTC  TGT  GAT  GAT  GCT  AAA    1830
Val  Pro  Ser  Leu  Tyr  Pro  Thr  Leu  Ala  Lys  Val  Cys  Asp  Asp  Ala  Lys
               585                      590                      595

GAT  CTC  AGA  GTA  GTG  GTT  CTA  GGA  GCA  TCA  GAC  AAA  GAC  CTC  CAT  CCC    1878
Asp  Leu  Arg  Val  Val  Val  Leu  Gly  Ala  Ser  Asp  Lys  Asp  Leu  His  Pro
          600                      605                      610

AAC  ACA  GAT  CCA  TTT  AAA  TTT  GAA  CTG  AGT  AAG  CAA  TCT  GGT  CCA  GAA    1926
Asn  Thr  Asp  Pro  Phe  Lys  Phe  Glu  Leu  Ser  Lys  Gln  Ser  Gly  Pro  Glu
     615                      620                      625

AAG  TTA  TGG  AGA  ATC  AAC  AAG  CTT  AAC  AAT  ACT  CAT  GCC  CAG  GTT  GTC    1974
Lys  Leu  Trp  Arg  Ile  Asn  Lys  Leu  Asn  Asn  Thr  His  Ala  Gln  Val  Val
630                      635                      640                      645

CTG  CTT  CAA  AAC  CTG  AAA  AAG  GCC  AAT  TAC  AAC  ATC  CCA  ATC  TCA  GTG    2022
Leu  Leu  Gln  Asn  Leu  Lys  Lys  Ala  Asn  Tyr  Asn  Ile  Pro  Ile  Ser  Val
                    650                      655                      660

ACA  GAT  TCT  GGA  AAA  CCA  CCT  CTG  ACT  AAC  AAC  ACA  GAA  CTG  AAA  TTA    2070
Thr  Asp  Ser  Gly  Lys  Pro  Pro  Leu  Thr  Asn  Asn  Thr  Glu  Leu  Lys  Leu
               665                      670                      675

CAA  GTG  TGT  TCC  TGC  AAG  AAA  TCC  AGA  ATG  GAC  TGC  AGT  GCA  AGT  GAT    2118
Gln  Val  Cys  Ser  Cys  Lys  Lys  Ser  Arg  Met  Asp  Cys  Ser  Ala  Ser  Asp
          680                      685                      690

GCC  CTT  CAT  ATC  AGC  ATG  ACT  CTT  ATC  CTT  CTT  TCA  CTC  TTC  AGT  TTA    2166
Ala  Leu  His  Ile  Ser  Met  Thr  Leu  Ile  Leu  Leu  Ser  Leu  Phe  Ser  Leu
     695                      700                      705

TTT  TGT  AAG  TCT  TTT  CCT  TAT  GTG  T  AAGCATTGAA  CGTTATTTAT                 2211
Phe  Cys  Lys  Ser  Phe  Pro  Tyr  Val
710                      715

CTGCTTGCTT  TTGCACTATA  AGAAACCTTA  CCAAGAGAGA  AGTTAACTTT  ATTTTTTCCC            2271

TGCGGTAGAT  GCTATACAGA  AGTAGGAGGG  GAGGGATTTT  TCACAGTCAA  AAAATAGCAA            2331

CAAATGCCGG  GTTGTCAAAT  TAAGAAATAG  AAGCAATAAT  TCTAGGAAGA  ATCAAAGAGA            2391

ATTAAAGCTA  GCATATGATA  AACTAAGAAG  TACCAGCTGT  AGTAACAGAT  TTCTGAGATG            2451

CTTTCTTTCA  TCTCTCCCCA  CTTGAATTCA  ATTCAAAAGC  AGAAACTGAA  GATTAAAAGG            2511

TGTTCTTGTA  ACAATAACTG  TTCTGGGTCA  CCATGAAAAT  GAGTACTGTC  TGCTTCAATC            2571

TATTTGTCCG  TAAAGTGCGC  GAGCAATTGG  AACATAAGGA  ACTTACTGAA  GATTCTGGGT            2631

TTAGAGACAC  TCAAACTGAT  AACCAGAATA  GCAGGTCTGT  GTTGAGGGAG  AGAGAACTGA            2691

TGCATAAAGG  AAGCTTCTGC  TGCTTTAGAG  AAAGCTTTCT  AAAAGTCTTA  TGAAATTCCT            2751

AATCTGAATT  AGGAGTTTAA  AGGAATTC                                                  2779
```

( 2 ) INFORMATION FOR SEQ ID NO:4:

( i ) SEQUENCE CHARACTERISTICS:
        ( A ) LENGTH: 717 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Gln  His  Lys  Thr  Gln  Leu  Thr  Leu  Ser  Phe  Leu  Leu  Ser  Gln  Val
1                   5                   10                      15

Leu  Leu  Leu  Ala  Cys  Ala  Glu  Asp  Leu  Glu  Cys  Thr  Pro  Gly  Phe  Gln
```

-continued

|     |     |     | 20  |     |     |     |     | 25  |     |     |     |     | 30  |     |
|-----|-----|-----|-----|-----|-----|-----|-----|-----|-----|-----|-----|-----|-----|-----|
| Gln | Lys | Val | Phe | Tyr | Ile | Glu | Gln | Pro | Phe | Glu | Phe | Thr | Glu | Asp | Gln |
|     |     |     | 35  |     |     |     |     | 40  |     |     |     |     | 45  |     |     |
| Pro | Ile | Leu | Asn | Leu | Val | Phe | Asp | Asp | Cys | Lys | Gly | Asn | Asn | Lys | Leu |
|     |     |     | 50  |     |     |     | 55  |     |     |     |     | 60  |     |     |     |
| Asn | Phe | Glu | Val | Ser | Asn | Pro | Asp | Phe | Lys | Val | Glu | His | Asp | Gly | Ser |
| 65  |     |     |     |     | 70  |     |     |     |     | 75  |     |     |     |     | 80  |
| Leu | Val | Ala | Leu | Lys | Asn | Val | Ser | Glu | Ala | Gly | Arg | Ala | Leu | Phe | Val |
|     |     |     |     | 85  |     |     |     |     | 90  |     |     |     |     | 95  |     |
| His | Ala | Arg | Ser | Glu | His | Ala | Glu | Asp | Met | Ala | Glu | Ile | Leu | Ile | Val |
|     |     |     | 100 |     |     |     |     | 105 |     |     |     |     | 110 |     |     |
| Gly | Ala | Asp | Glu | Lys | His | Asp | Ala | Leu | Lys | Glu | Ile | Phe | Lys | Ile | Glu |
|     |     |     | 115 |     |     |     |     | 120 |     |     |     |     | 125 |     |     |
| Gly | Asn | Leu | Gly | Ile | Pro | Arg | Gln | Lys | Arg | Ala | Ile | Leu | Ala | Thr | Pro |
|     |     | 130 |     |     |     |     | 135 |     |     |     |     | 140 |     |     |     |
| Ile | Leu | Ile | Pro | Glu | Asn | Gln | Arg | Pro | Pro | Phe | Pro | Arg | Ser | Val | Gly |
| 145 |     |     |     |     | 150 |     |     |     |     | 155 |     |     |     |     | 160 |
| Lys | Val | Ile | Arg | Ser | Glu | Gly | Thr | Glu | Gly | Ala | Lys | Phe | Arg | Leu | Ser |
|     |     |     |     | 165 |     |     |     |     | 170 |     |     |     |     | 175 |     |
| Gly | Lys | Gly | Val | Asp | Gln | Asp | Pro | Lys | Gly | Ile | Phe | Arg | Ile | Asn | Glu |
|     |     |     | 180 |     |     |     |     | 185 |     |     |     |     | 190 |     |     |
| Ile | Ser | Gly | Asp | Val | Ser | Val | Thr | Arg | Pro | Leu | Asp | Arg | Glu | Ala | Ile |
|     |     | 195 |     |     |     |     | 200 |     |     |     |     | 205 |     |     |     |
| Ala | Asn | Tyr | Glu | Leu | Glu | Val | Glu | Val | Thr | Asp | Leu | Ser | Gly | Lys | Ile |
|     |     | 210 |     |     |     |     | 215 |     |     |     |     | 220 |     |     |     |
| Ile | Asp | Gly | Pro | Val | Arg | Leu | Asp | Ile | Ser | Val | Ile | Asp | Gln | Asn | Asp |
| 225 |     |     |     |     | 230 |     |     |     |     | 235 |     |     |     |     | 240 |
| Asn | Arg | Pro | Met | Phe | Lys | Glu | Gly | Pro | Tyr | Val | Gly | His | Val | Met | Glu |
|     |     |     | 245 |     |     |     |     | 250 |     |     |     |     | 255 |     |     |
| Gly | Ser | Pro | Thr | Gly | Thr | Thr | Val | Met | Arg | Met | Thr | Ala | Phe | Asp | Ala |
|     |     |     | 260 |     |     |     |     | 265 |     |     |     |     | 270 |     |     |
| Asp | Asp | Pro | Ser | Thr | Asp | Asn | Ala | Leu | Leu | Arg | Tyr | Asn | Ile | Leu | Lys |
|     |     |     | 275 |     |     |     |     | 280 |     |     |     |     | 285 |     |     |
| Gln | Thr | Pro | Thr | Lys | Pro | Ser | Pro | Asn | Met | Phe | Tyr | Ile | Asp | Pro | Glu |
|     |     |     | 290 |     |     |     |     | 295 |     |     |     |     | 300 |     |     |
| Lys | Gly | Asp | Ile | Val | Thr | Val | Val | Ser | Pro | Val | Leu | Leu | Asp | Arg | Glu |
| 305 |     |     |     |     | 310 |     |     |     |     | 315 |     |     |     |     | 320 |
| Thr | Met | Glu | Thr | Pro | Lys | Tyr | Glu | Leu | Val | Ile | Glu | Ala | Lys | Asp | Met |
|     |     |     |     | 325 |     |     |     |     | 330 |     |     |     |     | 335 |     |
| Gly | Gly | His | Asp | Val | Gly | Leu | Thr | Gly | Thr | Ala | Thr | Ala | Thr | Ile | Leu |
|     |     |     | 340 |     |     |     |     | 345 |     |     |     |     | 350 |     |     |
| Ile | Asp | Asp | Lys | Asn | Asp | His | Pro | Pro | Glu | Phe | Thr | Lys | Lys | Glu | Phe |
|     |     |     | 355 |     |     |     |     | 360 |     |     |     |     | 365 |     |     |
| Gln | Ala | Thr | Val | Lys | Glu | Gly | Val | Thr | Gly | Val | Ile | Val | Asn | Leu | Thr |
|     |     |     | 370 |     |     |     |     | 375 |     |     |     |     | 380 |     |     |
| Val | Gly | Asp | Arg | Asp | Asp | Pro | Ala | Thr | Gly | Ala | Trp | Arg | Ala | Val | Tyr |
| 385 |     |     |     |     | 390 |     |     |     |     | 395 |     |     |     |     | 400 |
| Thr | Ile | Ile | Asn | Gly | Asn | Pro | Gly | Gln | Ser | Phe | Glu | Ile | His | Thr | Asn |
|     |     |     |     | 405 |     |     |     |     | 410 |     |     |     |     | 415 |     |
| Pro | Gln | Thr | Asn | Glu | Gly | Met | Leu | Ser | Val | Val | Lys | Pro | Leu | Asp | Tyr |
|     |     |     | 420 |     |     |     |     | 425 |     |     |     |     | 430 |     |     |
| Glu | Ile | Ser | Ala | Phe | His | Thr | Leu | Leu | Ile | Lys | Val | Glu | Asn | Glu | Asp |
|     |     |     | 435 |     |     |     |     | 440 |     |     |     |     | 445 |     |     |

|  |  |  |  |  |  |  |  |  |  |  |  |  |  |  |
|---|---|---|---|---|---|---|---|---|---|---|---|---|---|---|
| Pro | Leu | Ile | Pro | Asp | Ile | Ala | Tyr | Gly | Pro | Ser | Ser | Thr | Ala | Thr | Val |
|  | 450 |  |  |  | 455 |  |  |  |  | 460 |  |  |  |  |  |
| Gln | Ile | Thr | Val | Glu | Asp | Val | Asn | Glu | Gly | Pro | Val | Phe | His | Pro | Asn |
| 465 |  |  |  |  | 470 |  |  |  |  | 475 |  |  |  |  | 480 |
| Pro | Met | Thr | Val | Thr | Lys | Gln | Glu | Asn | Ile | Pro | Ile | Gly | Ser | Ile | Val |
|  |  |  |  | 485 |  |  |  |  | 490 |  |  |  |  | 495 |  |
| Leu | Thr | Val | Asn | Ala | Thr | Asp | Pro | Asp | Thr | Leu | Gln | His | Gln | Thr | Ile |
|  |  |  |  | 500 |  |  |  | 505 |  |  |  |  |  | 510 |  |
| Arg | Tyr | Ser | Val | Tyr | Lys | Asp | Pro | Ala | Ser | Trp | Leu | Glu | Ile | Asn | Pro |
|  |  | 515 |  |  |  |  | 520 |  |  |  |  |  | 525 |  |  |
| Thr | Asn | Gly | Thr | Val | Ala | Thr | Thr | Ala | Val | Leu | Asp | Arg | Glu | Ser | Pro |
|  |  | 530 |  |  |  | 535 |  |  |  |  | 540 |  |  |  |  |
| His | Val | Gln | Asp | Asn | Lys | Tyr | Thr | Ala | Leu | Phe | Leu | Ala | Ile | Asp | Ser |
| 545 |  |  |  |  | 550 |  |  |  |  | 555 |  |  |  |  | 560 |
| Gly | Asn | Pro | Pro | Ala | Thr | Gly | Thr | Gly | Thr | Leu | His | Ile | Thr | Leu | Glu |
|  |  |  |  | 565 |  |  |  |  | 570 |  |  |  |  | 575 |  |
| Asp | Val | Asn | Asp | Asn | Val | Pro | Ser | Leu | Tyr | Pro | Thr | Leu | Ala | Lys | Val |
|  |  |  |  | 580 |  |  |  |  | 585 |  |  |  |  | 590 |  |
| Cys | Asp | Asp | Ala | Lys | Asp | Leu | Arg | Val | Val | Val | Leu | Gly | Ala | Ser | Asp |
|  |  | 595 |  |  |  |  | 600 |  |  |  |  |  | 605 |  |  |
| Lys | Asp | Leu | His | Pro | Asn | Thr | Asp | Pro | Phe | Lys | Phe | Glu | Leu | Ser | Lys |
|  | 610 |  |  |  |  | 615 |  |  |  |  |  | 620 |  |  |  |
| Gln | Ser | Gly | Pro | Glu | Lys | Leu | Trp | Arg | Ile | Asn | Lys | Leu | Asn | Asn | Thr |
| 625 |  |  |  |  | 630 |  |  |  |  | 635 |  |  |  |  | 640 |
| His | Ala | Gln | Val | Val | Leu | Leu | Gln | Asn | Leu | Lys | Ala | Asn | Tyr | Asn |  |
|  |  |  |  | 645 |  |  |  |  | 650 |  |  |  |  | 655 |  |
| Ile | Pro | Ile | Ser | Val | Thr | Asp | Ser | Gly | Lys | Pro | Pro | Leu | Thr | Asn | Asn |
|  |  |  | 660 |  |  |  |  | 665 |  |  |  |  | 670 |  |  |
| Thr | Glu | Leu | Lys | Leu | Gln | Val | Cys | Ser | Cys | Lys | Lys | Ser | Arg | Met | Asp |
|  |  | 675 |  |  |  |  | 680 |  |  |  |  | 685 |  |  |  |
| Cys | Ser | Ala | Ser | Asp | Ala | Leu | His | Ile | Ser | Met | Thr | Leu | Ile | Leu | Leu |
|  | 690 |  |  |  |  | 695 |  |  |  |  | 700 |  |  |  |  |
| Ser | Leu | Phe | Ser | Leu | Phe | Cys | Lys | Ser | Phe | Pro | Tyr | Val |  |  |  |
| 705 |  |  |  |  | 710 |  |  |  |  | 715 |  |  |  |  |  |

(2) INFORMATION FOR SEQ ID NO:5:

(i) SEQUENCE CHARACTERISTICS:
        (A) LENGTH: 712 amino acids
        (B) TYPE: amino acid
        (D) TOPOLOGY: linear (xi) SEQUENCE DESCRIPTION: SEQ ID NO:5:

|  |  |  |  |  |  |  |  |  |  |  |  |  |  |  |  |
|---|---|---|---|---|---|---|---|---|---|---|---|---|---|---|---|
| Met | Gln | His | Lys | Thr | Gln | Leu | Thr | Leu | Ser | Phe | Leu | Leu | Ser | Gln | Val |
| 1 |  |  |  | 5 |  |  |  |  | 10 |  |  |  |  | 15 |  |
| Leu | Leu | Leu | Ala | Cys | Ala | Glu | Asp | Leu | Glu | Cys | Thr | Pro | Gly | Phe | Gln |
|  |  |  | 20 |  |  |  |  | 25 |  |  |  |  | 30 |  |  |
| Gln | Lys | Val | Phe | Tyr | Ile | Glu | Gln | Pro | Phe | Glu | Phe | Thr | Glu | Asp | Gln |
|  |  | 35 |  |  |  |  | 40 |  |  |  |  | 45 |  |  |  |
| Pro | Ile | Leu | Asn | Leu | Val | Phe | Asp | Asp | Cys | Lys | Gly | Asn | Asn | Lys | Leu |
|  | 50 |  |  |  |  | 55 |  |  |  |  | 60 |  |  |  |  |
| Asn | Phe | Glu | Val | Ser | Asn | Pro | Asp | Phe | Lys | Val | Glu | His | Asp | Gly | Ser |
| 65 |  |  |  |  | 70 |  |  |  |  | 75 |  |  |  |  | 80 |
| Leu | Val | Ala | Leu | Lys | Asn | Val | Ser | Glu | Ala | Gly | Arg | Ala | Leu | Phe | Val |
|  |  |  |  | 85 |  |  |  |  | 90 |  |  |  |  | 95 |  |
| His | Ala | Arg | Ser | Glu | His | Ala | Glu | Asp | Met | Ala | Glu | Ile | Leu | Ile | Val |

|     |     |     |     |     | 100 |     |     |     |     | 105 |     |     |     |     | 110 |     |
| --- | --- | --- | --- | --- | --- | --- | --- | --- | --- | --- | --- | --- | --- | --- | --- | --- |

Gly Ala Asp Glu Lys His Asp Ala Leu Lys Glu Ile Phe Lys Ile Glu
              115                     120                 125

Gly Asn Leu Gly Ile Pro Arg Gln Lys Arg Ala Ile Leu Ala Thr Pro
    130             135                 140

Ile Leu Ile Pro Glu Asn Gln Arg Pro Pro Phe Pro Arg Ser Val Gly
145             150                 155                         160

Lys Val Ile Arg Ser Glu Gly Thr Glu Gly Ala Lys Phe Arg Leu Ser
                165             170                         175

Gly Lys Gly Val Asp Gln Asp Pro Lys Gly Ile Phe Arg Ile Asn Glu
            180                 185                     190

Ile Ser Gly Asp Val Ser Val Thr Arg Pro Leu Asp Arg Glu Ala Ile
        195                 200                 205

Ala Asn Tyr Glu Leu Glu Val Glu Val Thr Asp Leu Ser Gly Lys Ile
    210                 215                 220

Ile Asp Gly Pro Val Arg Leu Asp Ile Ser Val Ile Asp Gln Asn Asp
225                 230                 235                     240

Asn Arg Pro Met Phe Lys Glu Gly Pro Tyr Val Gly His Val Met Glu
                245                 250                 255

Gly Ser Pro Thr Gly Thr Thr Val Met Arg Met Thr Ala Phe Asp Ala
            260                 265                 270

Asp Asp Pro Ser Thr Asp Asn Ala Leu Leu Arg Tyr Asn Ile Leu Lys
            275                 280                 285

Gln Thr Pro Thr Lys Pro Ser Pro Asn Met Phe Tyr Ile Asp Pro Glu
    290                 295                 300

Lys Gly Asp Ile Val Thr Val Val Ser Pro Val Leu Leu Asp Arg Glu
305             310                 315                         320

Thr Met Glu Thr Pro Lys Tyr Glu Leu Val Ile Glu Ala Lys Asp Met
                325                 330                 335

Gly Gly His Asp Val Gly Leu Thr Gly Thr Ala Thr Ala Thr Ile Leu
            340                 345                 350

Ile Asp Asp Lys Asn Asp His Pro Pro Glu Phe Thr Lys Lys Glu Phe
        355                 360                 365

Gln Ala Thr Val Lys Glu Gly Val Thr Gly Val Ile Val Asn Leu Thr
    370                 375                 380

Val Gly Asp Arg Asp Asp Pro Ala Thr Gly Ala Trp Arg Ala Val Tyr
385                 390                 395                     400

Thr Ile Ile Asn Gly Asn Pro Gly Gln Ser Phe Glu Ile His Thr Asn
                405                 410                 415

Pro Gln Thr Asn Glu Gly Met Leu Ser Val Val Lys Pro Leu Asp Tyr
            420                 425                 430

Glu Ile Ser Ala Phe His Thr Leu Leu Ile Lys Val Glu Asn Glu Asp
        435                 440                 445

Pro Leu Ile Pro Asp Ile Ala Tyr Gly Pro Ser Ser Thr Ala Thr Val
    450                 455                 460

Gln Ile Thr Val Glu Asp Val Asn Glu Gly Pro Val Phe His Pro Asn
465                 470                 475                     480

Pro Met Thr Val Thr Lys Gln Glu Asn Ile Pro Ile Gly Ser Ile Val
                485                 490                 495

Leu Thr Val Asn Ala Thr Asp Pro Asp Thr Leu Gln His Gln Thr Ile
            500                 505                 510

Arg Tyr Ser Val Tyr Lys Asp Pro Ala Ser Trp Leu Glu Ile Asn Pro
        515                 520                 525

-continued

| | | | | | | | | | | | | | | | |
|---|---|---|---|---|---|---|---|---|---|---|---|---|---|---|---|
| Thr | Asn | Gly | Thr | Val | Ala | Thr | Thr | Ala | Val | Leu | Asp | Arg | Glu | Ser | Pro |
| | | 530 | | | | 535 | | | | 540 | | | | | |
| His | Val | Gln | Asp | Asn | Lys | Tyr | Thr | Ala | Leu | Phe | Leu | Ala | Ile | Asp | Ser |
| 545 | | | | | 550 | | | | | 555 | | | | | 560 |
| Gly | Asn | Pro | Pro | Ala | Thr | Gly | Thr | Gly | Leu | His | Ile | Thr | Leu | Glu | |
| | | | | 565 | | | | 570 | | | | | 575 | | |
| Asp | Val | Asn | Asp | Asn | Val | Pro | Ser | Leu | Tyr | Pro | Thr | Leu | Ala | Lys | Val |
| | | | 580 | | | | | 585 | | | | | 590 | | |
| Cys | Asp | Asp | Ala | Lys | Asp | Leu | Arg | Val | Val | Val | Leu | Gly | Ala | Ser | Asp |
| | | 595 | | | | | 600 | | | | | 605 | | | |
| Lys | Asp | Leu | His | Pro | Asn | Thr | Asp | Pro | Phe | Lys | Phe | Glu | Leu | Ser | Lys |
| | 610 | | | | | 615 | | | | | 620 | | | | |
| Gln | Ser | Gly | Pro | Glu | Lys | Leu | Trp | Arg | Ile | Asn | Lys | Leu | Asn | Asn | Thr |
| 625 | | | | | 630 | | | | | 635 | | | | | 640 |
| His | Ala | Gln | Val | Val | Leu | Leu | Gln | Asn | Leu | Lys | Lys | Ala | Asn | Tyr | Asn |
| | | | | 645 | | | | | 650 | | | | | 655 | |
| Ile | Pro | Ile | Ser | Val | Thr | Asp | Ser | Gly | Lys | Pro | Pro | Leu | Thr | Asn | Asn |
| | | | 660 | | | | | 665 | | | | | 670 | | |
| Thr | Glu | Leu | Lys | Leu | Gln | Val | Cys | Ser | Cys | Lys | Lys | Ser | Arg | Met | Asp |
| | | 675 | | | | | 680 | | | | | 685 | | | |
| Cys | Ser | Ala | Ser | Asp | Ala | Leu | His | Ile | Ser | Met | Thr | Leu | Ile | Leu | Leu |
| | | 690 | | | | | 695 | | | | 700 | | | | |
| Ser | Leu | Phe | Ser | Leu | Phe | Cys | Leu | | | | | | | | |
| 705 | | | | | 710 | | | | | | | | | | |

(2) INFORMATION FOR SEQ ID NO:6:

(i) SEQUENCE CHARACTERISTICS:
        (A) LENGTH: 913 amino acids
        (B) TYPE: amino acid
        (D) TOPOLOGY: linear (xi) SEQUENCE DESCRIPTION: SEQ ID NO:6:

| | | | | | | | | | | | | | | | |
|---|---|---|---|---|---|---|---|---|---|---|---|---|---|---|---|
| Met | Cys | Arg | Ile | Ala | Gly | Thr | Pro | Pro | Arg | Ile | Leu | Pro | Pro | Leu | Ala |
| 1 | | | | 5 | | | | | 10 | | | | | 15 | |
| Leu | Met | Leu | Leu | Ala | Ala | Leu | Gln | Gln | Ala | Pro | Ile | Lys | Ala | Thr | Cys |
| | | | 20 | | | | | 25 | | | | | 30 | | |
| Glu | Asp | Met | Leu | Cys | Lys | Met | Gly | Phe | Pro | Glu | Asp | Val | His | Ser | Ala |
| | | | 35 | | | | | 40 | | | | | 45 | | |
| Val | Val | Ser | Arg | Ser | Val | His | Gly | Gly | Gln | Pro | Leu | Leu | Asn | Val | Arg |
| | 50 | | | | | 55 | | | | | 60 | | | | |
| Phe | Gln | Ser | Cys | Asp | Glu | Asn | Arg | Lys | Ile | Tyr | Phe | Gly | Ser | Ser | Glu |
| 65 | | | | | 70 | | | | | 75 | | | | | 80 |
| Pro | Glu | Asp | Phe | Arg | Val | Gly | Glu | Asp | Gly | Val | Val | Tyr | Ala | Glu | Arg |
| | | | | 85 | | | | | 90 | | | | | 95 | |
| Ser | Phe | Gln | Leu | Ser | Ala | Glu | Pro | Thr | Glu | Phe | Val | Val | Ser | Ala | Arg |
| | | | 100 | | | | | 105 | | | | | 110 | | |
| Asp | Lys | Glu | Thr | Gln | Glu | Glu | Trp | Gln | Met | Lys | Val | Lys | Leu | Thr | Pro |
| | | | 115 | | | | | 120 | | | | | 125 | | |
| Glu | Pro | Ala | Phe | Thr | Gly | Ala | Ser | Glu | Lys | Asp | Gln | Lys | Lys | Ile | Glu |
| | | | 130 | | | | | 135 | | | | | 140 | | |
| Asp | Ile | Ile | Phe | Pro | Trp | Gln | Gln | Tyr | Lys | Asp | Ser | Ser | His | Leu | Lys |
| 145 | | | | | 150 | | | | | 155 | | | | | 160 |
| Arg | Gln | Lys | Arg | Asp | Trp | Val | Ile | Pro | Pro | Ile | Asn | Leu | Pro | Glu | Asn |
| | | | | 165 | | | | | 170 | | | | | 175 | |
| Ser | Arg | Gly | Pro | Phe | Pro | Gln | Glu | Leu | Val | Arg | Ile | Arg | Ser | Asp | Arg |

-continued

|     |     |     |     |     | 180 |     |     |     |     | 185 |     |     |     |     | 190 |     |     |
| --- | --- | --- | --- | --- | --- | --- | --- | --- | --- | --- | --- | --- | --- | --- | --- | --- | --- |
| Asp | Lys | Ser | Leu | Ser | Leu | Arg | Tyr | Ser | Val | Thr | Gly | Pro | Gly | Ala | Asp |
|     |     | 195 |     |     |     |     | 200 |     |     |     |     | 205 |     |     |     |
| Gln | Pro | Pro | Thr | Gly | Ile | Phe | Ile | Ile | Asn | Pro | Ile | Ser | Gly | Gln | Leu |
|     |     | 210 |     |     |     | 215 |     |     |     |     | 220 |     |     |     |     |
| Ser | Val | Thr | Lys | Pro | Leu | Asp | Arg | Glu | Gln | Ile | Ala | Ser | Phe | His | Leu |
| 225 |     |     |     |     | 230 |     |     |     | 235 |     |     |     |     |     | 240 |
| Arg | Ala | His | Ala | Val | Asp | Val | Asn | Gly | Asn | Gln | Val | Glu | Asn | Pro | Ile |
|     |     |     |     | 245 |     |     |     |     | 250 |     |     |     |     | 255 |     |
| Asp | Ile | Val | Ile | Asn | Val | Ile | Asp | Met | Asn | Asp | Asn | Arg | Pro | Glu | Phe |
|     |     |     | 260 |     |     |     |     | 265 |     |     |     |     | 270 |     |     |
| Leu | His | Gln | Val | Trp | Asn | Gly | Thr | Val | Pro | Glu | Gly | Ser | Lys | Pro | Gly |
|     |     | 275 |     |     |     |     | 280 |     |     |     |     | 285 |     |     |     |
| Thr | Tyr | Val | Met | Thr | Val | Thr | Ala | Ile | Asp | Ala | Asp | Asp | Pro | Asn | Ala |
|     |     | 290 |     |     |     |     | 295 |     |     |     |     | 300 |     |     |     |
| Gln | Asn | Gly | Met | Leu | Arg | Tyr | Arg | Ile | Leu | Ser | Gln | Ala | Pro | Ser | Ser |
| 305 |     |     |     |     | 310 |     |     |     |     | 315 |     |     |     |     | 320 |
| Pro | Ser | Pro | Asn | Met | Phe | Thr | Ile | Asn | Asn | Glu | Thr | Gly | Asp | Ile | Ile |
|     |     |     |     | 325 |     |     |     |     | 330 |     |     |     |     | 335 |     |
| Thr | Val | Ala | Ala | Gly | Leu | Asp | Arg | Glu | Lys | Val | Gln | Gln | Tyr | Thr | Leu |
|     |     |     | 340 |     |     |     |     | 345 |     |     |     |     | 350 |     |     |
| Ile | Ile | Gln | Ala | Thr | Asp | Met | Glu | Gly | Asn | Pro | Thr | Tyr | Gly | Leu | Ser |
|     |     |     | 355 |     |     |     |     | 360 |     |     |     |     | 365 |     |     |
| Asn | Thr | Ala | Thr | Ala | Val | Ile | Thr | Val | Thr | Asp | Val | Asn | Asp | Asn | Pro |
|     | 370 |     |     |     |     | 375 |     |     |     |     | 380 |     |     |     |     |
| Pro | Glu | Phe | Thr | Ala | Met | Thr | Phe | Tyr | Gly | Glu | Val | Pro | Glu | Asn | Arg |
| 385 |     |     |     |     | 390 |     |     |     |     | 395 |     |     |     |     | 400 |
| Val | Asp | Val | Ile | Val | Ala | Asn | Leu | Thr | Val | Thr | Asp | Lys | Asp | Gln | Pro |
|     |     |     |     | 405 |     |     |     |     | 410 |     |     |     |     | 415 |     |
| His | Thr | Pro | Ala | Trp | Asn | Ala | Arg | Tyr | Gln | Met | Thr | Gly | Gly | Asp | Pro |
|     |     |     | 420 |     |     |     |     | 425 |     |     |     |     | 430 |     |     |
| Thr | Gly | Gln | Phe | Thr | Ile | Leu | Thr | Asp | Pro | Asn | Ser | Asn | Asp | Gly | Leu |
|     |     | 435 |     |     |     |     | 440 |     |     |     |     | 445 |     |     |     |
| Val | Thr | Val | Val | Lys | Pro | Ile | Asp | Phe | Glu | Thr | Asn | Arg | Met | Phe | Val |
|     |     | 450 |     |     |     |     | 455 |     |     |     |     | 460 |     |     |     |
| Leu | Thr | Val | Ala | Ala | Glu | Asn | Gln | Val | Pro | Leu | Ala | Lys | Gly | Ile | Gln |
| 465 |     |     |     |     | 470 |     |     |     |     | 475 |     |     |     |     | 480 |
| His | Pro | Pro | Gln | Ser | Thr | Ala | Thr | Val | Ser | Ile | Thr | Val | Ile | Asp | Val |
|     |     |     |     | 485 |     |     |     |     | 490 |     |     |     |     | 495 |     |
| Asn | Glu | Ser | Pro | Tyr | Phe | Val | Pro | Asn | Pro | Lys | Leu | Val | Arg | Gln | Glu |
|     |     |     |     | 500 |     |     |     |     | 505 |     |     |     |     | 510 |     |
| Glu | Gly | Leu | Leu | Ala | Gly | Ser | Met | Leu | Thr | Thr | Phe | Thr | Ala | Arg | Asp |
|     |     |     | 515 |     |     |     |     | 520 |     |     |     |     | 525 |     |     |
| Pro | Asp | Arg | Tyr | Met | Gln | Gln | Thr | Ser | Leu | Arg | Tyr | Ser | Lys | Leu | Ser |
|     |     | 530 |     |     |     |     | 535 |     |     |     |     | 540 |     |     |     |
| Asp | Pro | Ala | Asn | Trp | Leu | Lys | Ile | Asp | Pro | Val | Asn | Gly | Gln | Ile | Thr |
| 545 |     |     |     |     | 550 |     |     |     |     | 555 |     |     |     |     | 560 |
| Thr | Thr | Ala | Val | Leu | Asp | Arg | Glu | Ser | Ile | Tyr | Val | Gln | Asn | Asn | Met |
|     |     |     |     | 565 |     |     |     |     | 570 |     |     |     |     | 575 |     |
| Tyr | Asn | Ala | Thr | Phe | Leu | Ala | Ser | Asp | Asn | Gly | Ile | Pro | Pro | Met | Ser |
|     |     |     | 580 |     |     |     |     | 585 |     |     |     |     | 590 |     |     |
| Gly | Thr | Gly | Thr | Leu | Gln | Ile | Tyr | Leu | Leu | Asp | Ile | Asn | Asp | Asn | Ala |
|     |     | 595 |     |     |     |     | 600 |     |     |     |     | 605 |     |     |     |

| | | | | | | | | | | | | | | |
|---|---|---|---|---|---|---|---|---|---|---|---|---|---|---|
|Pro|Gln|Val|Asn|Pro|Lys|Glu|Ala|Thr|Thr|Cys|Glu|Thr|Leu|Gln|Pro|
| |610| | | |615| | | | |620| | | | |
|Asn|Ala|Ile|Asn|Ile|Thr|Ala|Val|Asp|Pro|Asp|Ile|Asp|Pro|Asn|Ala|
|625| | | | |630| | | | |635| | | | |640|
|Gly|Pro|Phe|Ala|Phe|Glu|Leu|Pro|Asp|Ser|Pro|Pro|Ser|Ile|Lys|Arg|
| | | | |645| | | | |650| | | | |655| |
|Asn|Trp|Thr|Ile|Val|Arg|Ile|Ser|Gly|Asp|His|Ala|Gln|Leu|Ser|Leu|
| | | |660| | | | |665| | | | |670| | |
|Arg|Ile|Arg|Phe|Leu|Glu|Ala|Gly|Ile|Tyr|Asp|Val|Pro|Ile|Val|Ile|
| | |675| | | | |680| | | | |685| | | |
|Thr|Asp|Ser|Gly|Asn|Pro|His|Ala|Ser|Ser|Thr|Ser|Val|Leu|Lys|Val|
| |690| | | | |695| | | | |700| | | | |
|Lys|Val|Cys|Gln|Cys|Asp|Ile|Asn|Gly|Asp|Cys|Thr|Asp|Val|Asp|Arg|
|705| | | | |710| | | | |715| | | | |720|
|Ile|Val|Gly|Ala|Gly|Leu|Gly|Thr|Gly|Ala|Ile|Ile|Ala|Ile|Leu|Leu|
| | | | |725| | | | |730| | | | |735| |
|Cys|Ile|Ile|Ile|Leu|Leu|Ile|Leu|Val|Leu|Met|Phe|Val|Val|Trp|Met|
| | | |740| | | | |745| | | | |750| | |
|Lys|Arg|Arg|Asp|Lys|Glu|Arg|Gln|Ala|Lys|Gln|Leu|Leu|Ile|Asp|Pro|
| | |755| | | | |760| | | | |765| | | |
|Glu|Asp|Asp|Val|Arg|Asp|Asn|Ile|Leu|Lys|Tyr|Asp|Glu|Glu|Gly|Gly|
| |770| | | | |775| | | | |780| | | | |
|Gly|Glu|Glu|Asp|Gln|Asp|Tyr|Asp|Leu|Ser|Gln|Leu|Gln|Gln|Pro|Asp|
|785| | | | |790| | | | |795| | | | |800|
|Thr|Val|Glu|Pro|Asp|Ala|Ile|Lys|Pro|Val|Gly|Ile|Arg|Arg|Leu|Asp|
| | | | |805| | | | |810| | | | |815| |
|Glu|Arg|Pro|Ile|His|Ala|Glu|Pro|Gln|Tyr|Pro|Val|Arg|Ser|Ala|Ala|
| | | |820| | | | |825| | | | |830| | |
|Pro|His|Pro|Gly|Asp|Ile|Gly|Asp|Phe|Ile|Asn|Glu|Gly|Leu|Ala|Lys|
| | |835| | | | |840| | | | |845| | | |
|Ala|Ala|Asp|Asn|Asp|Pro|Thr|Ala|Pro|Pro|Tyr|Asp|Ser|Leu|Leu|Val|
| |850| | | | |855| | | | |860| | | | |
|Phe|Asp|Tyr|Glu|Gly|Ser|Gly|Ser|Thr|Ala|Gly|Ser|Leu|Ser|Ser|Leu|
|865| | | | |870| | | | |875| | | | |880|
|Asn|Ser|Ser|Ser|Ser|Gly|Gly|Glu|Gln|Asp|Tyr|Asp|Tyr|Leu|Asn|Asp|
| | | | |885| | | | |890| | | | |895| |
|Trp|Gly|Pro|Arg|Phe|Lys|Lys|Leu|Ala|Asp|Met|Tyr|Gly|Gly|Gly|Asp|
| | | |900| | | | |905| | | | |910| | |
|Asp| | | | | | | | | | | | | | | |

( 2 ) INFORMATION FOR SEQ ID NO:7:

( i ) SEQUENCE CHARACTERISTICS:
        ( A ) LENGTH: 837 amino acids
        ( B ) TYPE: amino acid
        ( D ) TOPOLOGY: linear ( x i ) SEQUENCE DESCRIPTION: SEQ ID NO:7:

| | | | | | | | | | | | | | | | |
|---|---|---|---|---|---|---|---|---|---|---|---|---|---|---|---|
|Asp|Ser|Val|Ala|Ala|Gly|Arg|Glu|Leu|Gly|Arg|Val|Ser|Phe|Ala|Ala|
|1| | | |5| | | | |10| | | | |15| |
|Cys|Ser|Gly|Arg|Pro|Trp|Ala|Val|Tyr|Val|Pro|Thr|Asp|Thr|Arg|Phe|
| | | |20| | | | |25| | | | |30| | |
|Lys|Val|Asn|Gly|Asp|Gly|Val|Val|Ser|Thr|Lys|Arg|Pro|Leu|Thr|Leu|
| | |35| | | | |40| | | | |45| | | |
|Tyr|Gly|Arg|Lys|Ile|Ser|Phe|Thr|Ile|Tyr|Ala|Gln|Asp|Ala|Met|Gly|
| |50| | | | |55| | | | |60| | | | |

-continued

```
Lys Arg His Ser Ala Arg Val Thr Val Gly Arg His Arg His Arg Arg
 65              70                  75                  80

His His His Asn His His Leu Gln Asp Thr Thr Pro Ala Val Leu Thr
                 85                  90                  95

Phe Pro Lys His Asp Pro Gly Phe Leu Arg Arg Gln Lys Arg Asp Trp
                100                 105                 110

Val Ile Pro Pro Ile Ser Cys Leu Glu Asn His Arg Gly Pro Tyr Pro
            115                 120                 125

Met Arg Leu Val Gln Ile Lys Ser Asn Lys Asp Lys Glu Ser Lys Val
        130                 135                 140

Tyr Tyr Ser Ile Thr Gly Gln Gly Ala Asp Ser Pro Pro Val Gly Ile
145                 150                 155                 160

Phe Ile Ile Glu Arg Glu Thr Gly Trp Leu Glu Val Thr Glu Gln Leu
                165                 170                 175

Asp Arg Glu Lys Ile Asp Arg Tyr Thr Leu Leu Ser His Ala Val Ser
            180                 185                 190

Ala Ser Gly Gln Pro Val Glu Asp Pro Met Glu Ile Ile Ile Thr Val
        195                 200                 205

Met Asp Gln Asn Asp Asn Lys Pro Val Phe Ile Lys Glu Val Phe Val
        210                 215                 220

Gly Tyr Ile Glu Glu Asn Ala Lys Pro Gly Thr Ser Val Met Thr Val
225                 230                 235                 240

Asn Ala Thr Asp Ala Asp Asp Ala Val Asn Thr Asp Asn Gly Ile Val
                245                 250                 255

Ser Tyr Ser Ile Val Ser Gln Gln Pro Pro Arg Pro His Pro Gln Met
            260                 265                 270

Phe Thr Ile Asp Pro Ala Lys Gly Ile Ile Ser Val Leu Gly Thr Gly
        275                 280                 285

Leu Asp Arg Glu Thr Thr Pro Asn Tyr Thr Leu Ile Val Gln Ala Thr
290                 295                 300

Asp Gln Glu Gly Lys Gly Leu Ser Asn Thr Ala Thr Ala Ile Ile Glu
305                 310                 315                 320

Val Thr Asp Ala Asn Asp Asn Ile Pro Ile Phe Asn Pro Thr Met Tyr
                325                 330                 335

Glu Gly Val Val Glu Glu Asn Lys Pro Gly Thr Glu Val Ala Arg Leu
            340                 345                 350

Thr Val Thr Asp Gln Asp Ala Pro Gly Ser Pro Ala Trp Gln Ala Val
        355                 360                 365

Tyr His Ile Lys Ser Gly Asn Leu Asp Gly Ala Phe Ser Ile Ile Thr
370                 375                 380

Asp Pro Ser Thr Asn Asn Gly Ile Leu Lys Thr Ala Lys Gly Leu Asp
385                 390                 395                 400

Tyr Glu Thr Lys Ser Arg Tyr Asp Leu Val Val Thr Val Glu Asn Lys
                405                 410                 415

Val Pro Leu Ser Val Pro Ile Thr Leu Ser Thr Ala Ser Val Leu Val
            420                 425                 430

Thr Val Leu Asp Val Asn Glu Pro Pro Val Phe Val Pro Pro Ile Lys
        435                 440                 445

Arg Val Gly Val Pro Glu Asp Leu Pro Val Gly Gln Val Thr Ser
        450                 455                 460

Tyr Thr Ala Glu Asp Pro Asp Arg Asp Met Arg Gln Lys Ile Thr Tyr
465                 470                 475                 480

Arg Met Gly Ser Asp Pro Ala Gly Trp Leu Tyr Ile His Pro Glu Asn
```

|     |     |     |     | 485 |     |     |     | 490 |     |     |     | 495 |     |
| --- | --- | --- | --- | --- | --- | --- | --- | --- | --- | --- | --- | --- | --- |
| Gly | Ile | Val | Thr<br>500 | Ala | Thr | Gln | Pro<br>505 | Leu | Asp | Arg | Glu | Ser<br>510 | Val | His | Ala |
| Ile | Asn | Ser<br>515 | Thr | Tyr | Lys | Ala<br>520 | Ile | Ile | Leu | Ala | Val<br>525 | Asp | Asn | Gly | Ile |
| Pro | Asp<br>530 | Thr | Thr | Gly | Thr<br>535 | Gly | Thr | Leu | Leu | Leu<br>540 | Leu | Leu | Gln | Asp | Val |
| Asn<br>545 | Asp | Asn | Gly | Pro | Thr<br>550 | Pro | Glu | Pro | Arg | Ser<br>555 | Phe | Glu | Ile | Cys | Ser<br>560 |
| Arg | Gln | Pro | Glu | Lys<br>565 | Gln | Ile | Leu | Ser | Ile<br>570 | Val | Asp | Lys | Asp | Leu<br>575 | Pro |
| Pro | His | Thr | Tyr<br>580 | Pro | Phe | Lys | Ala | Ala<br>585 | Leu | Glu | His | Gly | Ser<br>590 | Ser | Asn |
| Asn | Trp | Thr<br>595 | Val | Glu | Ile | Arg | Gly<br>600 | Gln | Asp | Glu | Leu | Ala<br>605 | Met | Gly | Leu |
| Lys | Lys<br>610 | Glu | Leu | Glu | Pro | Gly<br>615 | Glu | Tyr | Asn | Ile | Phe<br>620 | Val | Lys | Leu | Thr |
| Asp<br>625 | Ser | Gln | Gly | Lys | Ala<br>630 | Gln | Val | Thr | Gln | Val<br>635 | Lys | Ala | Gln | Val | Cys<br>640 |
| Glu | Cys | Glu | Gly | Thr<br>645 | Ala | Lys | Asn | Cys | Glu<br>650 | Arg | Arg | Ser | Tyr | Ile<br>655 | Val |
| Gly | Gly | Leu | Gly<br>660 | Val | Pro | Ala | Ile | Leu<br>665 | Gly | Ile | Leu | Gly | Gly<br>670 | Ile | Leu |
| Ala | Leu | Leu<br>675 | Ile | Leu | Leu | Leu | Leu<br>680 | Leu | Leu | Leu | Phe | Ala<br>685 | Arg | Arg | Arg |
| Lys | Val<br>690 | Glu | Lys | Glu | Pro | Leu<br>695 | Leu | Pro | Pro | Glu | Asp<br>700 | Asp | Met | Arg | Asp |
| Asn<br>705 | Val | Tyr | Asn | Tyr | Asp<br>710 | Glu | Glu | Gly | Gly | Glu<br>715 | Glu | Asp | Gln | Asp<br>720 |
| Tyr | Asp | Leu | Ser | Gln<br>725 | Leu | His | Arg | Gly | Leu<br>730 | Asp | Ala | Arg | Pro | Glu<br>735 | Val |
| Ile | Arg | Asn | Asp<br>740 | Val | Ala | Pro | Pro | Leu<br>745 | Met | Ala | Ala | Pro | Gln<br>750 | Tyr | Arg |
| Pro | Arg | Pro<br>755 | Ala | Asn | Pro | Asp | Glu<br>760 | Ile | Gly | Asn | Phe | Ile<br>765 | Asp | Glu | Asn |
| Leu | Lys<br>770 | Ala | Ala | Asp | Thr | Asp<br>775 | Pro | Thr | Ala | Pro | Pro<br>780 | Tyr | Asp | Ser | Leu |
| Leu<br>785 | Val | Phe | Asp | Tyr | Glu<br>790 | Gly | Gly | Gly | Ser | Glu<br>795 | Ala | Thr | Ser | Leu | Ser<br>800 |
| Ser | Leu | Asn | Ser | Ser<br>805 | Ala | Ser | Asp | Gln<br>810 | Asp | Gln | Asp | Tyr | Asp<br>815 | Tyr | Leu |
| Asn | Glu | Trp | Gly<br>820 | Asn | Arg | Phe | Lys | Lys<br>825 | Leu | Ala | Glu | Leu | Tyr<br>830 | Gly | Gly |
| Gly | Glu | Asp | Asp<br>835 | Glu |     |     |     |     |     |     |     |     |     |     |     |

( 2 ) INFORMATION FOR SEQ ID NO:8:

( i ) SEQUENCE CHARACTERISTICS:
        ( A ) LENGTH: 884 amino acids
        ( B ) TYPE: amino acid
        ( D ) TOPOLOGY: linear ( x i ) SEQUENCE DESCRIPTION: SEQ ID NO:8:

| Met<br>1 | Gly | Ala | Arg | Cys<br>5 | Arg | Ser | Phe | Ser | Ala<br>10 | Leu | Leu | Leu | Leu | Leu<br>15 | Gln |
| --- | --- | --- | --- | --- | --- | --- | --- | --- | --- | --- | --- | --- | --- | --- | --- |

|     |     |     |     |     |     |     |     |     |     |     |     |     |     |     |
| --- | --- | --- | --- | --- | --- | --- | --- | --- | --- | --- | --- | --- | --- | --- |
| Val | Ser | Ser | Trp<br>20 | Leu | Cys | Gln | Glu | Leu<br>25 | Glu | Pro | Glu | Ser<br>30 | Cys | Ser | Pro |
| Gly | Phe | Ser<br>35 | Ser | Glu | Val | Tyr | Thr<br>40 | Phe | Pro | Val | Pro<br>45 | Glu | Arg | His | Leu |
| Glu | Arg<br>50 | Gly | His | Val | Leu<br>55 | Gly | Arg | Val | Arg | Phe<br>60 | Glu | Gly | Cys | Thr | Gly |
| Arg<br>65 | Pro | Arg | Thr | Ala | Phe<br>70 | Phe | Ser | Glu | Asp | Ser<br>75 | Arg | Phe | Lys | Val | Ala<br>80 |
| Thr | Asp | Gly | Thr | Ile<br>85 | Thr | Val | Lys | Arg | His<br>90 | Leu | Lys | Leu | His | Lys<br>95 | Leu |
| Glu | Thr | Ser | Phe<br>100 | Leu | Val | Arg | Ala | Arg<br>105 | Asp | Ser | Ser | His | Arg<br>110 | Glu | Leu |
| Ser | Thr | Lys<br>115 | Val | Thr | Leu | Lys | Ser<br>120 | Met | Gly | His | His | His<br>125 | His | Arg | His |
| His<br>130 | His | Arg | Asp | Pro | Ala<br>135 | Ser | Glu | Ser | Asn | Pro<br>140 | Glu | Leu | Leu | Met | Phe |
| Pro<br>145 | Ser | Val | Tyr | Pro | Gly<br>150 | Leu | Arg | Arg | Gln | Lys<br>155 | Arg | Asp | Trp | Val | Ile<br>160 |
| Pro | Pro | Ile | Ser | Cys<br>165 | Pro | Glu | Asn | Glu | Lys<br>170 | Gly | Glu | Phe | Pro | Lys<br>175 | Asn |
| Leu | Val | Gln | Ile<br>180 | Lys | Ser | Asn | Arg | Asp<br>185 | Lys | Glu | Thr | Lys | Val<br>190 | Phe | Tyr |
| Ser | Ile | Thr<br>195 | Gly | Gln | Gly | Ala | Asp<br>200 | Lys | Pro | Pro | Val | Gly<br>205 | Val | Phe | Ile |
| Ile | Glu<br>210 | Arg | Glu | Thr | Gly | Trp<br>215 | Leu | Lys | Val | Thr | Gln<br>220 | Pro | Leu | Asp | Arg |
| Glu<br>225 | Ala | Ile | Ala | Lys | Tyr<br>230 | Ile | Leu | Tyr | Ser | His<br>235 | Ala | Val | Ser | Ser | Asn<br>240 |
| Gly | Glu | Ala | Val | Glu<br>245 | Asp | Pro | Met | Glu | Ile<br>250 | Val | Ile | Thr | Val | Thr<br>255 | Asp |
| Gln | Asn | Asp | Asn | Arg<br>260 | Pro | Glu | Phe | Thr | Gln<br>265 | Glu | Val | Phe | Glu | Gly<br>270 | Ser |
| Val | Ala | Glu | Gly<br>275 | Ala | Val | Pro | Gly | Thr<br>280 | Ser | Val | Met | Lys | Val<br>285 | Ser | Ala |
| Thr | Asp<br>290 | Ala | Asp | Asp | Asp | Val<br>295 | Asn | Thr | Tyr | Asn | Ala<br>300 | Ala | Ile | Ala | Tyr |
| Thr<br>305 | Ile | Val | Ser | Gln | Asp<br>310 | Pro | Glu | Leu | Pro | His<br>315 | Lys | Asn | Met | Phe | Thr<br>320 |
| Val | Asn | Arg | Asp | Thr<br>325 | Gly | Val | Ile | Ser | Val<br>330 | Leu | Thr | Ser | Gly | Leu<br>335 | Asp |
| Arg | Glu | Ser | Tyr<br>340 | Pro | Thr | Tyr | Thr | Leu<br>345 | Val | Val | Gln | Ala | Ala<br>350 | Asp | Leu |
| Gln | Gly | Glu<br>355 | Gly | Leu | Ser | Thr | Thr<br>360 | Ala | Lys | Ala | Val | Ile<br>365 | Thr | Val | Lys |
| Asp | Ile<br>370 | Asn | Asp | Asn | Ala | Pro<br>375 | Val | Phe | Asn | Pro | Ser<br>380 | Thr | Tyr | Gln | Gly |
| Gln<br>385 | Val | Pro | Glu | Asn | Glu<br>390 | Val | Asn | Ala | Arg | Ile<br>395 | Ala | Thr | Leu | Lys | Val<br>400 |
| Thr | Asp | Asp | Asp | Ala<br>405 | Pro | Asn | Thr | Pro | Ala<br>410 | Trp | Lys | Val | Val | Tyr<br>415 | Thr |
| Val | Val | Asn | Asp | Pro<br>420 | Asp | Gln | Gln | Phe | Val<br>425 | Val | Val | Thr | Asp<br>430 | Pro | Thr |
| Thr | Asn | Asp | Gly | Ile | Leu | Lys | Thr | Ala | Lys | Gly | Leu | Asp | Phe | Glu | Ala |

-continued

```
                        435                                 440                                 445
Lys  Gln  Gln  Tyr  Ile  Leu  His  Val  Arg  Val  Glu  Asn  Glu  Glu  Pro  Phe
     450                      455                      460

Glu  Gly  Ser  Leu  Val  Pro  Ser  Thr  Ala  Thr  Val  Thr  Val  Asp  Val  Val
465                      470                      475                      480

Asp  Val  Asn  Glu  Ala  Pro  Ile  Phe  Met  Pro  Ala  Glu  Arg  Arg  Val  Glu
                    485                      490                           495

Val  Pro  Glu  Asp  Phe  Gly  Val  Gly  Gln  Glu  Ile  Thr  Ser  Tyr  Thr  Ala
               500                      505                      510

Arg  Glu  Pro  Asp  Thr  Phe  Met  Asp  Gln  Lys  Ile  Thr  Tyr  Arg  Ile  Trp
          515                      520                      525

Arg  Asp  Thr  Ala  Asn  Trp  Leu  Glu  Ile  Asn  Pro  Glu  Thr  Gly  Ala  Ile
530                      535                      540

Phe  Thr  Arg  Ala  Glu  Met  Asp  Arg  Glu  Asp  Ala  Glu  His  Val  Lys  Asn
545                      550                      555                      560

Ser  Thr  Tyr  Val  Ala  Leu  Ile  Ile  Ala  Thr  Asp  Asp  Gly  Ser  Pro  Ile
                    565                      570                      575

Ala  Thr  Gly  Thr  Gly  Thr  Leu  Leu  Leu  Val  Leu  Leu  Asp  Val  Asn  Asp
               580                      585                      590

Asn  Ala  Pro  Ile  Pro  Glu  Pro  Arg  Asn  Met  Gln  Phe  Cys  Gln  Arg  Asn
          595                      600                      605

Pro  Gln  Pro  His  Ile  Ile  Thr  Ile  Leu  Asp  Pro  Asp  Leu  Pro  Pro  Asn
     610                      615                      620

Thr  Ser  Pro  Phe  Thr  Ala  Glu  Leu  Thr  His  Gly  Ala  Ser  Val  Asn  Trp
625                      630                      635                      640

Thr  Ile  Glu  Tyr  Asn  Asp  Ala  Ala  Gln  Glu  Ser  Leu  Ile  Leu  Gln  Pro
                    645                      650                      655

Arg  Lys  Asp  Leu  Glu  Ile  Gly  Glu  Tyr  Lys  Ile  His  Leu  Lys  Leu  Ala
               660                      665                      670

Asp  Asn  Gln  Asn  Lys  Asp  Gln  Val  Thr  Thr  Leu  Asp  Val  His  Val  Cys
          675                      680                      685

Asp  Cys  Glu  Gly  Thr  Val  Asn  Asn  Cys  Met  Lys  Ala  Gly  Ile  Val  Ala
     690                      695                      700

Ala  Gly  Leu  Gln  Val  Pro  Ala  Ile  Leu  Gly  Ile  Leu  Gly  Gly  Ile  Leu
705                      710                      715                      720

Ala  Leu  Leu  Ile  Leu  Ile  Leu  Leu  Leu  Leu  Leu  Phe  Leu  Arg  Arg  Arg
                    725                      730                      735

Thr  Val  Val  Lys  Glu  Pro  Leu  Leu  Pro  Pro  Asp  Asp  Asp  Thr  Arg  Asp
               740                      745                      750

Asn  Val  Tyr  Tyr  Tyr  Asp  Glu  Glu  Gly  Gly  Gly  Glu  Glu  Asp  Gln  Asp
          755                      760                      765

Phe  Asp  Leu  Ser  Gln  Leu  His  Arg  Gly  Leu  Asp  Ala  Arg  Pro  Glu  Val
     770                      775                      780

Thr  Arg  Asn  Asp  Val  Ala  Pro  Thr  Leu  Met  Ser  Val  Pro  Gln  Tyr  Arg
785                      790                      795                      800

Pro  Arg  Pro  Ala  Asn  Pro  Asp  Glu  Ile  Gly  Asn  Phe  Ile  Asp  Glu  Asn
                    805                      810                      815

Leu  Lys  Ala  Ala  Asp  Ser  Asp  Pro  Thr  Ala  Pro  Pro  Tyr  Asp  Ser  Leu
               820                      825                      830

Leu  Val  Phe  Asp  Tyr  Glu  Gly  Ser  Gly  Ser  Glu  Ala  Ala  Ser  Leu  Ser
          835                      840                      845

Ser  Leu  Asn  Ser  Ser  Glu  Ser  Asp  Gln  Asp  Gln  Asp  Tyr  Asp  Tyr  Leu
850                      855                      860
```

Asn Glu Trp Gly Asn Arg Phe Lys Lys Leu Ala Asp Met Tyr Gly Gly
865                 870                 875                 880

Gly Glu Asp Asp ( 2 ) INFORMATION FOR SEQ ID NO:9:

( i ) SEQUENCE CHARACTERISTICS:
        ( A ) LENGTH: 822 amino acids
        ( B ) TYPE: amino acid
        ( D ) TOPOLOGY: linear ( x i ) SEQUENCE DESCRIPTION: SEQ ID NO:9:

Met Glu Leu Leu Ser Gly Pro His Ala Phe Leu Leu Leu Leu Leu Gln
1               5                   10                  15

Val Cys Trp Leu Arg Ser Val Val Ser Glu Pro Tyr Arg Ala Gly Phe
            20                  25                  30

Ile Gly Glu Ala Gly Val Thr Leu Glu Val Gly Thr Asp Leu Glu
            35                  40                  45

Pro Ser Gln Val Leu Gly Lys Val Ala Leu Ala Gly Gln Gly Met His
50                  55                  60

His Ala Asp Asn Gly Asp Ile Ile Met Leu Thr Arg Gly Thr Val Gln
65                  70                  75                  80

Gly Gly Lys Asp Ala Met His Ser Pro Pro Thr Arg Ile Leu Arg Arg
                85                  90                  95

Arg Lys Arg Glu Trp Val Met Pro Pro Ile Phe Val Pro Glu Asn Gly
                100                 105                 110

Lys Gly Pro Phe Pro Gln Arg Leu Asn Gln Leu Lys Ser Asn Lys Asp
                115                 120                 125

Arg Gly Thr Lys Ile Phe Tyr Ser Ile Thr Gly Pro Gly Ala Asp Ser
            130                 135                 140

Pro Pro Glu Gly Val Phe Thr Ile Glu Lys Glu Ser Gly Trp Leu Leu
145                 150                 155                 160

Leu His Met Pro Leu Asp Arg Glu Lys Ile Val Lys Tyr Glu Leu Tyr
                165                 170                 175

Gly His Ala Val Ser Glu Asn Gly Ala Ser Val Glu Glu Pro Met Asn
            180                 185                 190

Ile Ser Ile Ile Val Thr Asp Gln Asn Asp Asn Lys Pro Lys Phe Thr
            195                 200                 205

Gln Asp Thr Phe Arg Gly Ser Val Ile Glu Gly Val Met Pro Gly Thr
    210                 215                 220

Ser Val Met Gln Val Thr Ala Thr Asp Glu Asp Asp Ala Val Asn Thr
225                 230                 235                 240

Tyr Asn Gly Val Val Ala Tyr Ser Ile His Ser Gln Glu Pro Lys Glu
                245                 250                 255

Pro His Asp Leu Met Phe Thr Ile His Lys Ser Thr Gly Thr Ile Ser
                260                 265                 270

Val Ile Ser Ser Gly Leu Asp Arg Glu Lys Val Pro Glu Tyr Arg Leu
        275                 280                 285

Thr Val Gln Ala Thr Asp Met Asp Gly Glu Gly Ser Thr Thr Thr Ala
    290                 295                 300

Glu Ala Val Val Gln Ile Leu Asp Ala Asn Asp Asn Ala Pro Glu Phe
305                 310                 315                 320

Glu Pro Gln Lys Tyr Glu Ala Trp Val Pro Glu Asn Glu Val Gly His
                325                 330                 335

Glu Val Gln Arg Leu Thr Val Thr Asp Leu Asp Val Pro Asn Trp Pro
            340                 345                 350

```
Ala Trp Arg Ala Thr Tyr His Ile Val Gly Gly Asp Asp Gly Asp His
        355                 360                 365

Phe Thr Ile Thr Thr His Pro Glu Thr Asn Gln Gly Val Leu Thr Thr
370                 375                 380

Lys Lys Gly Leu Asp Phe Glu Ala Gln Asp Gln His Thr Leu Tyr Val
385                 390                 395                 400

Glu Val Thr Asn Glu Ala Pro Phe Ala Val Lys Leu Pro Thr Ala Thr
                405                 410                 415

Ala Thr Val Val Val His Val Lys Asp Val Asn Glu Ala Pro Val Phe
            420                 425                 430

Val Pro Pro Ser Lys Val Ile Glu Ala Gln Glu Gly Ile Ser Ile Gly
        435                 440                 445

Glu Leu Val Cys Ile Tyr Thr Ala Gln Asp Pro Asp Lys Glu Asp Gln
    450                 455                 460

Lys Ile Ser Tyr Thr Ile Ser Arg Asp Pro Ala Asn Trp Leu Ala Val
465                 470                 475                 480

Asp Pro Asp Ser Gly Gln Ile Thr Ala Ala Gly Ile Leu Asp Arg Glu
                485                 490                 495

Asp Glu Gln Phe Val Lys Asn Asn Val Tyr Glu Val Met Val Leu Ala
            500                 505                 510

Thr Asp Ser Gly Asn Pro Pro Thr Gly Thr Gly Thr Leu Leu Leu
        515                 520                 525

Thr Leu Thr Asp Ile Asn Asp His Gly Pro Ile Pro Glu Pro Arg Gln
    530                 535                 540

Ile Ile Ile Cys Asn Gln Ser Pro Val Pro Gln Val Leu Asn Ile Thr
545                 550                 555                 560

Asp Lys Asp Leu Ser Pro Asn Ser Ser Pro Phe Gln Ala Gln Leu Thr
                565                 570                 575

His Asp Ser Asp Ile Tyr Trp Met Ala Glu Val Ser Glu Lys Gly Asp
            580                 585                 590

Thr Val Ala Leu Ser Leu Lys Lys Phe Leu Lys Gln Asp Thr Tyr Asp
        595                 600                 605

Leu His Leu Ser Leu Ser Asp His Gly Asn Arg Glu Gln Leu Thr Met
    610                 615                 620

Ile Arg Ala Thr Val Cys Asp Cys His Gly Gln Val Phe Asn Asp Cys
625                 630                 635                 640

Pro Arg Pro Trp Lys Gly Gly Phe Ile Leu Pro Ile Leu Gly Ala Val
                645                 650                 655

Leu Ala Leu Leu Thr Leu Leu Leu Ala Leu Leu Leu Val Arg Lys
            660                 665                 670

Lys Arg Lys Val Lys Glu Pro Leu Leu Leu Pro Glu Asp Asp Thr Arg
        675                 680                 685

Asp Asn Val Phe Tyr Tyr Gly Glu Glu Gly Gly Glu Glu Asp Gln
    690                 695                 700

Asp Tyr Asp Ile Thr Gln Leu His Arg Gly Leu Glu Ala Arg Pro Glu
705                 710                 715                 720

Val Val Leu Arg Asn Asp Val Val Pro Thr Phe Ile Pro Thr Pro Met
                725                 730                 735

Tyr Arg Pro Arg Pro Ala Asn Pro Asp Glu Ile Gly Asn Phe Ile Ile
            740                 745                 750

Glu Asn Leu Lys Ala Ala Asn Thr Asp Pro Thr Ala Pro Pro Tyr Asp
        755                 760                 765

Ser Leu Met Val Phe Asp Tyr Glu Gly Ser Gly Ser Asp Ala Ala Ser
```

```
                    770                           775                           780
Leu   Ser   Ser   Leu   Thr   Thr   Ser   Ala   Ser   Asp   Gln   Asp   Gln   Asp   Tyr   Asn
785                           790                           795                           800

Tyr   Leu   Asn   Glu   Trp   Gly   Ser   Arg   Phe   Lys   Lys   Leu   Ala   Asp   Met   Tyr
                        805                           810                           815

Gly   Gly   Gly   Glu   Asp   Asp
                  820
```

T-CADHERIN ADHESION MOLECULE

This application is a continuation of application Ser. No. 08/213,361, filed Mar. 14, 1994, now U.S. Pat. No. 5,585,351, which is a continuation of application Ser. No. 07/607,293, filed Oct. 30, 1990, now abandoned.

BACKGROUND OF THE INVENTION

This invention relates to cell surface molecules and more specifically to T-cadherin, a new cell adhesion molecule of the cadherin family.

Cadherins are a family of transmembrane glycoproteins that mediate adhesive interactions in the developing and adult organism through a Ca2+-dependent mechanism (Takeichi, 1988 and 1990, review). It has been suggested that the cadherins arose from a common ancestral gene. Duplication of the gene may have resulted in the formation of a structurally related family of molecules with heterogeneous sequences. Cadherins share their overall structure which, at the extracellular region, is subdivided into a signal peptide, a prepeptide and five related extracellular domains and is followed by a transmembrane domain and a highly conserved stretch of cytoplasmic amino acids, that is suggested to provide a linkage with the cell's cytoskeletal network. The signal peptide and the prepeptide are readily cleaved and are absent from the mature protein. Several members of the cadherin family have been characterized. N-cadherin is found in the nervous system during development and has been shown to be a strong mediator of nerve fiber growth in vitro. In addition to neural tissue, N-cadherin is also expressed in heart and skeletal muscle and in lens cells. E-cadherin (also known as uvomorulin in the mouse) is a component of epithelial cells and P-cadherin is found in placenta.

T-cadherin, which is subject of this application, is a novel member to the cadherin family that shares the overall cadherin structure in the extracellular region, but lacks the conserved cytoplasmic sequences. Therefore, a new mode of T-cadherin function is proposed, in which T-cadherin regulates the adhesive cell properties not through a direct linkage with the cytoskeleton, but through higher membrane mobility and ready access to its extracellular ligand. The pattern of T-cadherin expression suggests a key role in the establishment of the pattern of nerve fiber growth in developing embryos. Furthermore, T-cadherin is the first molecularly characterized polypeptide to be identified in a segmental pattern as epithelial somites undergo the transition to form the dermamyotome and sclerotome. The expression in only one half of the somitic sclerotome, that eventually will give rise to vertebrae, suggests that T-cadherin plays a key role in the segmentation of vertebrate embryos. Segmentation is a crucial property of the vertebral column that allows flexibility and provides an individual with the ability to bend the back. T-cadherin has also been identified in muscle cells and blood vessels. In muscle, T-cadherin may be involved in cell differentiation and function. Expression in blood vessels may suggest that T-cadherin may be associated with the vascularization of tumors. A tumor remains small unless provided with blood capillaries. The control of vascularization that may be possible with the reagents described in this invention, may therefore be useful in controlling tumor formation and metastasis.

The identification of molecules which regulate and direct nerve fiber growth is important to the study of nerve regeneration. After being severed, neurons either degenerate or remain in a state of severe atrophy. The prognosis for recovery of these damaged neurons is very poor. Therefore, the use of molecules such as the T-cadherin cell adhesion molecules may influence neurons to regrow their axons and guide the axons to reinnervate their corresponding target cells. Eventually, this may lead to relief from the disabling effects of stroke or trauma to the nervous system.

There thus exists a need for the identification and characterization of cell surface adhesion molecules which may be involved in regulation of development in the embryo or recovery of traumatized neurons including methods of detecting and utilizing these molecules. The present invention satisfies this need and provides related advantages as well.

SUMMARY OF THE INVENTION

The invention provides substantially purified T-cadherin polypeptides and isolated nucleic acids which encode the T-cadherin polypeptides. Antibodies reactive with various forms of T-cadherin, but not reactive with N-, E- or P-cadherin are also provided. The invention provides methods for detecting the various forms of T-cadherin in a subject as well as a method of detecting tumor growth which consists of inhibiting the activity of T-cadherin in a tumor. A method of effecting traumatized neurons is provided. The method entails treating traumatized neurons with a therapeutically effective dose of T-cadherin.

BRIEF DESCRIPTION OF THE DRAWINGS

Figure 2C:
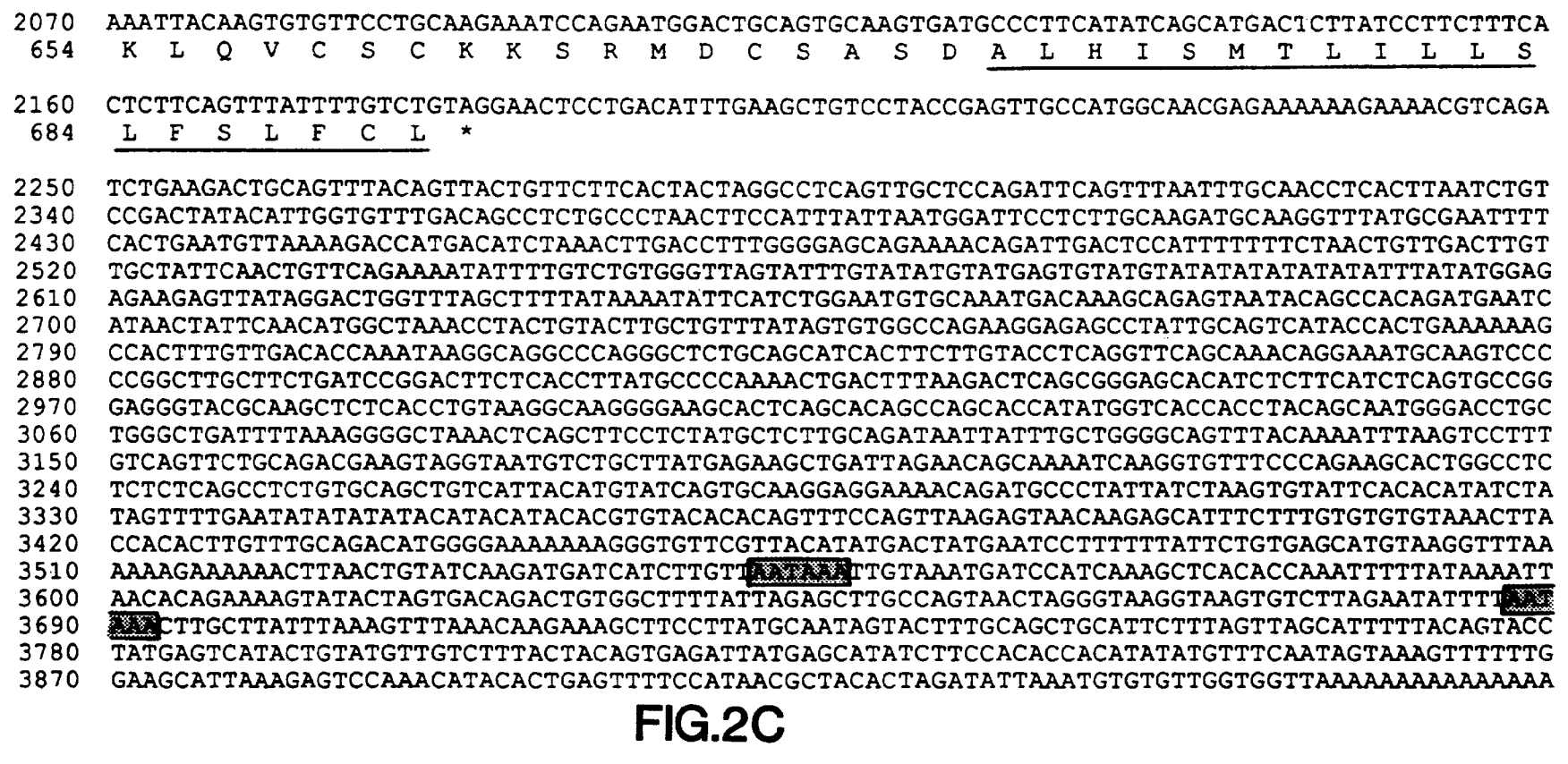

FIGS. 2a to 2f show the nucleotide and predicted amino acid sequence of the T-cadherins. FIGS. 2a, 2b and 2c are the sequences of T-cadherin 1 (SEQ ID NOS. 1 and 2). FIGS. 2d, 2e and 2f show the sequences for T-cadherin 2 (SEQ ID NOS. 3 and 4).

FIGS. 3a and 3b show the amino acid alignment of T-cadherin 1 (266 cDNA) with the related proteins N-cadherin, L-CAM, E-cadherin and P-cadherin (SEQ ID NOS. 5 through 9, respectively).

DETAILED DESCRIPTION OF THE INVENTION

Figure 1:
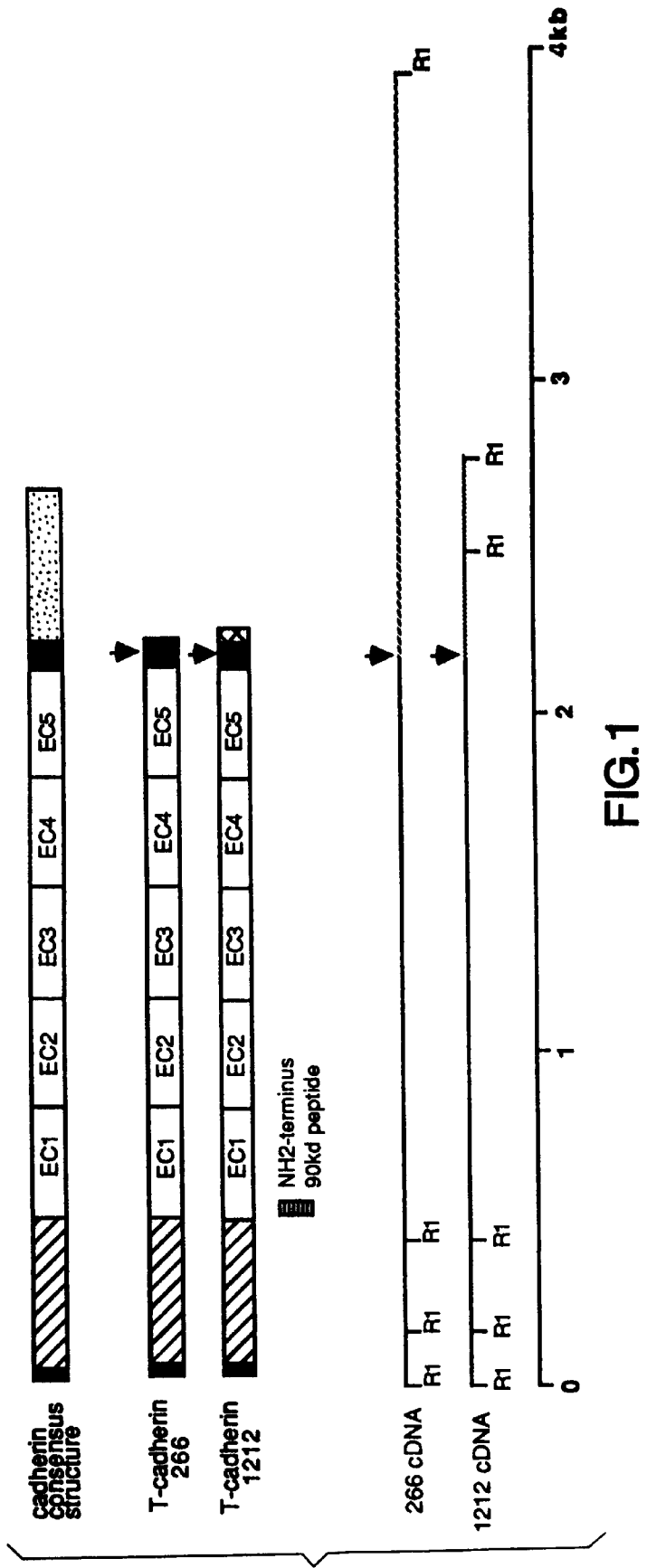
FIG. 1 shows the STRUCTURAL alignment of T-cadherin 1 (266 cDNA) and T-cadherin 2 (1212 cDNA) with the cadherin consensus structure.

T-cadherin ("T-cad;" T=truncated) is a member of the cadherin family of cell adhesion molecules. T-cadherin may be involved in the development of the embryo or recovery of traumatized neurons and therefore may be useful in nerve regeneration. T-cadherin is expressed in the nervous system, as well as the heart, skeletal muscle, blood vessels and the muscle lining the gut and skin. The high expression of T-cadherin in blood vessels may be important in the development of highly vascularized tumors.

T-cadherin shares some but not all structural features of other cadherins. The structural similarity extends to the amino acid level in that the extracellular portion of T-cadherin shows 35–47% identity with the extracellular domains of N-cadherin, E-cadherin, P-cadherin and L-CAM; N-cadherin with 47% amino acid identity being most closely related. Two forms of T-cadherin identified in the present invention lack the cytoplasmic portion found in all other members of the cadherin family. One form of T-cadherin, herein referred to as T-cad 1, appears to be anchored to the membrane through a glycosyl phosphatidylinositol (GPI) linkage. Biochemical evidence for such a linkage has been obtained by showing that T-cadherin can be released from the cellular plasma membrane by phosphatidylinositol specific phospholipase C and can incorporate radiolabeled ethanolamine into the GPI linkage. The other form of T-cadherin, T-cad 2, is predicted by the cDNA to contain sequences for a hydrophobic domain followed by 5 cytoplasmic amino acids. From preliminary transfection of this cDNA into COS-cells, it is likely that this form is also GPI-linked. These data provide evidence for a membrane linkage of T-cadherins that differs from known cadherins, in particular, in their proposed association with the cytoskeleton. In summary, T-cadherin is a member of the cadherin family of cell adhesion molecules that differs in its anchorage to the plasma membrane from known cadherins.

cDNAs have been isolated that encode T-cad 1 and T-cad 2, two closely related, but distinct forms of T-cadherin (FIGS. 2a to 2c and FIGS. 2d to 2f, respectively). The extracellular portion of both forms are identical and contain structural features characteristic of the cadherin family. The two forms differ in their COOH-terminal region in that T-cad 2 cDNA encodes five additional amino acids (FIGS. 3a and 3b). The absence of a cytoplasmic domain can allow for greater mobility of these molecules within the cell membrane and therefore modulate adhesive cell properties.

RNA transcripts encoding both forms of T-cadherin have been detected using RNAse protection probes specific for each form. There is evidence that the different forms of T-cadherin may be developmentally regulated both temporally and in a tissue specific fashion.

As used herein, "T-cadherin" or "T-cad" refers to polypeptides having substantially the amino acid sequence in FIGS. 2a to 2c and FIGS. 2d to 2f, and which are cross-reactive with antibodies reactive with T-cad, but not with N-cadherin, E-cadherin, P-cadherin and L-CAM. Polypeptides comprising the extracellular, transmembrane and truncated cytoplasmic domain of T-cad 1 and T-cad 2 are provided. Minor modifications of the sequence which do not destroy its immunoreactivity also fall within the definition of the protein claimed.

The suggested open reading frame of T-cadherin cDNAs, T-cad 1 and T-cad 2, encode 690 and 695 amino acid proteins, respectively, of predicted molecular mass 76,018 and 76,627 daltons.

It is understood that limited modifications may be made without destroying the biological function of T-cadherin, and that only a portion of the entire primary structure may be required to effect activity. Minor modifications of the primary amino acid sequence may result in proteins which have substantially equivalent or enhanced function.

As used herein, "T-cadherin" refers to a cell adhesion polypeptide having an amino acid sequence substantially equivalent to that shown in FIGS. 2a to 2c and FIGS. 2d to 2f, and may be involved in the development of the embryonal nervous system and in recovery of traumitized neurons.

"Substantially purified," when used to describe the state of T-cadherin, denotes the protein substantially free of the other proteins and molecules normally associated with or occurring with T-cadherin in its native environment.

"Nucleic acid encoding" as used herein, refers to the primary nucleotide sequence of a gene which provides the order of corresponding amino acids in the protein that they specify. Examples of the cadherin nucleic acid sequence are presented in FIGS. 2a to 2c and FIGS. 2d to 2f.

The invention provides nucleic acids (DNA, RNA, or cDNA) encoding the polypeptides of the invention. The nucleic acid may or may not be expressed in the native host. Vectors comprising these nucleic acids are also provided. Numerous cloning vectors are known to those of skill in the art, and the selection of an appropriate cloning vector is a matter of choice. "Transformed host cells" refers to cells which have had vectors, constructed using recombinant DNA techniques, introduced to them. Host cells can be transformed with such a vector and used to express recombinant polypeptides. Host cells can be mammalian, yeast, insect, or bacterial as long as the appropriate vector is used. Methods of recombinant expression are well known in the art, see Maniatis et al., MOLECULAR CLONING: A LABORATORY MANUAL (1982), which is incorporated herein by reference. Thus, recombinant polypeptides and the method of their production are also provided.

The vectors and methods disclosed herein are suitable for use in host cells including a wide range of prokaryotic and eukaryotic organisms. It is understood that "cells" or "host cells" refers not only to the particular subject cell, but also to the progeny of such a cell. The invention provides vectors which are capable of expressing DNA sequences contained therein, where such sequences are operably linked to other sequences capable of effecting their expression. It is implied that these expression vectors must be replicable in the host organism either as episomes or as an integral part of the chromosomal DNA.

Additionally, recombinant DNA methods currently used by those skilled in the art include the polymerase chain reaction (PCR), which, combined with the synthesis of oligonucleotides, allows easy reproduction of DNA sequences. A DNA segment can be amplified exponentially starting from as little as a single gene copy by means of PCR. In this procedure, a denatured DNA sample is incubated with two oligonucleotide primers that direct the DNA polymerase-dependent synthesis of new complementary strands. Multiple cycles of synthesis each results in an approximate doubling of the amount of target sequence. After twenty-five amplification cycles, the amount of target sequence increases by approximately $10^6$-fold. Amplification of first strand cDNAs using the polymerase chain reaction has been used to detect both forms of T-cadherin. The PCR technology is the subject matter of U.S. Pat. Nos. 4,683,195; 4,800,159; 4,754,065 and 4,683,202, all of which are incorporated by reference herein. The cDNAs shown in FIGS. 2a, b, c and 2d, e, f, or any portion of the sequence can be reproduced for cloning and expression purposes by amplifying the desired sequence with PCR and cloning it into a suitable vector, as is well known in the art.

Detection methods for the presence of nucleic acid or protein in cells include hybridization of a nucleic acid probe with the nucleic acid of a cell and cell staining with polyclonal or monoclonal antibodies. Such techniques are accomplished by methods well-known to those skilled in the art.

Polyclonal antibodies against T-cadherin were prepared according to procedures well known in the art. The specificity of the antibodies was examined by carrying out immunohistochemistry and immunoblotting of various tissues including neuronal cells and somites.

Alternatively, anti-T-cadherin antibodies can be prepared by immunizing an animal with synthetic peptides or recombinant protein fragments prepared from the sequence shown in FIGS. 2a to 2c and FIGS. 2d to 2f, as is well known in the art. Selection of anti-T-cadherin antibodies is performed as described above.

Monoclonal antibodies are prepared by immunizing an animal with material containing T-cadherin or synthetic peptides or recombinant protein fragments thereof, followed by isolating antibody-producing hybridoma cells, as is well known in the art. (See, for example, Harlow and Lane, ANTIBODIES: A LABORATORY MANUAL, Cold Spring Harbor, 1988, and the references cited therein, all which are incorporated herein by reference.) Anti-T-cadherin antibodies are selected by performing immunofluorescence analysis of tissue sections where T-cadherin is localized. The identification of antibodies is confirmed by immunoblotting and immunoprecipitation which reveals the predominant 90 kD polypeptide described above. The appropriate hybridoma is reactive with purified T-cadherin or T-cadherin fragments. T-cadherin fragments can be prepared by expressing the T-cadherin cDNAs shown in FIGS. 2a to 2c and FIGS. 2d to 2f in a prokaryotic or eukaryotic expression vector as described above.

Methods of detecting T-cadherin in a subject are also provided. T-cadherin can be detected in a cell sample by using immunological techniques such as labeled antibodies. Such methods including the choice of label are known to those ordinarily skilled in the art. (Harlow and Lane, Supra). Briefly a subject's tissue sample is exposed first to an antibody specific for T-cadherin. After binding of the antibody, a second antibody, appropriately labeled and specific for the anti-T-cadherin antibody, is exposed to the sample previously incubated with the T-cadherin antibody. The secondary antibody can then be visualized or quantitated and the presence of T-cadherin detected. The invention provides a method of inhibiting tumor growth by inhibiting vascularization of the tumor. Treatment of the tumor with anti-T-cadherin antibodies reduces T-cadherin expression and the amount of vascularization.

The invention also provides a method of repairing traumatized neurons of a subject, including trauma due to stroke or injury. Administration of T-cadherin in the region of the traumatized neurons may influence neurons to regrow their axons and guide the axons to reinnervate their target cells.

The following examples are intended to illustrate but not limit the invention. While they are typical of those that might be used, other procedures known to those skilled in the art may alternatively be employed.

EXAMPLE I

Isolation of T-Cadherin

T-cadherin was identified as a concanavalin A-binding glycoprotein in the detergent-resistant membrane skeleton of chicken sympathetic neurons and embryo brain. The membrane skeleton was isolated as a non-ionic detergent resistant polypeptide complex was isolated in buffer A (10 mM Tris/HCl, pH 7.6, 2 mM $CaCl_2$, 5% Nonident P40, 2 mM dithiothreitol, 1 mM phenylmethylsulfonyl fluoride, 50 $\mu$M leupeptin, 5 $\mu$M pepstatin, 4 ng/ml aprotinin) from 13–16 day old chick embryo brains. The 90 kD fragment of T-cadherin was separated from the complex by preparative SDS gel electrophoresis (Laemnli, Nature 227:680–685 (1970)) as described above. Next to contactin, a 130 kD cell adhesion molecule of the immunoglobulin supergene family, T-cadherin is the major concanavalin A-binding glycoprotein of the complex (Ranscht et al., J. Cell Biol. 99:1803–18113 (1984)). The migration of T-cadherin on SDS-PAGE gels under reducing and non-reducing conditions is closely similar, suggesting that few or no intrachain disulfide bonds are present. Protein complexes containing T-cadherin, contactin, actin and approximately 15 other polypeptides were enriched by differential centrifugation and ion-exchange chromatography. The isolated protein complexes resist extraction with a variety of detergents in different salt conditions; thus, the individual components can only be dissociated from the complexes under denaturing conditions. T-cadherin can be purified by SDS preparative gel electrophoresis with a yield of approximately 50 $\mu$g from 50 g starting material.

EXAMPLE II

Protein Microsequencing

Proteins contained in brain polypeptide complex (BPC) were separated by preparative SDS-PAGE and electrophoretically transferred to a polyvinylidene difluoride membrane (Millipore, Burlington, Mass.) by methods well known to those skilled in the art. The 90 kD T-cadherin polypeptide was identified by staining the transferred proteins with Coomassie Brilliant Blue R250, excised and sequenced directly. Transfer conditions and processing were as described by Matsudaira, P., J. Biol. Chem. 262:10035–10038 (1987).

EXAMPLE III

Generation and Affinity Purification of Anti-T-Cadherin Antiserum

The detergent-resistant polypeptide complex was separated into its individual components by preparative SDS-PAGE gel electrophoresis. The 90 kD T-cadherin fragment was excised from several Coomassie-blue stained gels, electroeluted and desalted on exocellulose GF5 (Pierce, Rockford, Ill.). A New Zealand white rabbit was immunized by intramuscular and subcutaneous injections of 100 μg 90 kD T-cadherin polypeptide in Freund's complete adjuvant (1:1). The rabbit was boosted three times in four week intervals with an identical amount of protein in Freund's incomplete adjuvant. Final boosts were intravenous with 50–100 μg protein in phosphate-buffered saline (PBS). Blood was collected 7–10 days after the injections. The antiserum was absorbed on bovine liver acetone powder.

For some experiments, affinity purified antiserum was used. Affinity purification was achieved with T-cadherin immobilized by electrophoretic transfer onto polyvinylidene membranes (Millipore). The polypeptide complex was separated by SDS-PAGE and transferred to polyvinylidene membranes (Towbin et al., Proc. Natl. Acad. Sci. USA 76:356–375 (1979)). Proteins on the transfer were detected by staining with 1% amido black in methanol: acetic acid::water (20:10:70). The 90 kD T-cadherin peptide band was excised from the membrane and blocked for 30–60 minutes with 4% non-fat dry milk in TBST (10 mM Tris/HCl pH 8.0, 150 mM NaCl and 0.05% Tween 20). The T-cadherin strips were incubated with anti-T-cadherin antiserum (1:50 in TBST) for 2 hours at room temperature. Following washes in TBST, bound anti-T-cadherin antiserum was eluted from the strips with 600 μl 0.1M glycine, pH 2.5 for 5 minutes and neutralized immediately. The procedure was repeated five times to obtain sufficient quantities of purified antibody.

Figure 4:
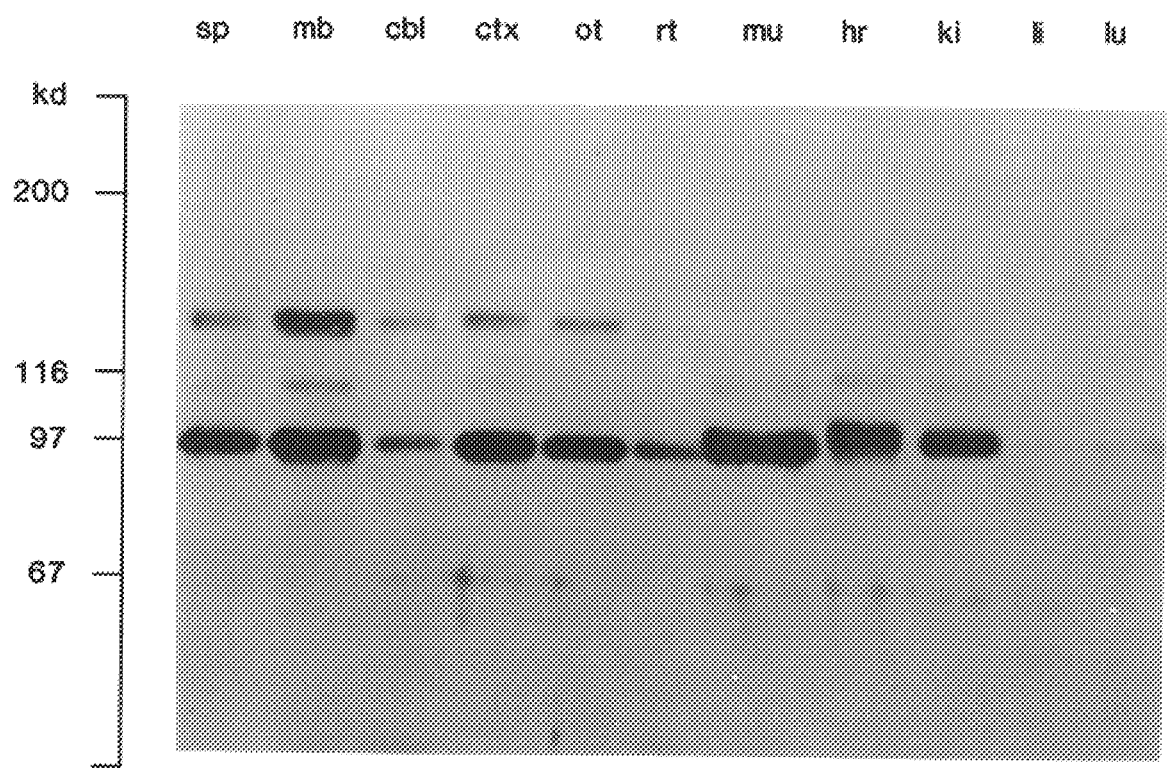
FIG. 4 is an immunoblot of various tissues isolated from 3 day old chicks using antiserum to T-cadherin. Polypeptides having an $M_r$ of 90, 110 and 120 kD are detected in neural tissues whereas only the 90 and 110 kD polypeptides are detected in non-neural tissues. Lane 1, spinal cord; lane 2, midbrain; lane 3, cerebellum; lane 4, cortex; lane 5, optic tectum; lane 6, retina; lane 7, muscle; lane 8, heart; lane 9, kidney; lane 10, liver; lane 11, lung.
Figure 5A:
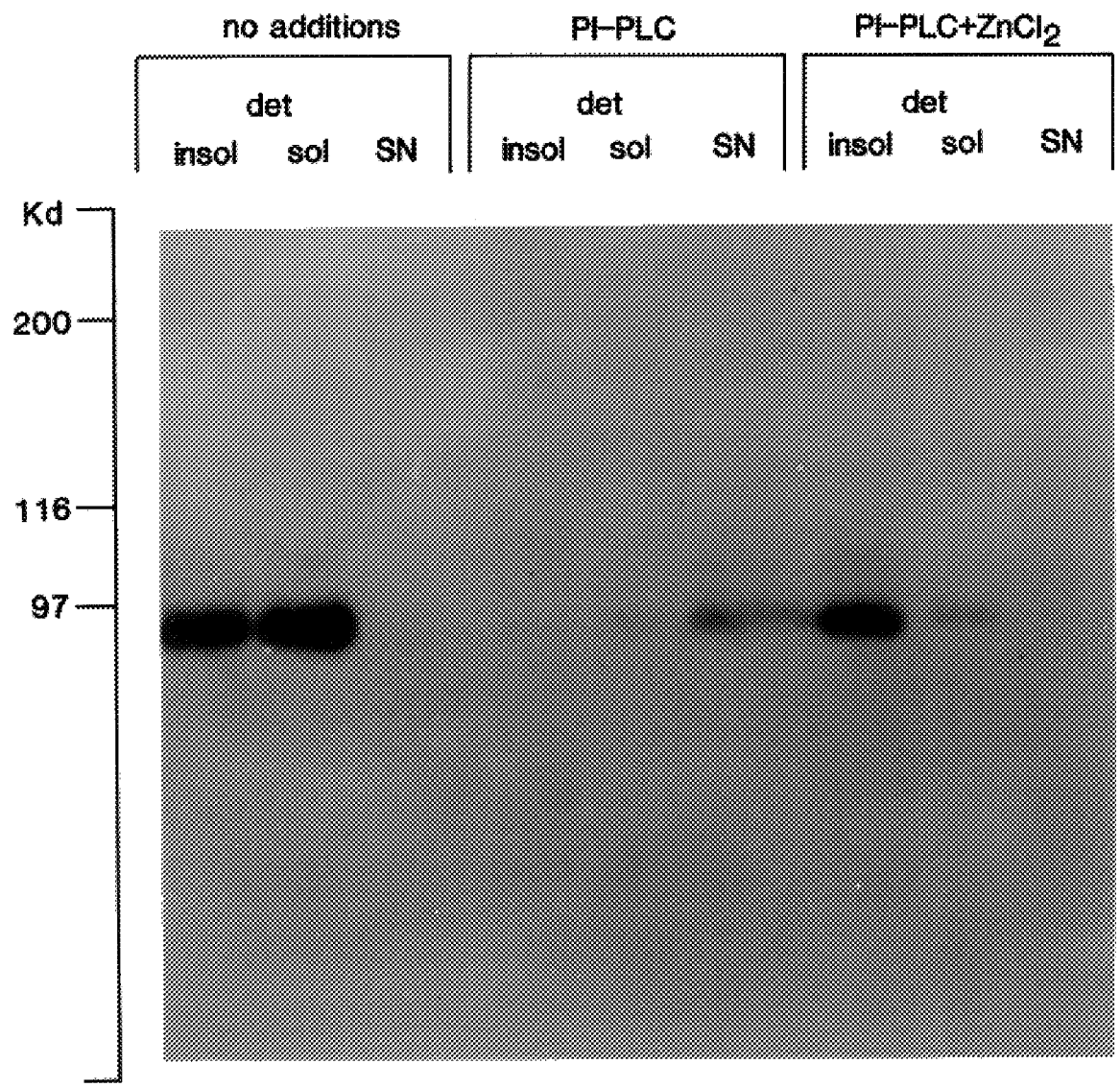
FIG. 5a shows the release of T-cadherin from cultured neurons following phosphotidylinositol phospholipase C (PI-PLC) treatment by Western Blotting with T-cadherin antiserum. T-cadherin is released into the supernatant after PI-PLC treatment (lane 6). The release is blocked by treatment with $ZnCl_2$ (lane 9).
Figure 5B:
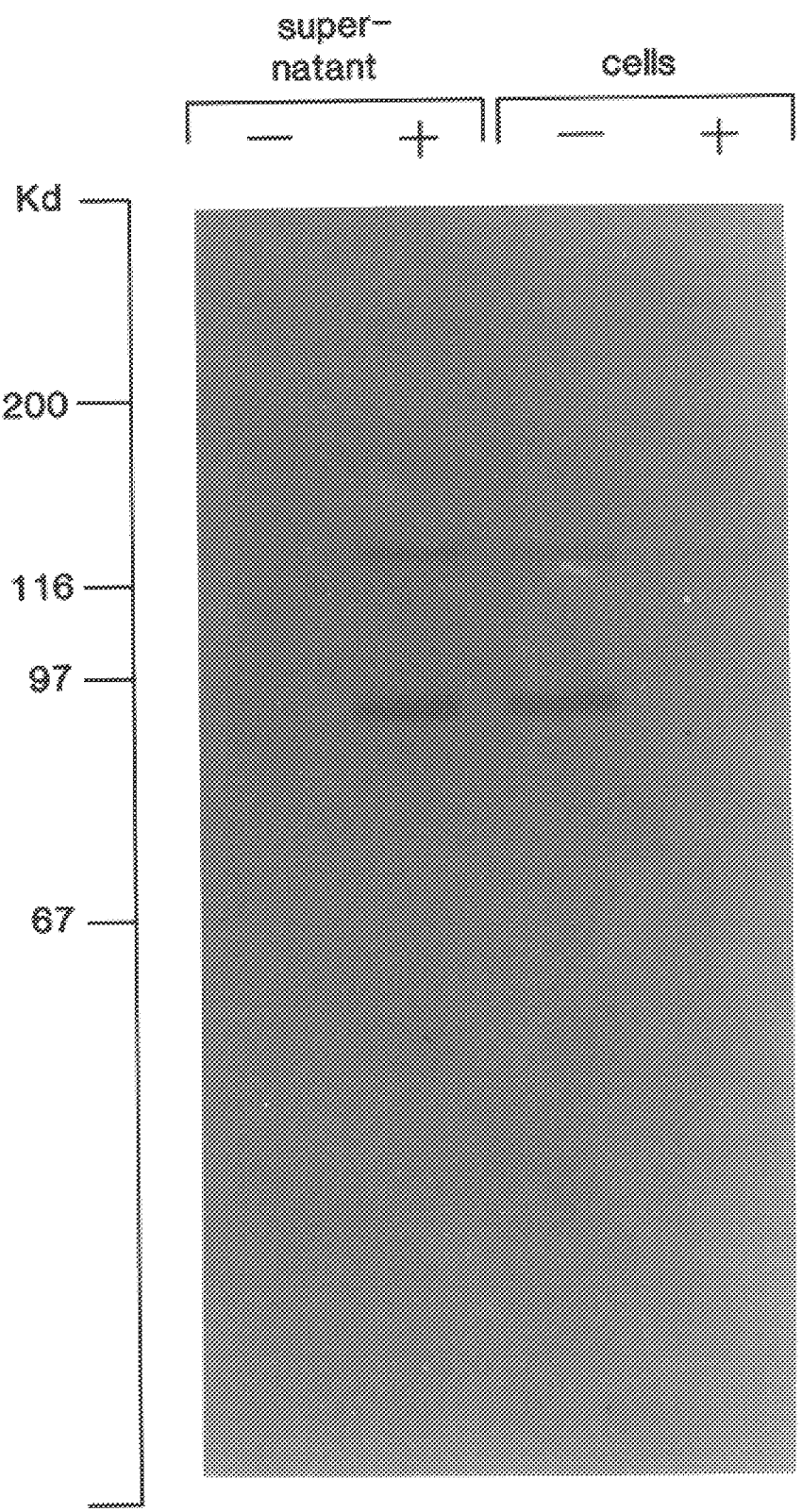
FIG. 5b is an immunoprecipitation of $^3$H-ethanolamine labeled T-cadherin following release from cultured neurons with PI-PLC. Two polypeptides of $M_r$ 90 and 120 kD are released by PI-PLC and are precipitated with T-cadherin antiserum (lane 2).
Figure 6:
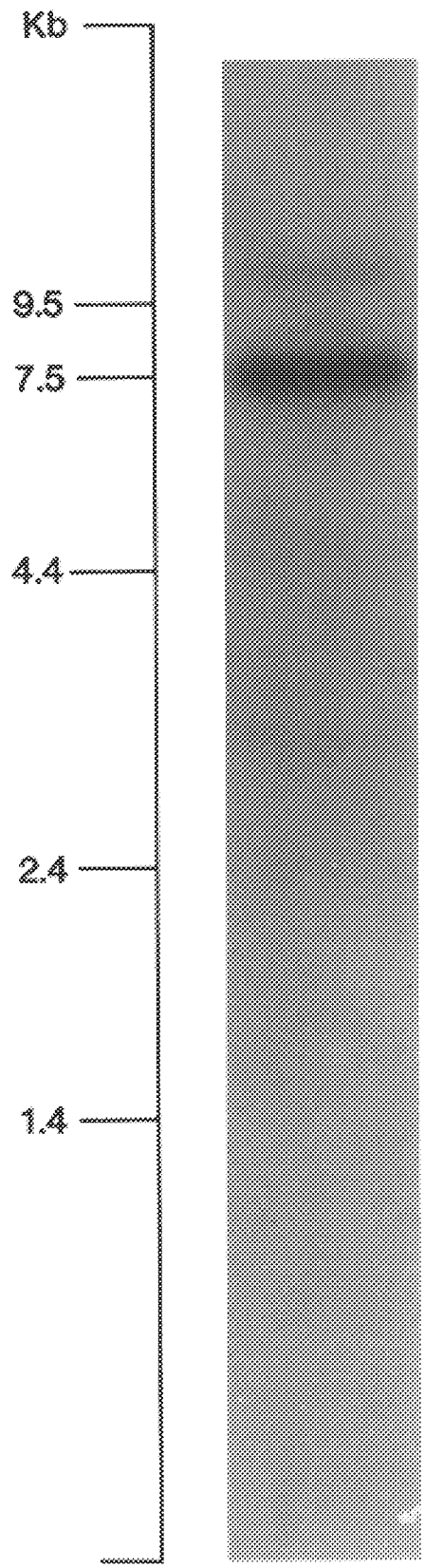
FIG. 6 is an RNA blot of brain tissue probed with a T-cadherin cDNA portion corresponding to the T-cadherin 1 Eco RI-Pst I restriction fragment (1.76 kb). The probe detects two mRNA species of 7.5 and 9.5 kb.
Figure 7A:
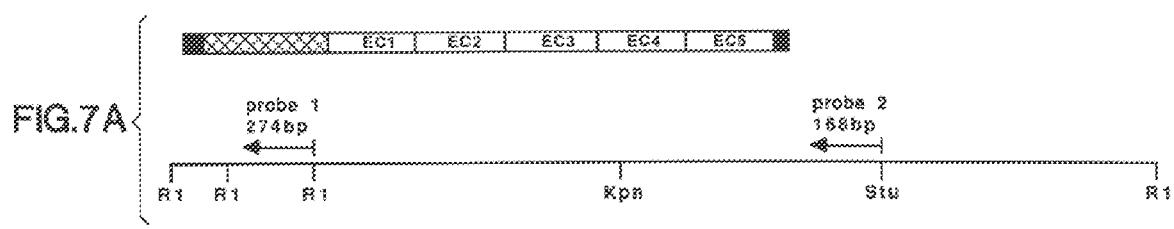
FIGS. 7a and 7b show a RNase protection assay of T-cadherin mRNA. Samples are BR=brain, M=muscle, LI=liver, H=heart, K=kidney, LU=lung, RT=retina from hatched chickens. N=cultured sympathetic neurons as in Example 5. Spinal cord H/H stage 37 and 24. Spinal cord H/H stage 24 separated into D=dorsal, V=ventral and FP=floor plate region. SOM=somites.
Figure 7B:
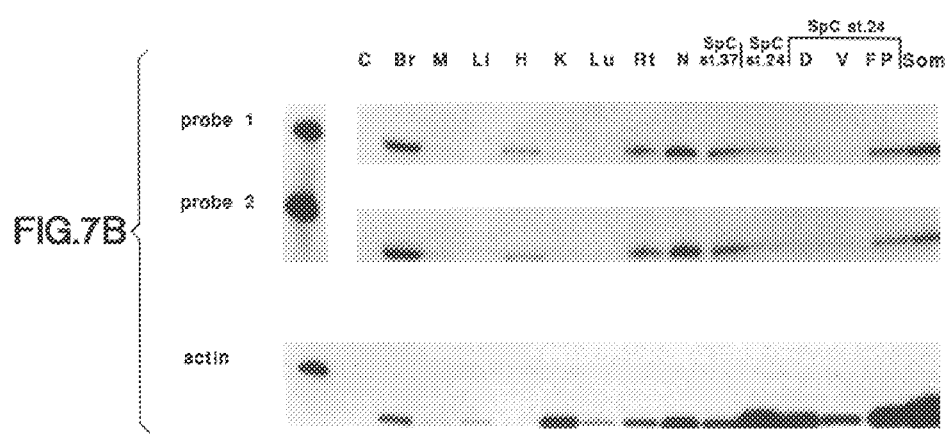

On immunoblots of nervous tissue homogenates, this antiserum recognized a major protein component of 90 kD. In addition, protein species of 110 and 120 kD were detected with the antiserum (FIG. 4). The 110 kD polypeptide is likely to represent T-cadherin with the preptide, since both the 90 and the 110 kD species are obtained after transfection of COS-cells with T-cadherin cDNAs. The 120 kD protein is immunoprecipitated with the T-cadherin antiserum after $^3$H-ethanolamine labelling indicating that this protein is also GPI-linked to the membrane. Therefore, the 120 kD polypeptide is likely to be a nervous system specific form of T-cadherin. In contrast to neural tissue, the T-cadherin antiserum recognizes only the 90 and 110 kD protein species in non-neural tissue samples. Microsequencing of the 17 $NH_2$ terminal amino acids of the 90 kD protein and mapping of this sequence to the protein conceptually translated from the cDNA sequence indicates that the 90 kD protein is a fragment of T-cadherin that starts at amino acid residue 117 (FIGS. 2a to 2c and FIGS. 2d to 2f) and excludes the signal and the prepeptide.

EXAMPLE IV

Immunoblotting Procedures

Various tissues including brain, retina, muscle, liver, heart and kidney were homogenized in buffer A (see EXAMPLE I) and separated by SDS-PAGE. Separated proteins were electrophoretically transferred to a polyvinylidene difluoride membrane. Marker lanes were stained separately with 0.1% amido black in methanol:acetic acid:$H_2O$ (20:10:70) and destained in the identical solution without the dye. For immunoblotting, non-specific binding sites were blocked as described above and the blots incubated for 60 minutes with anti-T-cadherin antiserum (1:150 for both the non-purified and the purified antiserum). Following washes in TBST, bound antibodies were detected with 1 μCi/ml $^{125}$I goat anti-rabbit immunoglobulin (ICN Biochemicals Inc., Costa Mesa, Calif.) followed by autoradiography using Cronex Lightning Plus screens. In some experiments the blots were reacted using alkaline phosphatase conjugated goat anti-rabbit immunoglobulin and 5-bromo-4-chloro-3-indolyl-phosphate (BCIP) and nitro blue tetrazolium (NBT) as enzyme substrates (Protoblot, Progema, Madison, Wis.) or the ECL Western Blotting detection system (Amersham Corporation, Arlington Heights, Ill.).

EXAMPLE V

Phospholipase Digestion of Cultured Sympathetic Neurons

Sympathetic ganglia were dissected from 10 day old chicken embryos in L15 medium. The ganglia were dissociated after a 30 minute digestion with 0.25% trypsin in PBS and plated in L15 culture medium onto culture dishes coated with laminin (5 μg/ml, Telios Pharmaceuticals, Inc., La Jolla, Calif.) at a density of 1.4–1.8×10$^6$ cells/60 mm culture dish. The culture medium was supplemented with 10% dialyzed fetal calf serum, 0.5% methylcellulose, 2 mM glutamine, 0.6 g/l glucose, nerve growth factor and antibiotics. Extensive nerve fiber growth was observed after a 48-hour culture period.

For phospholipase digestion, 48 hour cultures were extensively washed with PBS. The cultures were incubated for 60 minutes at 37° C. with 5U/ml phosphoinositol specific phospholipase C (PI-PLC, a gift from Dr. M. Low, Columbia University, New York) in PLC-buffer (PBS containing 1 mM phenylmethylsulfonyl fluoride, 50 μM leupeptin, 5 μM pepstatin, 4 ng/ml aprotinin and 5 μg/ml $α_2$-macroglobulin). The released material was collected, freed of cellular debris by centrifugation and concentrated 10 fold by ultrafiltration. The neuronal cells were peeled off the laminin substrate, washed with PLC-buffer and homogenized in 200 μl H-buffer (10 mM Tris/HCl, pH 7.5, 2 mM $CaCl_2$, 2% Nonidet-P40, 0.25 mM dithiothreitol and protease inhibitors phenylmethylsulfonyl fluoride, leupeptin, pepstatin, aprotinin as above). Detergent-soluble and insoluble material was separated by centrifugation at 100,000 g for 45 minutes at 4° C. Control samples received PLC-buffer only; in two experiments 5 mM $ZnCl_2$ was included during the digestion with the phosphoinositol specific phospholipase.

Released and cellular components of the PI-PLC treated cultures were separated by SDS-PAGE and analyzed on Western blots. In control samples (no additions), T-cadherin was found in the detergent soluble and insoluble fraction of the cells. T-cadherin was not detectable in the supernatant after the 60 minute incubation period. In contrast, when cells were treated with PI-PLC, essentially all of the T-cadherin was released into the supernatant after 60 minutes. This release was blocked by $ZnCl_2$ treatment of cells, an inhibiter of PI-PLC.

T-cadherin is secreted into the culture medium over longer culture periods (≧18 hours). In the culture medium, T-cadherin appears in a highly soluble form as well as in association with an insoluble complex of extracellular matrix components that is pelleted by centrifugation of the culture supernatant at 100,000 g for 3 hours.

EXAMPLE VI

Labeling with $^3$H-Ethanolamine and Fluorography

Cultures of sympathetic neurons were grown for 48 hours and then labeled for 18 hours with $^3$H-ethanolamine (100 μCi/ml; specific activity 19–24 Ci/mmol (Amersham, Arlington Heights, Ill.) in supplemented L15 medium. Labeled cultures were either treated with phosphatidylinositol-specific phospholipase C as described below or processed immediately for analysis. The cells were lysed in H-buffer (10 mM Tris/HCl, pH 7.5, 2 mM $CaCl_2$, 2% Nonidet-P40, 0.25 mM dithiothreitol and protease inhibitors: 1 mM phenylmethyl-sulfonyl fluoride, 50 mM leupeptin, 5 µM pepstatin, 4 ng/ml aprotinin) and the proteins separated by SDS-PAGE. Gels were stained with Coomassie Brilliant Blue R250, destained and equilibrated in water. For fluorography processing, the gels were equilibrated in dimethylsulfoxide (DMSO) for 30 minutes and then treated for 60 minutes with 20% 2,5-Diphenyloxazole (PPO) in DMSO. Gels were dried after extensive washing in water and exposed for 4–12 weeks with presensitized Kodak XAR-5 film.

EXAMPLE VII

Immunoprecipitation

T-cadherin was immunoprecipitated from $^3$H-ethanolamine labeled sympathetic neuronal cultures. Following the labeling period, as in EXAMPLE IV, the cultures were thoroughly washed and lysed with 150 mM NaCl in 10 mM Tris/HCl, pH 7.0, 150 mM NaCl, 1% Deoxycholate, 1% Nonident-P40, 0.2% sodium dodecylsulfate, 1 mM phenylmethylsulfonyl fluoride, 50 µM leupeptin, 5 µM pepstatin, 4 µg/ml aprotinin and 1 mM dithiothreitol. The lysate was cleared by centrifugation at 16,000 g for 30 minutes at 4° C. T-cadherin was complexed from the soluble protein pool with anti-T-cadherin antiserum (1:50) for 60 minutes at 4° C. The antigen/antibody complexes were precipitated with fixed staphylococcus aureus (Pansorbin, Calbiochem, La Jolla, Calif.). Precipitates were washed by centrifugation at 3000 g for 20 minutes through layers of 5%, 10% and 20% sucrose. The precipitates were resuspended in SDS-PAGE loading buffer (Maniatis et al., Supra) and analyzed by SDS-PAGE followed by fluorography as described above.

EXAMPLE VIII

Immunocytochemistry

The localization of T-cadherin was examined using indirect immunofluorescence techniques. Chicken embryos between day 2 and 8 of embryonic development were staged using the criteria of Hamburger and Hamilton (J. Morph. 88:49–192 (1951)) (H & H). The animals were fixed by immersion into PLPA-fixative (100 mM Na-periodate, 75 mM lysine and 3% paraformaldehyde in PBS) or 4% paraformaldehyde alone for 1–3 hours depending on their size. The tissue was kryoprotected by successive immersion into 5% and 10% sucrose in PBS for 8–12 hours, embedded in Tissue-Tek (Miles Laboratories Elkhart, Ind.) and frozen at –70° C. Serial sections of 15 µgm thickness were cut on a kryostat and collected on gelatine/chromalum (1% gelatine/ 0.4% chromalum) coated slides. Sections were stained for 3–4 hours at room temperature with rabbit anti-T-cadherin (1:100). Bound antibodies were detected with FITC or TRITC conjugated goat anti-rabbit IgG (1:150, Cappel Laboratories, Inc., Westchester, Pa.) Antibody dilutions were in GST-PBS (10% normal goat serum and 0.02% Triton-X100 in PBS), washes after each incubation step with PBS only. Stained sections were mounted with immunomount containing 2% 1,4-Diazabicyclo- (2.2.2)-octane (Aldrich, [Milwaukee, Wis.) to prevent rapid bleaching.

In the developing spinal cord at stage 20 (FIG. 8d), (H & H), motor neurons are in their early phase of differentiation and axon extension. Commissural axons that project from dorsolateral and dorsomedial sites to the floor plate region have commenced to extend processes towards the floor plate that serves as their intermediate target. At this stage of development, T-cadherin was found to be expressed on the cell bodies and nerve fibers of motor neurons and on ventral neuroepithelial cells including the floor plate. Other neurons or their precursors were not stained at this early stage.

At stage 24 (FIG. 8e), the majority of commissural axons have crossed the ventral midline of the spinal cord projecting through the ventral ridge of the floor plate. At this stage, the staining intensity of T-cadherin was strikingly increased in the floor plate region. Comparatively little staining was detected in other areas of the neural tube. The pattern of T-cadherin expression includes the floor plate epithelial cells as in previous stages and a segment of the commissural axons as they cross this area. This pattern suggests that commissural axons are stained by anti-T-cadherin only in the segment in contact with the floor plate. The expression in the floor plate region was transient, since in older animals little staining or none can be detected in the floor plate area.

Figure 8A:
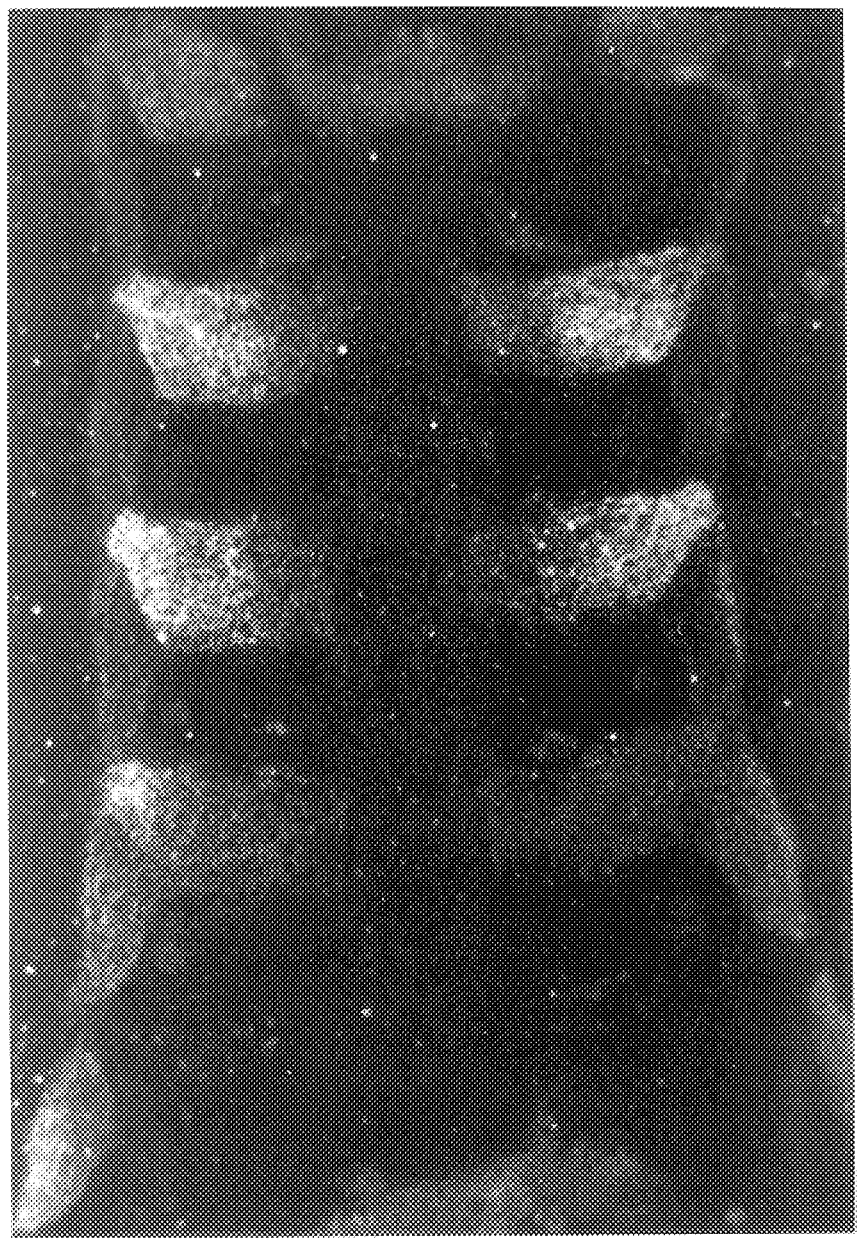
FIGS. 8a to 8h are an immunohistochemistry analysis of T-cadherin expression in the developing nervous system. The tissues examined are: (8a, 8b, 8c) somites H/H stage 23; (8d, 8e, 8f) developing spinal cord, (8d), H/H stage 20, (8e), H/H stage 24 and (8f), H/H stage 32; (8a) blood vessel; and (8h) muscle.
Figure 8B:
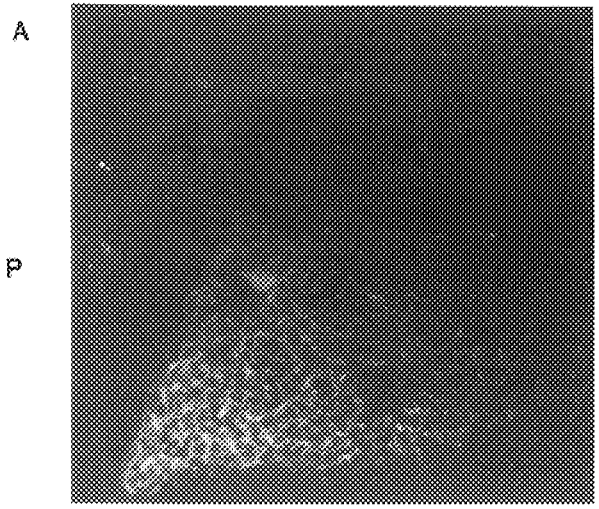
Figure 8C:
Figure 8D:
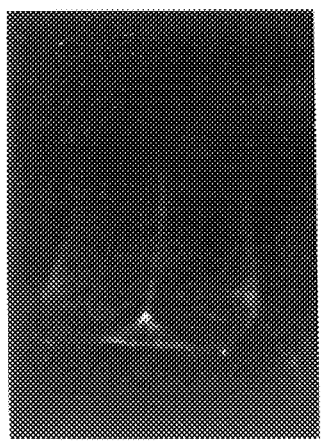
Figure 8E:
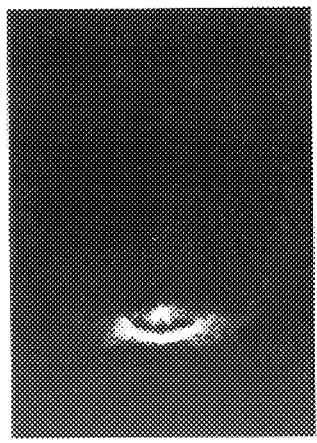
Figure 8F:
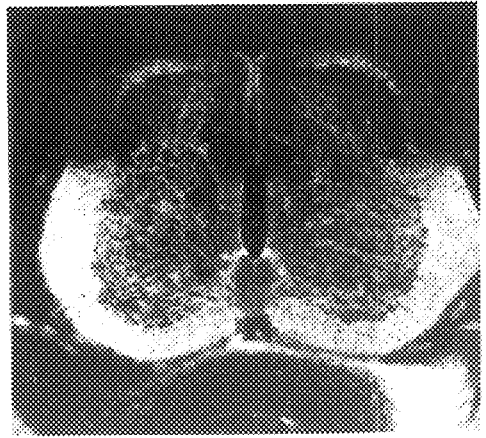
Figure 8G:
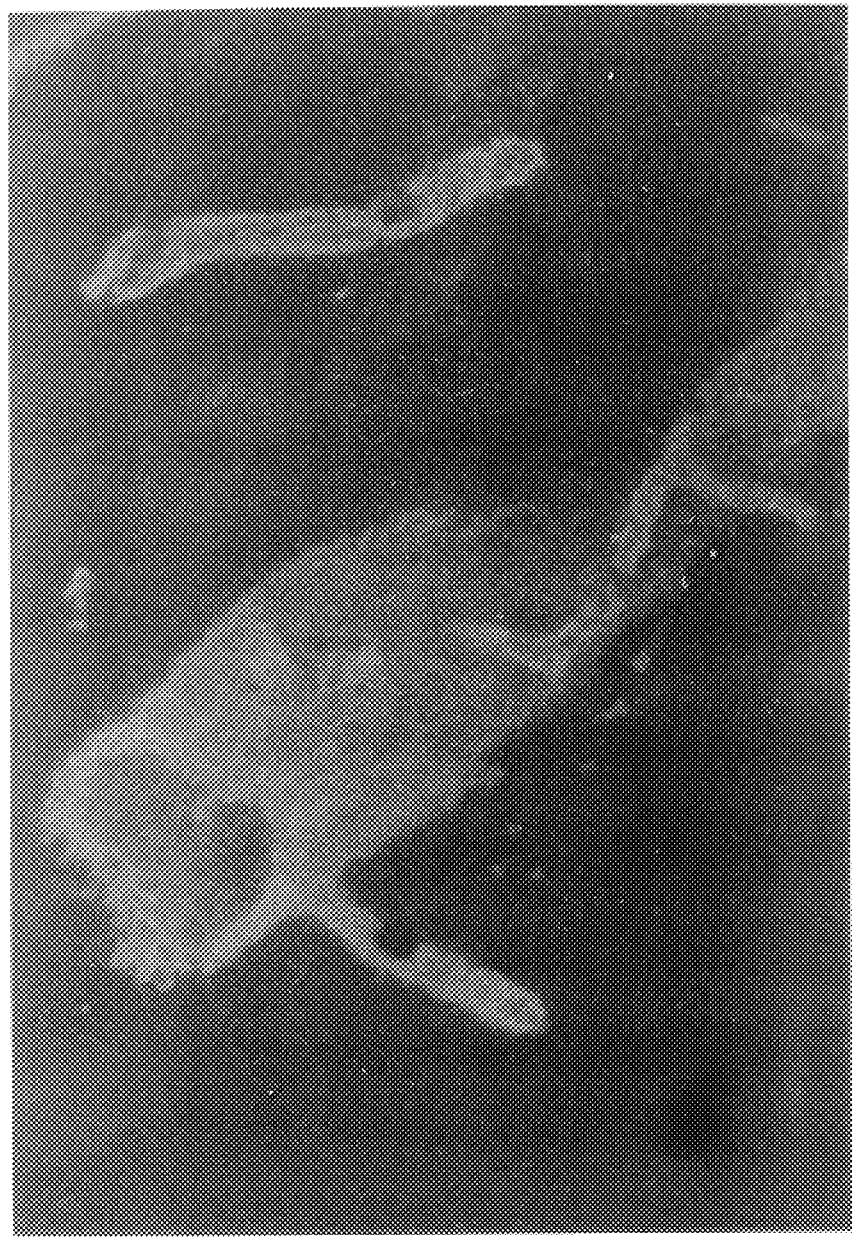
Figure 8H:
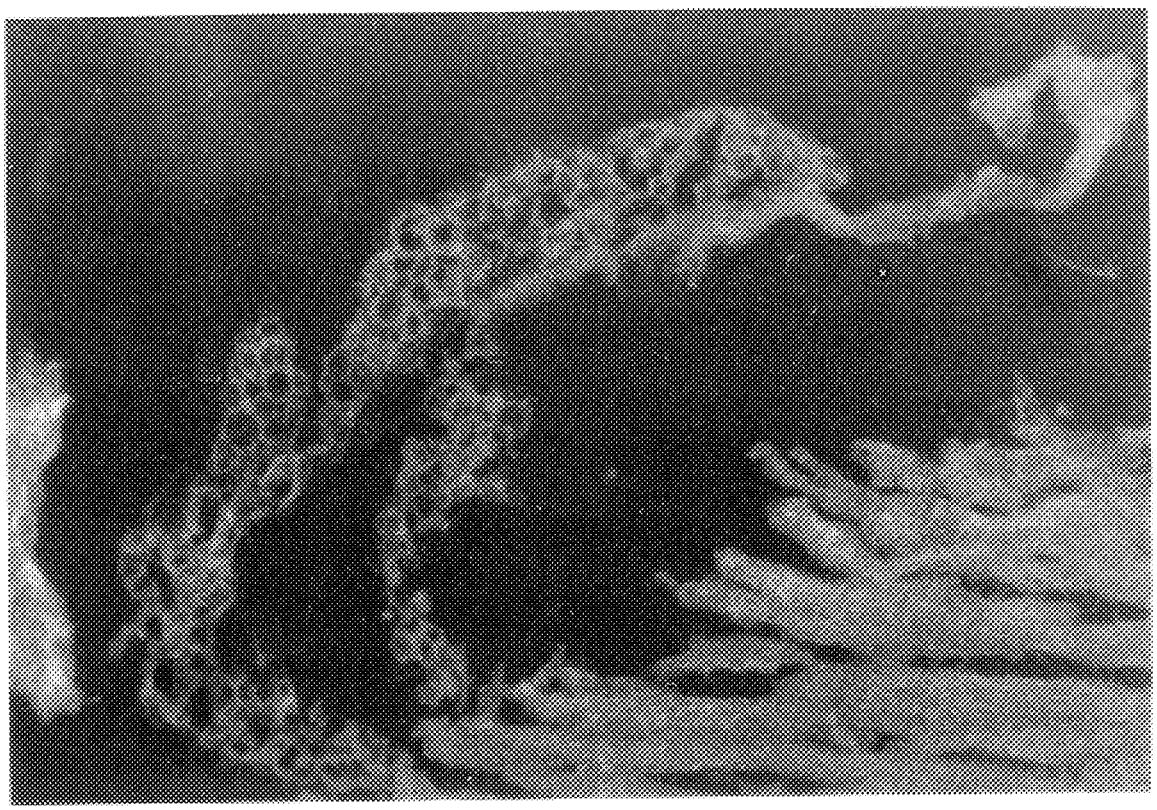
Figure 4:
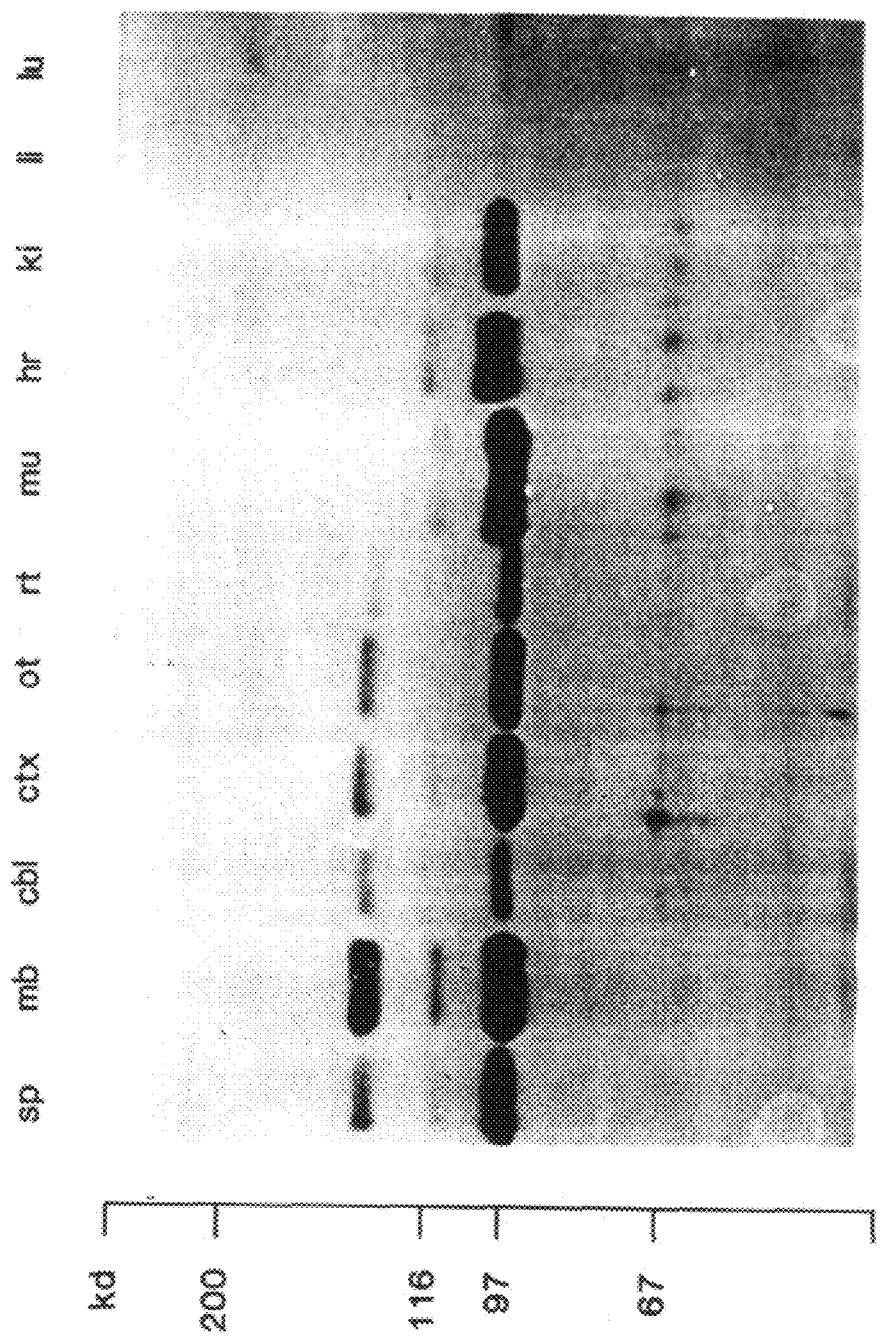
Figure 5A:
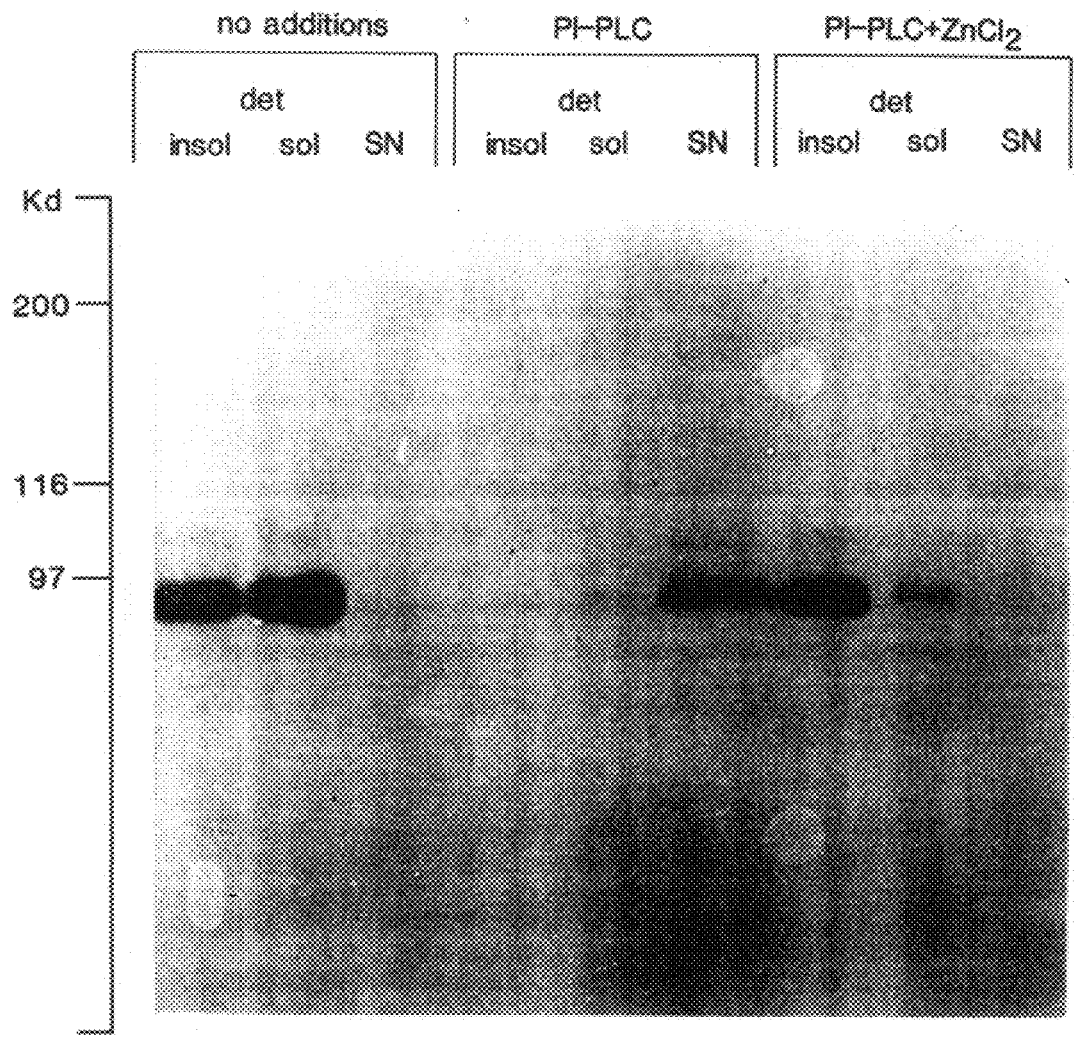
Figure 5B:
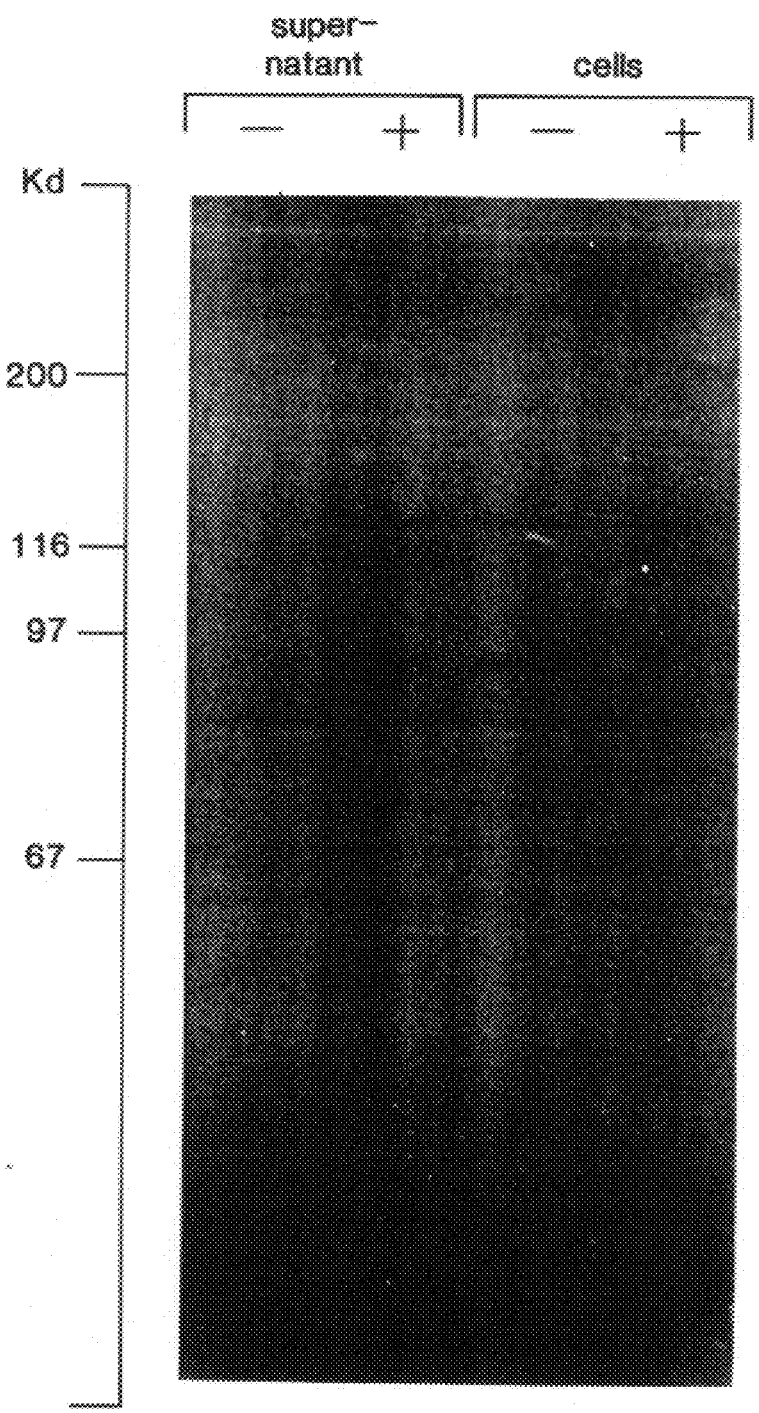
Figure 6:
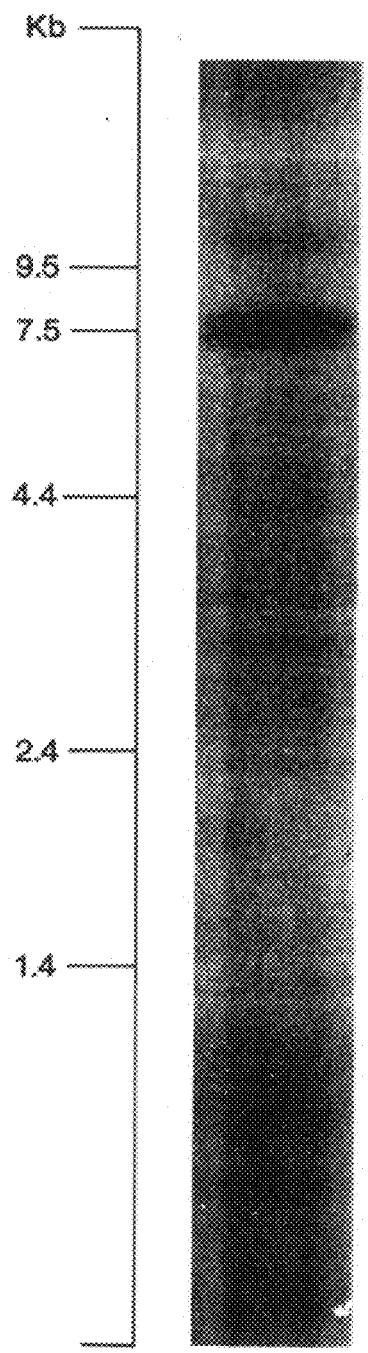
Figure 8A:
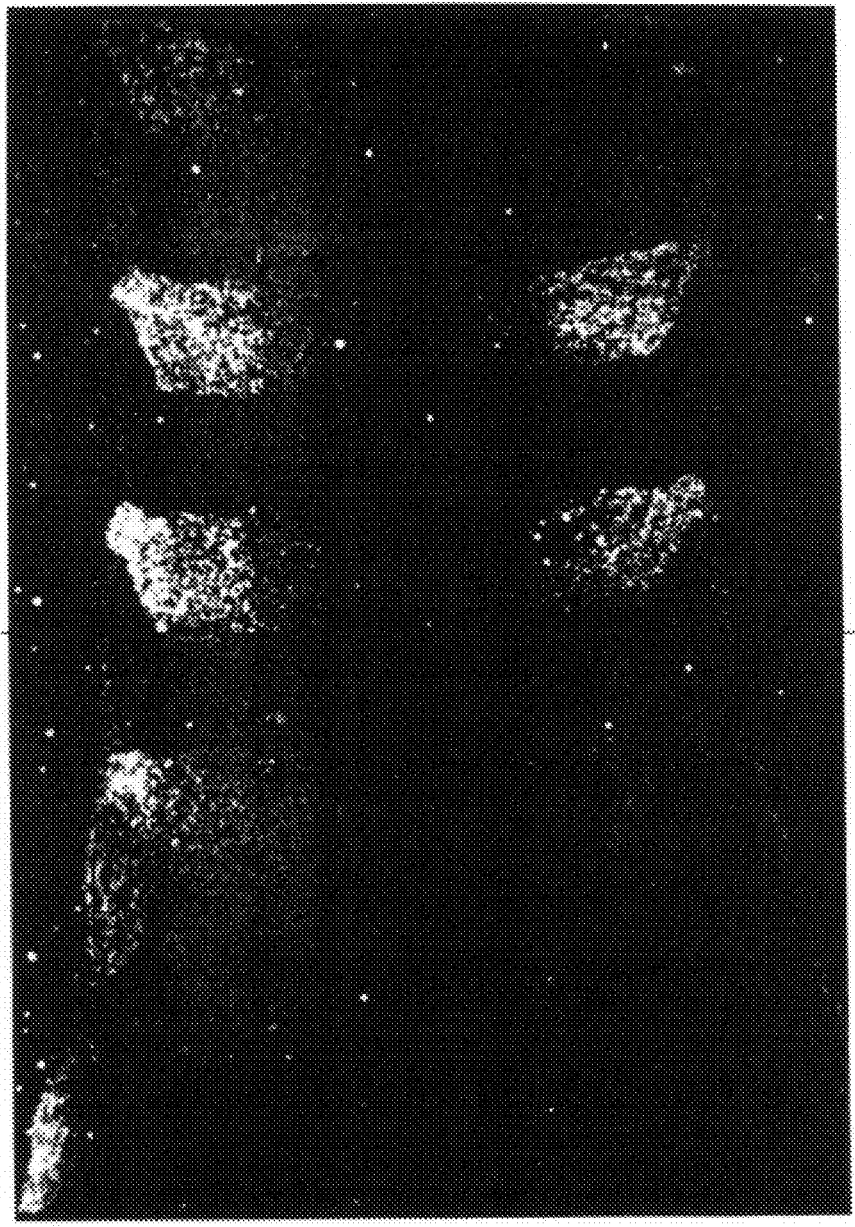
Figure 8C:
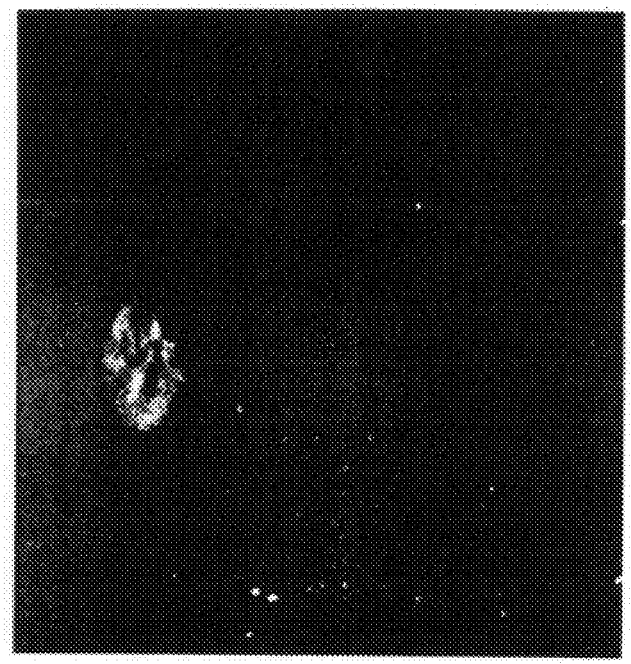
Figure 8B:
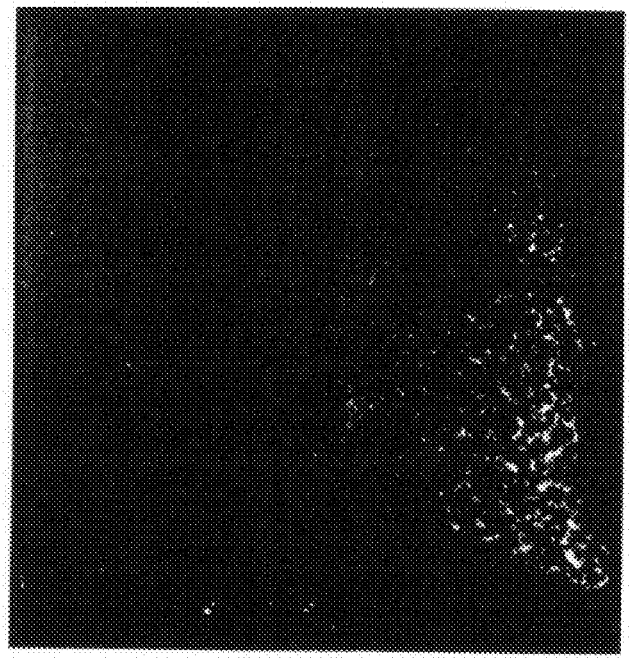
Figure 8F:
Figure 8E:
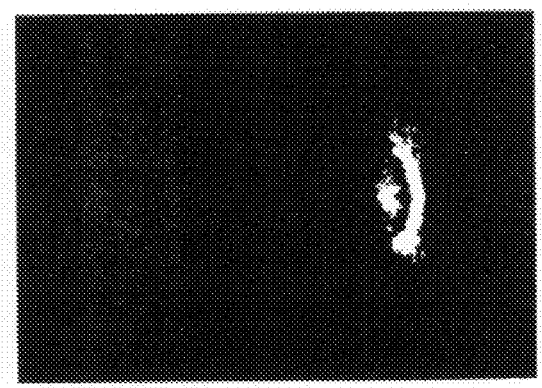
Figure 8D:
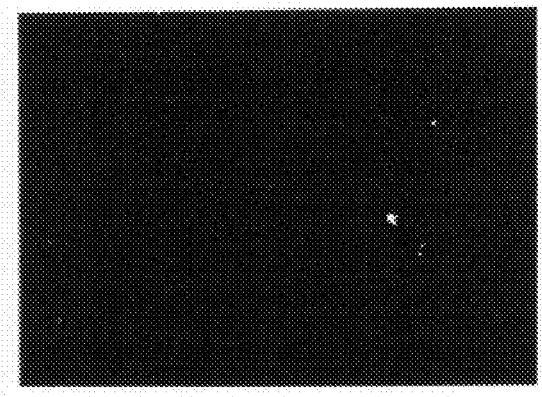
Figure 8G:
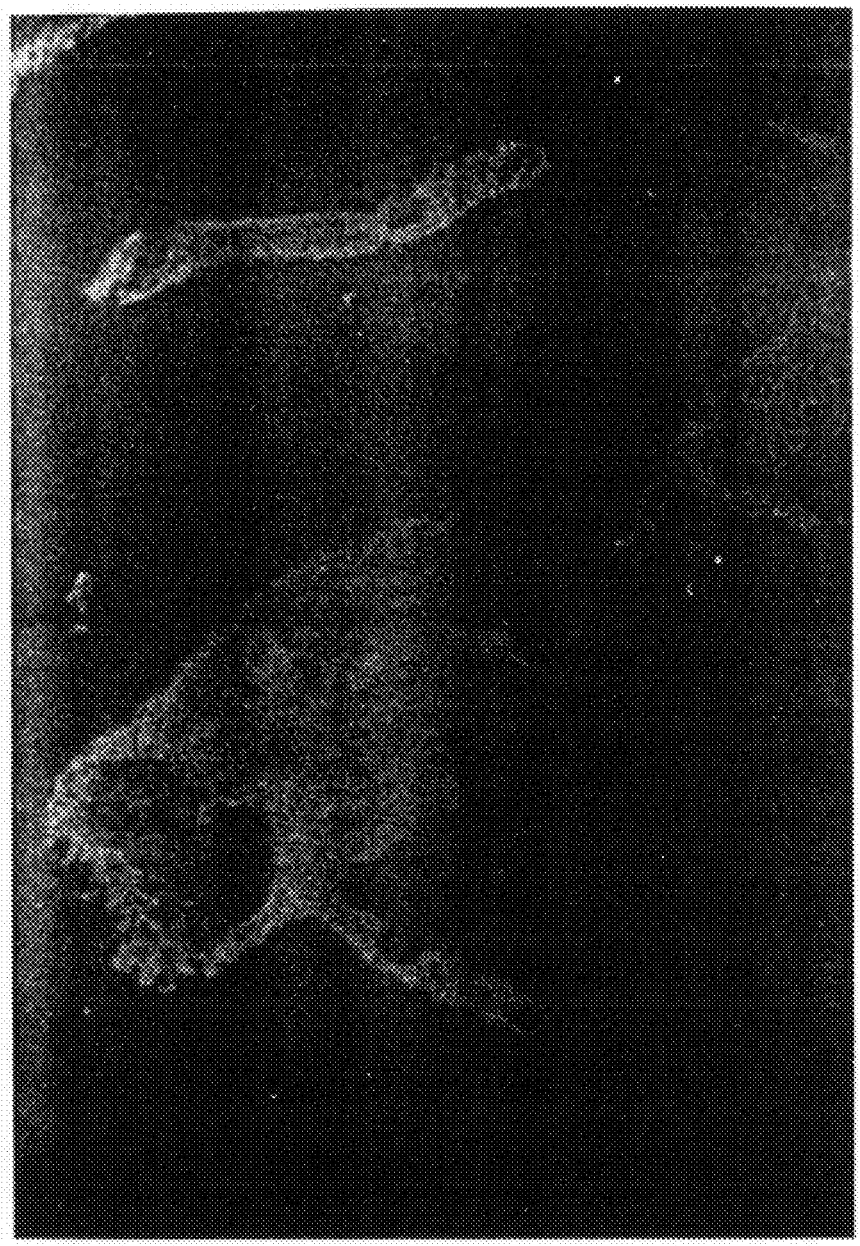
Figure 8H:
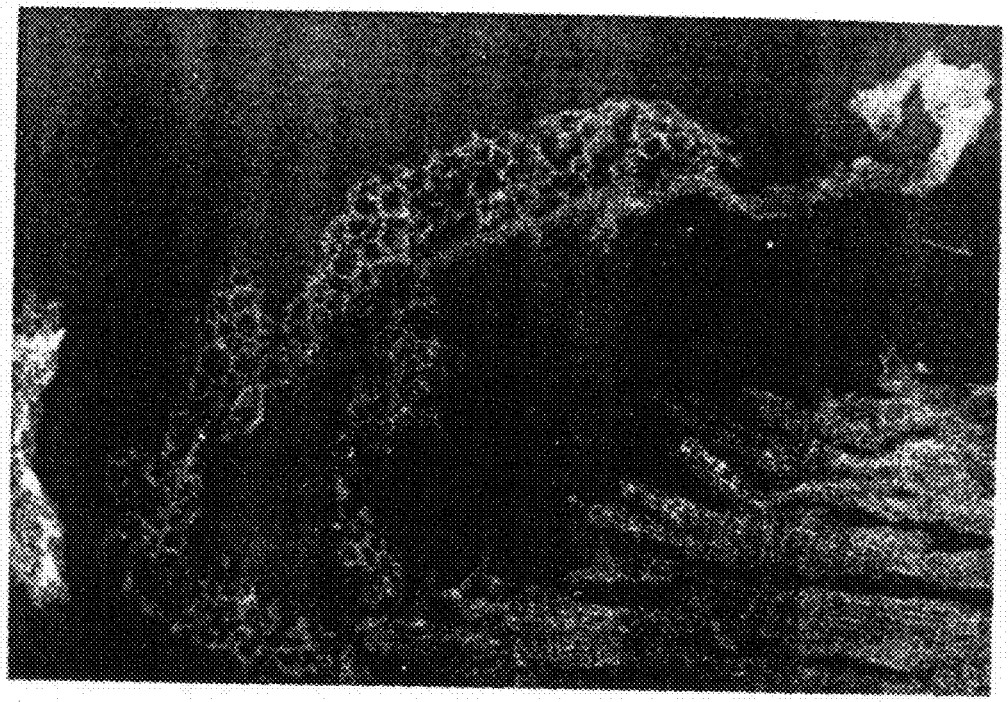

Motor neurons select as their intermediate targets the anterior region of the somitic sclerotome (Keynes and Stern, Nature 310:786–789 (1984)), thus establishing a segmental pattern of nerve projections. In coronal sections of stage 22–23 chicken embryos, T-cadherin was expressed in a striking segmental pattern on the surface of posterior somite cells (FIG. 8a). The spinal nerve fascicles crossing the anterior somite regions were identified in an adjacent section with anti-contactin antibodies (FIG. 8b). The segmental pattern of T-cadherin expression was observed as early as neural crest cells enter the somite regions.

EXAMPLE IX

Identification of cDNA Clones Encoding T-cadherin

A cDNA library generated from embryonic day 13 chicken brain (Ranscht, J. Cell Biol. 107:1561–1573 (1988)) was screened for cDNA clones encoding T-cadherin. Nitrocellulose replica filters of a lambda gt 11 expression library from embryonal day 13 chick brain were screened with affinity purified anti-T-cadherin antiserum (1:40). Screening was essentially as described by Maniatis, incorporated herein by reference. Alkaline phosphatase conjugated goat anti-rabbit immunoglobulin and 5-bromo-4-chloro-3-indolyl phosphate (BCIP) and nitro blue tetrazolium (NBT) substrates (Protoblot, Progema) were used as a detection system. In the initial screening one clone was isolated from $7 \times 10^5$ amplified and $8 \times 10^4$ unamplified recombinants. This clone represented a true T-cadherin transcript by two criteria:

1) The cDNA encoded a fusion protein that was recognized by anti-T-cadherin antiserum. Affinity purification of the antiserum on recombinant fusion protein selected antibodies specific for the 90 kd protein in brain homogenates on Western blots. Moreover, the affinity purified antiserum stained in indirect immunofluorescence on sections of stage 22–23 chick embryos posterior somite segments.

2) Conclusive evidence that the selected cDNA represented a T-cadherin transcript was obtained by comparison of the conceptually translated cDNA sequence with the amino acid sequence obtained by microsequencing of the $NH_2$-terminus of the 90 kD protein. The 17 $NH_2$-terminal amino acids of the 90 kD polypeptide mapped to amino acids 117 to 133 in the open reading frame of the protein conceptually translated from the cDNA sequence (See FIGS. 2a to 2c and FIGS. 2d to 2f).

EXAMPLE X

Isolation of Additional T-cadherin cDNA Clones

Sixteen additional cDNA clones for T-cadherin were isolated by screening both lambda gt 10 (amplified) and lambda gt 11 (unamplified) chick brain libraries with T-cad-2 restriction fragments that were labeled by nick translation (Maniatis et al., Supra; kit from Bethesda Research Laboratories (Gaithersburg, Md.). The restriction fragments constituted nucleotides 440–1559 of the initially isolated clone and included the coding sequences encoding the $NH_2$-terminus of the 90 kD protein. Phage plaques were transferred in duplex to Hybond nylon membranes (Amersham, Arlington Heights, Ill.). The filters were processed successively through 1.5M NaCl/0.5M NaOH for 2 minutes, 3M Na-acetate, pH 5.2 for 5 minutes and 20× SSPE (3M NaCl, 0.2M $NaH_2PO_4 \times H_2O$, 0.02M $Na_2$ EDTA, pH 7.4), dried and baked for 60 minutes in a vacuum oven. Prehybridization was at 42° C. in 50% deionized formamide, 5× SSPE, 1× Denhardts and 100 µg/gml salmon sperm DNA for 2–4 hours. Hybridization was overnight under identical conditions with the probe at $2 \times 10^6$ cpm/filter. The filters were washed under high stringency conditions (0.2×SSPE/ 0.2% SDS at 68° C.) and exposed overnight to Kodak XAR-5 film.

All clones shared restriction sites within their internal nucleotide sequence, but varied in length from 1 to 3.8 kb. EcoR1 restriction fragments of all clones were subcloned into the Bluescript KS+ vector (Stratagene, La Jolla, Calif.) and used for nucleotide sequence determination using a double stranded DNA as a template. Sequence over internal EcoR1 sites was obtained from lambda cDNA templates. The nucleotide sequence of clone 266 (=T-cad 1), one of the longest cDNA clones (3.8 kb) and of cDNA 1212 (=T-cad 2) are shown in FIGS. 2a to 2c and FIGS. 2d to 2f.

EXAMPLE XI

RNA Isolation

Total cellular RNA was isolated from hatched chicks by the guanidinium isothiocyanate method (Maniatis et al., Supra). Briefly, the tissues were homogenized on ice in 4 to 6 mls of 4M guanidinium thiocyanate (GTC) buffer per gram of tissue (94.4 g GTC, 1.67 ml 3M sodium acetate, pH 6.0, 0.5% sarkosyl, 200 µl antifoam A, 500 µl 1 NaOH, to 200 ml with DEPC treated dd $H_2O$, 0.1M final concentration of 2-mercaptoethanol should be added just prior to use). The homogenate is layered onto 4 to 5 mls of 5.7M CsCl solution in a SW 40 centrifuge tube (Beckman, Carlsbad, Calif.). The CsCl solution is prepared in the following manner: 95.97 g CsCl, 0.83 mls 3M sodium acetate pH 6.0, to 100 mls with DEPC-dd $H_2O$ and filter sterilize. The tubes are balanced with GTC buffer and the samples are centrifuged at 32,000 rpm for 18 hours using an ultracentrifuge (Sorvall, Newtown, Conn.). Following centrifugation, the GTC buffer and CsCl solution is aspirated off leaving about 1 ml of CsCl solution covering the RNA pellet. The walls of the tube are rinsed with 1 to 2 mls of GTC buffer and the buffer, including CsCl layer, is carefully removed. The tubes are cut 1–2 cm from the bottom using a hot razor blade and the RNA pellets are rinsed with 400 µl of 20° C. ethanol, dried and resuspended in Tris-EDTA (TE; 10 mM Tris-Hcl, pH 7.6, 1 mM EDTA). The resuspended RNA is purified by extracting twice with an equal volume of phenol/chloroform followed by ethanol precipitation and washing as described above. RNA was quantitated by absorbance at 260 nm ($OD_{260}$ of 1=50 ml/ml). Purity was checked by determining the absorbance ratio at 260 rim compared to the absorbance at 280 nm (OD 260/280≧2.0 for RNA). The RNA samples were stored as ethanol precipitates at −70° C. until further use. From tissues of early developing chicken embryos, RNA was prepared by lithium precipitation as described in Maniatis, Supra. When probed with T-cadherin cDNA, two transcripts of approximately 9.5 and 7.5 kb were detected.

EXAMPLE XII

RNase Protection

RNA transcripts encoding the T-cadherin prepeptide and 3' untranslated regions were generated by in vitro transcription of T-cadherin cDNA. The template for the prepeptide probe (common to T-cad 1 and T-cad 2) was a 274 bp EcoR1 restriction fragment (FIG. 2d, e, f) from lambda gt 11 T-cad 2 cloned into Bluescript KS⁺. The fragment was linearized by digestion with HindIII in the polylinker region. A specific 3' end probe of T-cad 1 was generated by removing 1.5 kb untranslated sequence from the extreme 3' end of clone T-cad 1 by restriction digestion with Stu1/SmaI and religation of the blunt ends. A 168 bp template was obtained by linearizing T-cad 1 DNA with Sfa1. A specific 3' end template for T-cad 2 was generated by cloning its 2.1 kb EcoR1 restriction fragment into Bluescript KS⁺ and digestion of the cDNA fragment with Hpa1. Chicken β-actin cDNA (kindly provided by Dr. D. Cleveland, Johns Hopkins University, Baltimore, Md.) was used as a control. The β-actin cDNA was digested with KpnI and HindIII and cloned into the SP72 transcription vector (Melton et al., Nucleic Acids Res. 13:7035–7056 (1984)). The DNA was linearized by digestion with PvuII. The templates were transcribed in anti-sense orientation in the presence of T7 RNA polymerase and $^{32}$P-rUTP under conditions described by Melton, Supra. Probes were purified on polyacrylamide gels. A 1% aliquot of the total probe was hybridized overnight in 80% formamide, 400 mM NaCl, 4 mM PIPES and 1 mM EDTA at 45° C. to 2–10 µg total RNA from various tissues. Non-hybridized RNA was digested with RNases A and T1 for 60 minutes at room temperature. RNA hybrids were separated on polyacrylamide gels and analyzed after exposure to Kodak XAR-5 film.

All tissues that show a protected fragment with the prepeptide probe, also showed a protected fragment with the 3' fragment, indicating that mRNA encoding the phosphoinositol linked form of T-cadherin exists in the tissues. Brain, heart, retina, cultured sympathetic neurons, stage 37 and 24 spinal cord (especially floor plate), and somites revealed protected fragments.

Although the invention has been described with reference to the presently preferred embodiment, it should be understood that various modifications can be made without departing from the spirit of the invention. Accordingly, the invention is limited only by the following claims.

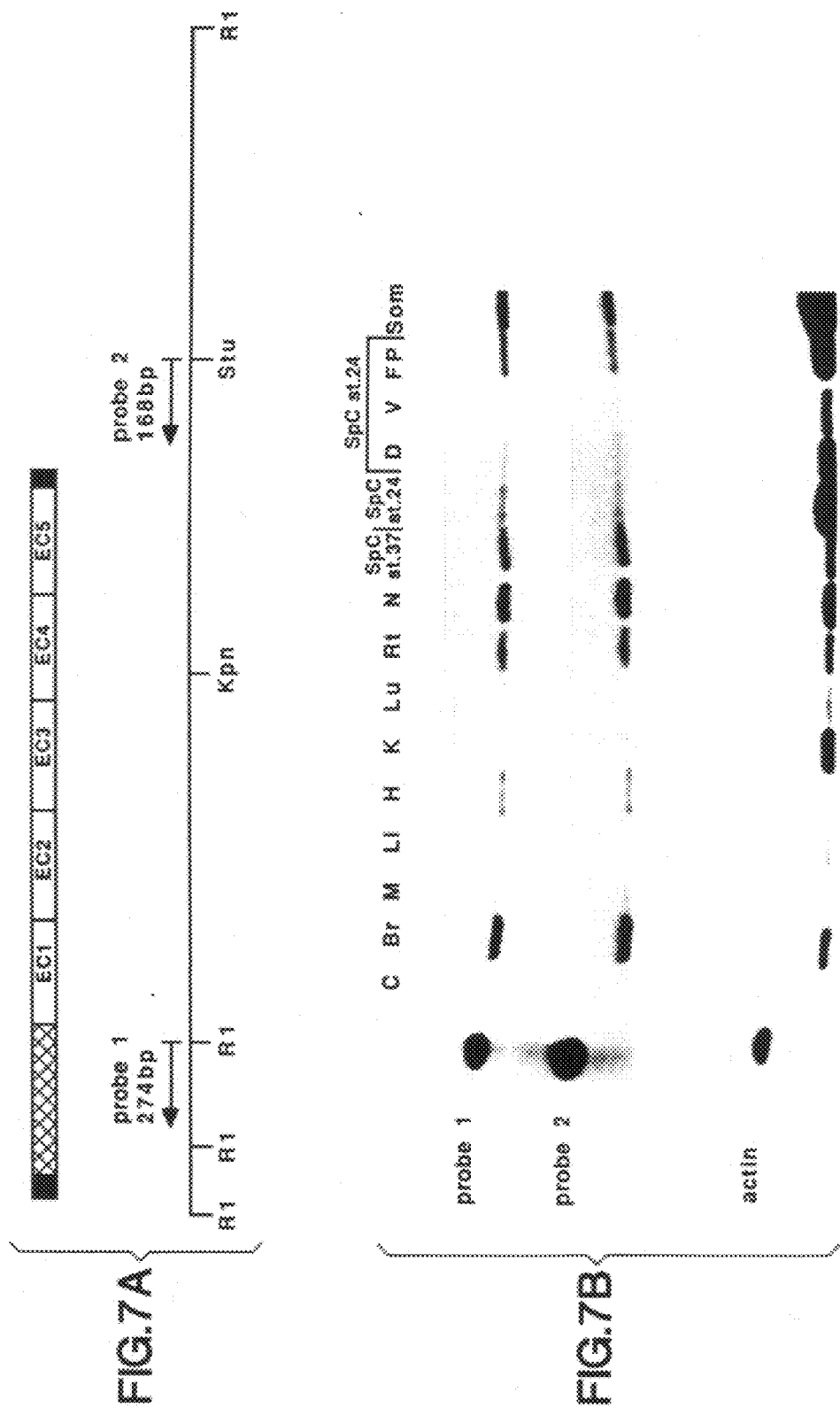

I claim:

1. A substantially purified T-cadherin polypeptide that has substantially the amino acid sequence in SEQ ID NO:2 or SEQ ID NO:4 and that can be specifically bound by an antibody, wherein the antibody specifically binds a T-cadherin polypeptide having the amino acid sequence of SEQ ID NO:2 or SEQ ID NO:4, but the antibody does not specifically bind N-, E-, P-cadherin or L-CAM.

2. The substantially purified T-cadherin polypeptide of claim 1, wherein the polypeptide has a glycosyl phosphatidylinositol linkage to a cell membrane and has no cytoplasmic domain.

3. A T-cadherin polypeptide produced recombinantly by a transformed host cell containing a nucleic acid which encodes the polypeptide of claim 1.

* * * * *

UNITED STATES PATENT AND TRADEMARK OFFICE
CERTIFICATE OF CORRECTION

PATENT NO.   : 5,811,518
DATED        : September 22, 1998
INVENTOR(S)  : Ranscht It is certified that error appears in the above-identified patent and that said Letters Patent is hereby corrected as shown below:

Delete drawing sheets, 4, 5A, 5B, 6, 7A/7B, 8A, 8B/8C, 8D/8E/8F, 8G and 8H, and substitute therefore drawing sheets 4, 5A, 5B, 6, 7A/7B, 8A, 8B/8C, 8D/8E/8F, 8G and 8H. (Attached)

Signed and Sealed this

Twenty-second Day of February, 2005

JON W. DUDAS
*Director of the United States Patent and Trademark Office*